United States Patent
Chambon

(10) Patent No.: US 11,179,363 B2
(45) Date of Patent: Nov. 23, 2021

(54) NON-STEROIDAL SELECTIVE GLUCOCORTICOID RECEPTOR AGONISTIC MODULATORS (SEGRAMS) AND USES THEREOF

(71) Applicant: ASSOCIATION POUR LA RECHERCHE À L'IGBMC (ARI), Blaesheim (FR)

(72) Inventor: Pierre Chambon, Blaesheim (FR)

(73) Assignee: ASSOCIATION POUR LA RECHERCHE À L'IGBMC (ARI), Blaesheim (FR)

( * ) Notice: Subject to any disclaimer, the term of this patent is extended or adjusted under 35 U.S.C. 154(b) by 0 days.

(21) Appl. No.: 16/759,014

(22) PCT Filed: Oct. 23, 2018

(86) PCT No.: PCT/EP2018/079049
§ 371 (c)(1),
(2) Date: Apr. 24, 2020

(87) PCT Pub. No.: WO2019/081517
PCT Pub. Date: May 2, 2019

(65) Prior Publication Data
US 2021/0177798 A1    Jun. 17, 2021

Related U.S. Application Data

(60) Provisional application No. 62/578,036, filed on Oct. 27, 2017.

(30) Foreign Application Priority Data

May 17, 2018  (EP) .................................. 18305612

(51) Int. Cl.
*A61K 31/343* (2006.01)
*A61P 17/06* (2006.01)
(Continued)

(52) U.S. Cl.
CPC .............. *A61K 31/343* (2013.01); *A61P 1/04* (2018.01); *A61P 11/06* (2018.01); *A61P 17/00* (2018.01);
(Continued)

(58) Field of Classification Search
CPC .......... A61K 31/343; A61P 17/00; A61P 1/04; A61P 17/06; A61P 27/14; A61P 19/02; A61P 11/06; A61P 29/00
(Continued)

(56) References Cited

U.S. PATENT DOCUMENTS 6,245,804 B1    6/2001  Lehmann et al.
6,323,199 B1 *  11/2001 Lehmann ............. A61K 31/502
                                                                514/230.5
(Continued)

OTHER PUBLICATIONS

Hua et al. "Glucocorticoid receptor modulators CpdX and CpdX-D3 exhibit the same in vivo antiinflammatory activities as synthetic glucocorticoids." Proc Natl Acad Sci U S A. Jul. 9, 2019; 116(28):14191-14199.
(Continued)

*Primary Examiner* — Taylor V Oh
(74) *Attorney, Agent, or Firm* — Maier & Maier, PLLC

(57) ABSTRACT

Two enantiomers of a SElective Glucocorticoid Receptor Agonistic Modulator (SEGRAM) of Formula 1 or a derivative thereof; to a deuterated form of a SEGRAM of Formula
(Continued)

1 or a derivative thereof; and to the two deuterated enantiomers of a SEGRAM of Formula 1 or a derivative thereof:

(Formula 1)

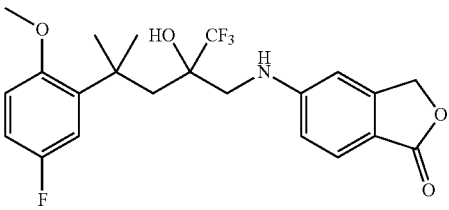

or a pharmaceutically acceptable salt, solvate and/or prodrug thereof.

The present invention also relates to a SEGRAM of Formula 1 or a derivative thereof, or a pharmaceutically acceptable enantiomer, deuterated form, salt, solvate and/or prodrug thereof, for use in the prevention or treatment of an inflammatory disorder in a subject in need thereof.

6 Claims, 39 Drawing Sheets

Specification includes a Sequence Listing.

(51) Int. Cl.
| | |
|---|---|
| *A61P 27/14* | (2006.01) |
| *A61P 11/06* | (2006.01) |
| *A61P 17/00* | (2006.01) |
| *A61P 19/02* | (2006.01) |
| *A61P 29/00* | (2006.01) |
| *A61P 1/04* | (2006.01) |

(52) U.S. Cl.
CPC .............. *A61P 17/06* (2018.01); *A61P 19/02* (2018.01); *A61P 27/14* (2018.01); *A61P 29/00* (2018.01)

(58) Field of Classification Search
USPC .......................................................... 514/470
See application file for complete search history.

(56) References Cited

U.S. PATENT DOCUMENTS

| | | | |
|---|---|---|---|
| 6,344,454 | B1 | 2/2002 | Lehmann et al. |
| 2006/0040933 | A1 | 2/2006 | Jaroch et al. |
| 2019/0151283 | A1* | 5/2019 | Chambon ............ A61K 31/365 |

OTHER PUBLICATIONS

Hua et al. "The glucocorticoid receptor agonistic modulators CpdX and CpdX-D3 do not generate the debilitating effects of synthetic glucocorticoids." Proc Natl Acad Sci U S A. Jul. 9, 2019; 116(28):14200-14209.
Clark et al. "Maps and legends: The quest for dissociated ligands of the glucocorticoid receptor." Pharmacology & Theraputics. Apr. 2012; 134(1):54-67.
Meijsing et al. "DNA Binding Site Sequence Directs Glucocorticoid Receptor Structure and Activity." Science. Apr. 17, 2009; 324(5925):407-10.
Surjit et al. "Widespread Negative Response Elements Mediate Direct Repression by Agonist-Liganded Glucocorticoid Receptor." Cell. Apr. 15, 2011; 145(2):224-41.
Hua et al. "GR SUMOylation and formation of an SUMO-SMRT/NCoR1-HDAC3 repressing complex is mandatory for GC-induced IR nGRE-mediated transrepression." Proc Natl Acad Sci U S A. Feb. 2, 2016; 113(5):E626-34.
Tan et al. "A trilogy of glucocorticoid receptor actions." Proc Natl Acad Sci U S A. Feb. 2, 2016; 113(5):1115-7.
Ratman et al. "How glucocorticoid receptors modulate the activity of other transcription factors: A scope beyond tethering." Molecular and Cellular Endocrinology. Nov. 5, 2013; 380(1-2):41-54. 14 pages.
Langlais et al. "The Stat3/GR Interaction Code: Predictive Value of Direct/Indirect DNA Recruitment for Transcriptior Outcome" Molecular Cell. Jul. 13, 2012; 47(1):38-49.
Hua et al. "Glucocorticoid-induced tethered transrepression requires SUMOylation of GR and formation of a SUMO-SMRT/NCoR1-HDAC3 repressing complex." Proc Natl Acad Sci U S A. Feb. 2, 2016; 113(5):E635-43.
Baiula et al. "Mapracorat, a selective glucocorticoid receptor agonist, causes apoptosis of eosinophils infiltrating the conjunctiva in late-phase experimental ocular allergy." Drug Design, Development and Therapy. Jun. 10, 2014; 8:745-57.
Schäcke et al. "Characterization of ZK 245186, a novel, selective glucocorticoid receptor agonist for the topical treatment of inflammatory skin diseases." British Journal of Pharmacology. Oct. 2009; 158(4):1088-103.
De Bosscher et al. "A fully dissociated compound of plant origin for inflammatory gene repression." Proc Natl Acad Sci U S A. Nov. 1, 2005; 102(44):15827-32.
Schäcke et al. "Dissociation of transactivation from transrepression by a selective glucocorticoid receptor agonist leads to separation of therapeutic effects from side effects." Proc Natl Acad Sci U S A. Jan. 6, 2004; 101(1):227-32.
Coghlan et al. "A Novel Antiinflammatory Maintains Glucocorticoid Efficacy with Reduced Side Effects." Molecular Endocrinology. May 2003; 17(5):860-9.
Van Lierop et al. "Org 214007-0: A Novel Non-Steroidal Selective Glucocorticoid Receptor Modulator with Full Anti-Inflammatory Properties and Improved Therapeutic Index." PLoS One. 2012; 7(11):e48385. 15 pages.
Ripa et al. "Discovery of a Novel Oral Glucocorticoid Receptor Modulator (AZD9567) with Improved Side Effect Profile." J Med Chem. Mar. 8, 2018; 61(5):1785-1799.
Barker et al. "Design and Synthesis of New Nonsteroidal Glucocorticoid Modulators through Application of an Agreement Docking Method". J Med Chem. Jul. 14, 2005; 48(14):4507-10.
Foster et al. "Deuterium Isotope Effects in the Metabolism of Drugs and Xenobiotics: Implications for Drug Design." Advances in Drug Research. Jan. 1, 1985; 14:1-40.
Barker et al. "Dissociated Nonsteroidal Glucocorticoid Receptor Modulators; Discovery of the Agonist Trigger in a Tetrahydronaphthalene-Benzoxazine Series." J Med Chem. Jul. 13, 2006; 49(14):4216-31.
Betageri et al. "Trifluoromethyl group as a pharmacophore: Effect of replacing a CF3 group on binding and agonist activity of a glucocorticoid receptor ligand." Bioorg Med Chem Lett. Nov. 1, 2005; 15(21):4761-9.
Dyck et al. "Effects of Deuterium Substitution on the Catabolism of Beta-Phenylethylamine: An In Vivo Study." J Neurochem. Feb. 1986; 46(2):399-404.
Aranha et al. "Bile acid levels are increased in the liver of patients with steatohepatitis." European Journal of Gastroenterology & Hepatology. Jun. 2008; 20(6):519-25.
Baida et al. "REDD1 functions at the crossroads between the therapeutic and adverse effects of topical glucocorticoids." EMBO Molecular Medicine. Jan. 2015; 7(1):42-58.
Belvisi et al. "Therapeutic Benefit of a Dissociated Glucocorticoid and the Relevance of In Vitro Separation of Transrepression from Transactivation activity." J Immunol. Feb. 1, 2001; 166(3):1975-82.
Britto et al. "REDD1 deletion prevents dexamethasone-induced skeletal muscle atrophy." Am J Physiol Endocrinol Metab. Dec. 1, 2014; 307(11):E983-93.
Canalis. "Mechanisms of glucocorticoid-induced osteoporosis." Current Opinion in Rheumatology. Jul. 2003; 15 (4):454-7.

(56) References Cited

OTHER PUBLICATIONS

Carryer et al. "The effect of cortisone of bronchial asthma and hay fever occurring in subjects sensitive to ragweed pollen." The Journal of Allergy. Jul. 1950; 21(4):282-7.
Cavet et al. "Mapracorat, a novel selective glucocorticoid receptor agonist, inhibits hyperosmolar-induced cytokine release and MAPK pathways in human corneal epithelial cells." Molecular Vision. Sep. 2, 2010; 16:1791-800.
Clore et al. "Glucocorticoid-induced hyperglycemia." Endocrine Practice. Jul.-Aug. 2009; 15(5):469-74.
Curtis et al. "Population-Based Assessment of Adverse Events Associated With Long-Term Glucocorticoid Use." Arthritis & Rheumatism. Jun. 15, 2006; 55(3):420-6.
Geboes et al. "Proinflammatory Role of the Th17 Cytokine Interleukin-22 in Collagen-Induced Arthritis in C57BL/6 Mice." Arthritis & Rheumatism. Feb. 2009; 60(2):390-5.
Geer et al. "Mechanisms of Glucocorticoid-Induced Insulin Resistance: Focus on Adipose Tissue Function and Lipid Metabolism." Endocrinol Metab Clin North Am. Mar. 2014; 43(1):75-102.
Gimenes et al. "Beneficial effect of annexin A1 in a model of experimental allergic conjunctivitis." Experimental Eye Research. May 2015; 134:24-32.
Grahnemo et al. "Possible role of lymphocytes in glucocorticoid-induced increase in trabecular bone mineral tensity." Journal of Endocrinology. Jan. 2015; 224(1):97-108.
Inglis et al. "Collagen-induced arthritis in C57BL/6 mice is associated with a robust and sustained T-cell response to type II collagen." Arthritis Research and Therapy. 2007; 9(5):R113. 8 pages.
Kim et al. "Cholesterol-Induced Non-Alcoholic Fatty Liver Disease and Atherosclerosis Aggravated by Systemic Inflammation." PLoS One. Jun. 5, 2014; 9(6):e97841. 11 pages.
Li et al. "Topical vitamin D3 and low-calcemic analogs induce thymic stromal lymphopoietin in mouse keratinocytes and trigger an atopic dermatitis." Proc Natl Acad Sci U S A. Aug. 1, 2006; 103(31):11736-41.

Missen et al. "The glucocorticoid receptor inhibits NFkappaB by interfering with serine-2 phosphorylation of the RNA polymerase II carboxy-terminal domain." Genes & Development. Sep. 15, 2000; 14(18):2314-29.
Oray et al. "Long-term side effects of glucocorticoids." Expert Opinion on Drug Safety. 2016; 15(4):457-65. 30 pages.
Pearlman et al. "Comparative efficacy and safety of twice daily fluticasone propionate powder versus placebo in the treatment of moderate asthma." Annals of Allergy, Asthma & Immunology. Apr. 1997; 78(4):356-62.
Pereira et al. "Glucocorticoid-induced osteoporosis in rheumatic diseases." Clinics (Sao Paulo). 2010; 65 (11):1197-205.
Schoepe et al. "Glucocorticoid therapy-induced skin atrophy." Experimental Dermatology. Jun. 2006; 15(6):406-20.
Shafiee et al. "In Vivo Ocular Efficacy Profile of Mapracorat, a Novel Selective Glucocorticoid Receptor Agonist, in Rabbit Models of Ocular Disease." Invest Ophthalmol Vis Sci. Mar. 14, 2011; 52(3):1422-30.
Ussar et al. "Loss of Kindlin-1 Causes Skin Atrophy and Lethal Neonatal Intestinal Epithelial Dysfunction." PLoS Genetics. Dec. 2008; 4(12):e1000289. 12 pages.
Vayssière et al. "Synthetic Glucocorticoids That Dissociate Transactivation and AP-1 Transrepression Exhibit Antiinflammatory Activity In Vivo." Mol Endocrinol. Aug. 1997; 11(9):1245-55.
Vinter et al. "Aldara®-induced skin inflammation—studies of psoriasis patients." British Journal of Dermatology. Feb. 2015; 172(2):345-53. 18 pages.
Yang-Yen et al. "Transcriptional Interference between c-Jun and the Glucocorticoid Receptor: Mutual Inhibition of DNA Binding Due to Direct Protein-Protein Interaction." Cell. Sep. 21, 1990; 62(6):1205-15.
Zheng et al. "WNT16 Influences Bone Mineral Density, Cortical Bone Thickness, Bone Strength, and Osteoporotic Fracture Risk." PLoS Genetics. Jul. 2012; 8(7):e1002745. 13 pages.

* cited by examiner

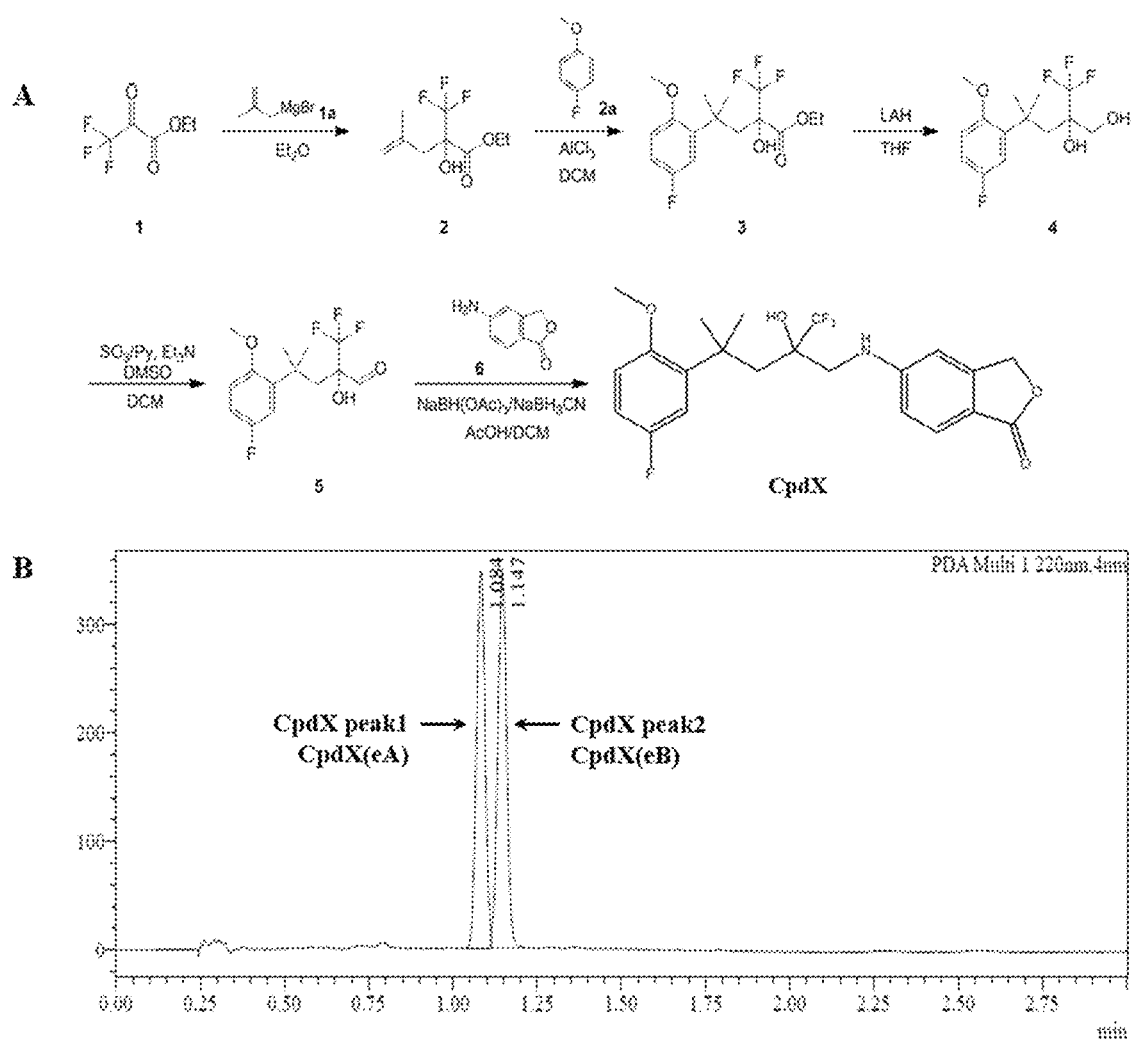
FIG. 2A-B

C 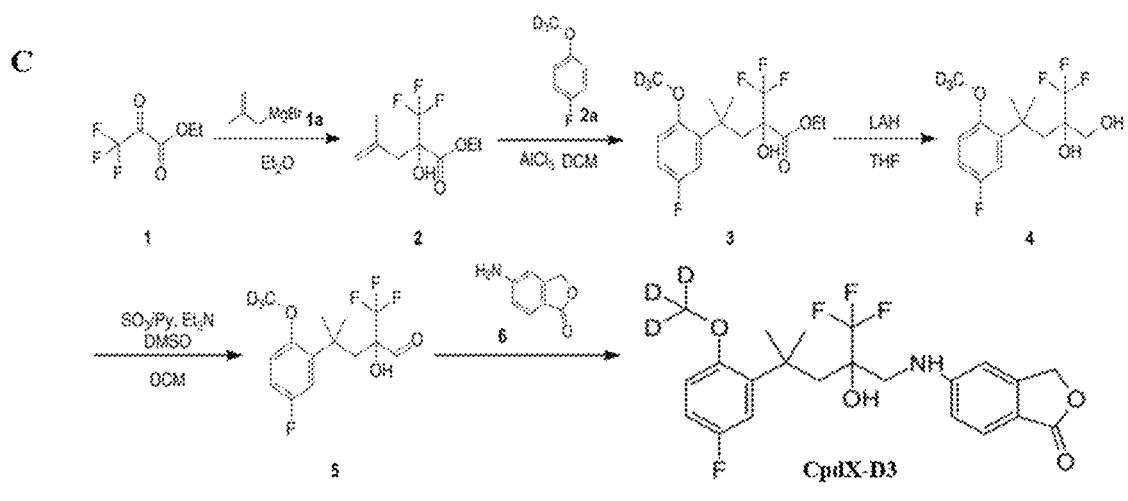
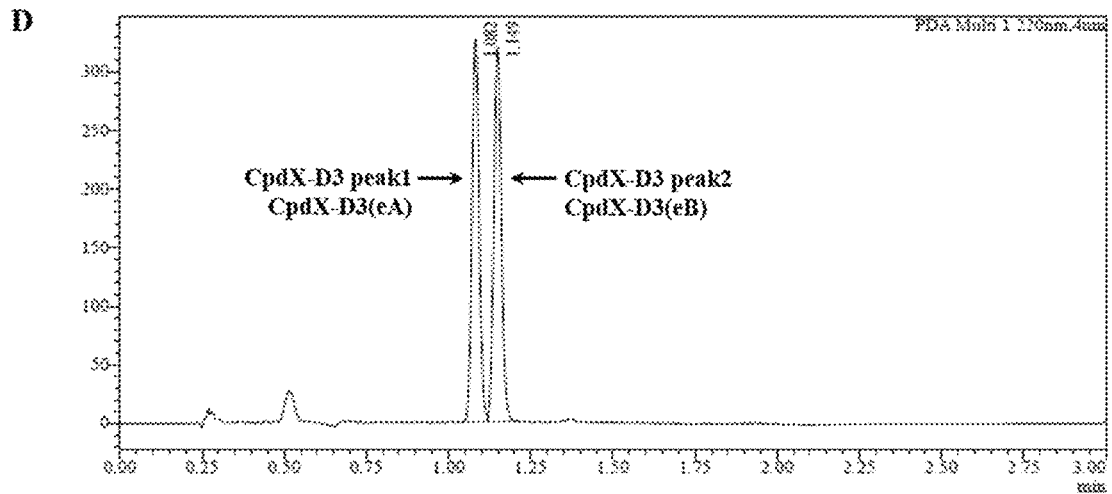
FIG. 2C-D

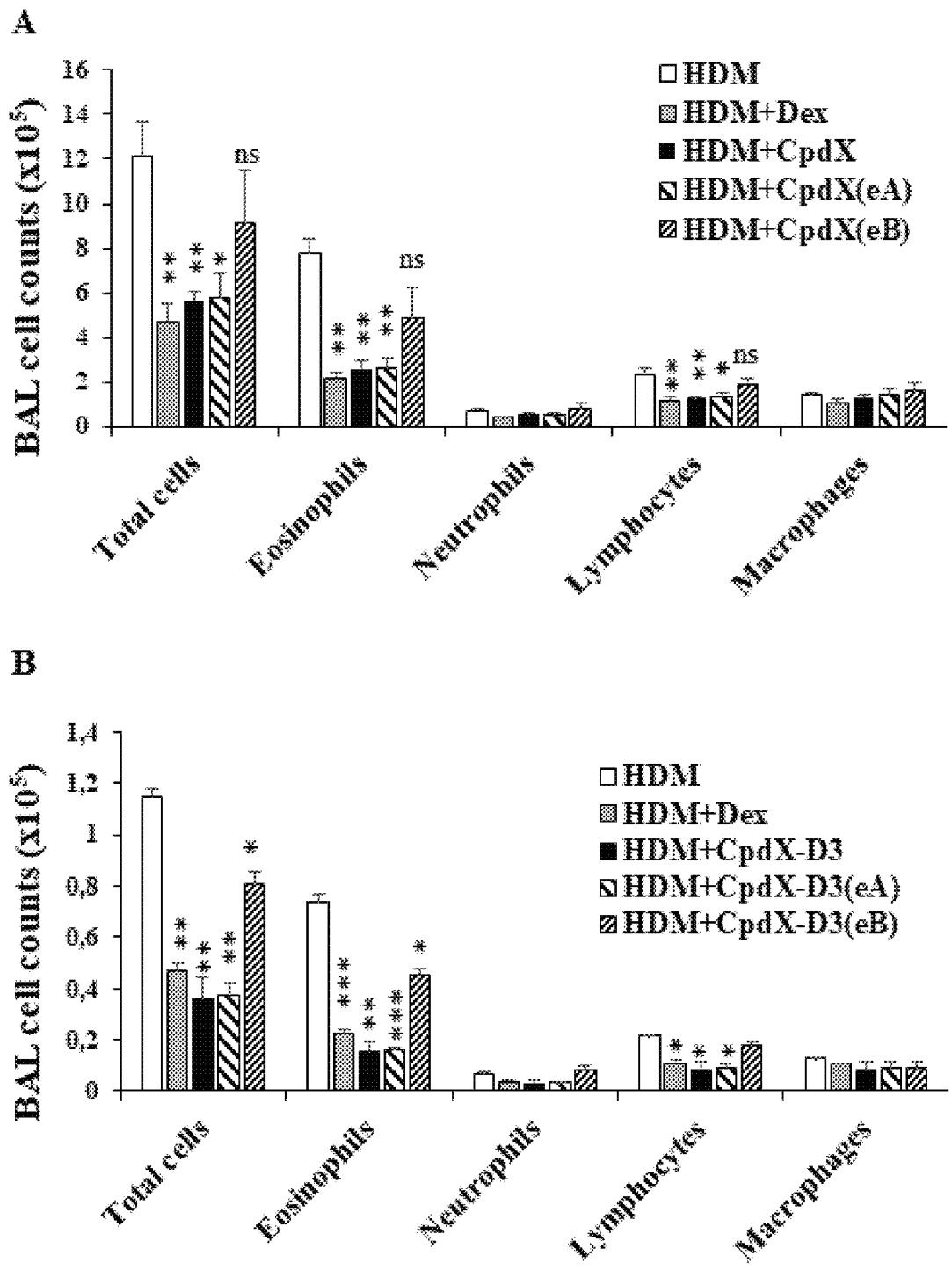
FIG. 11A-B

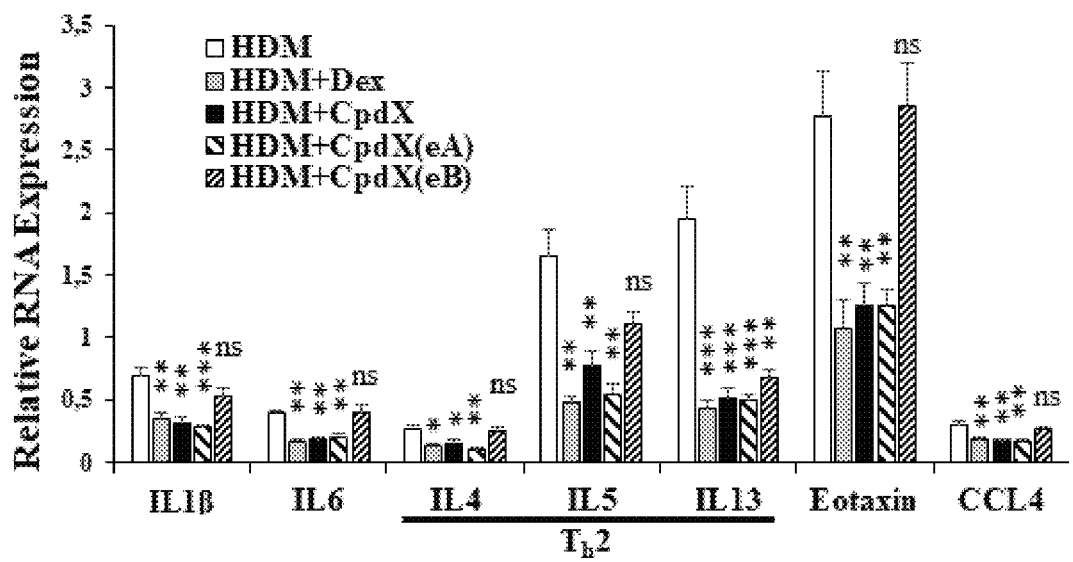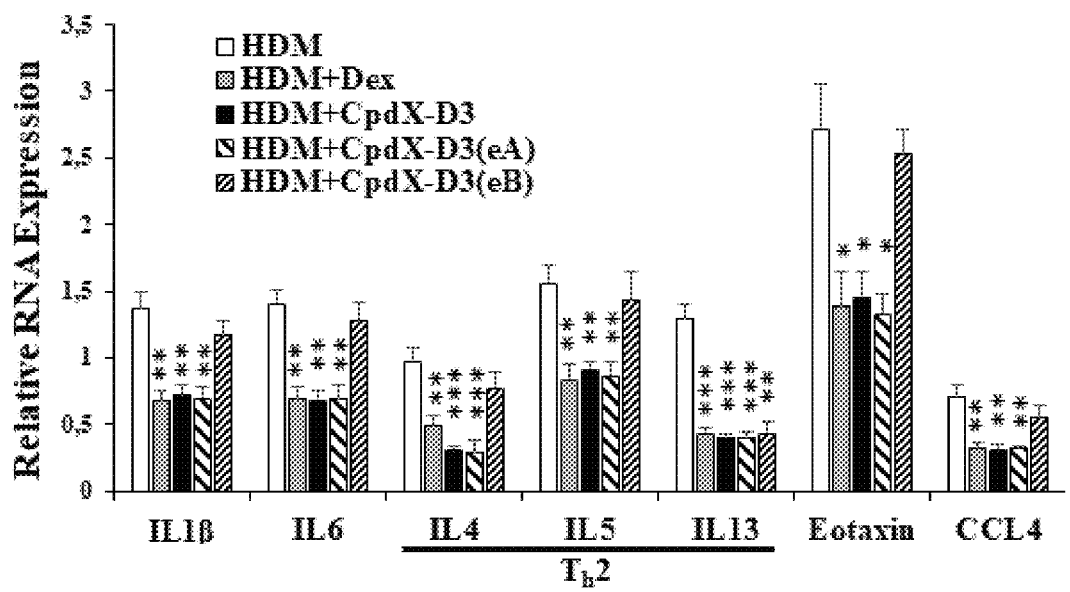
FIG. 11C-D

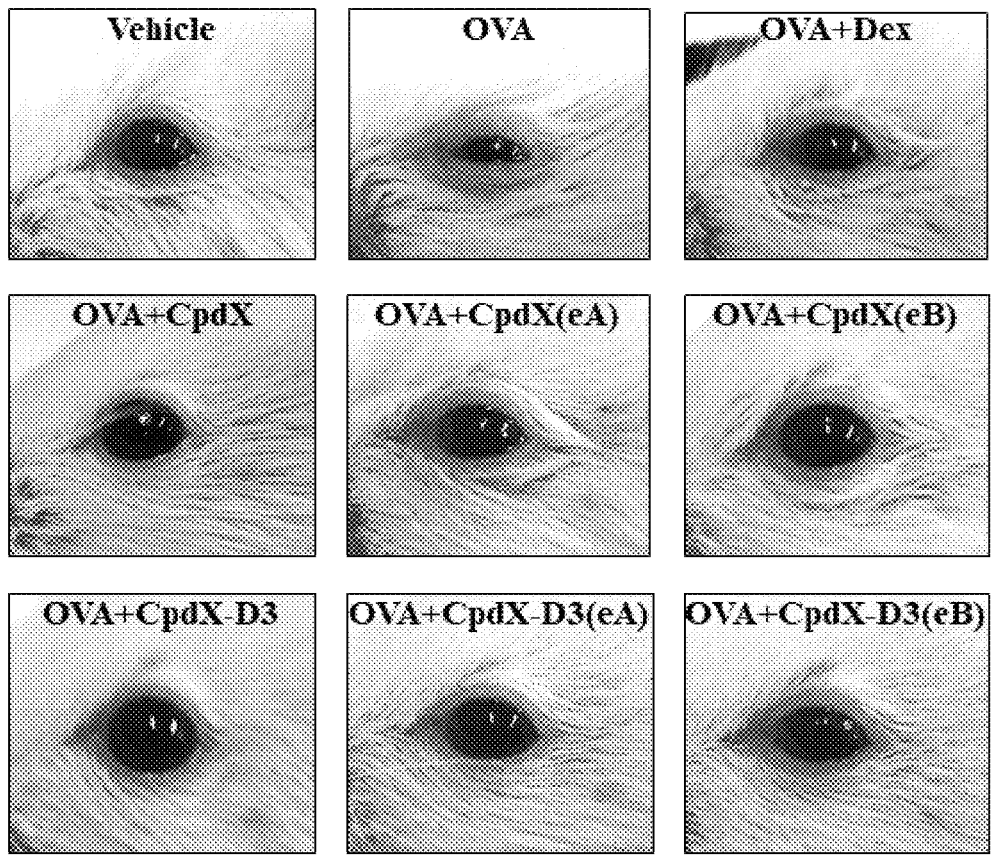
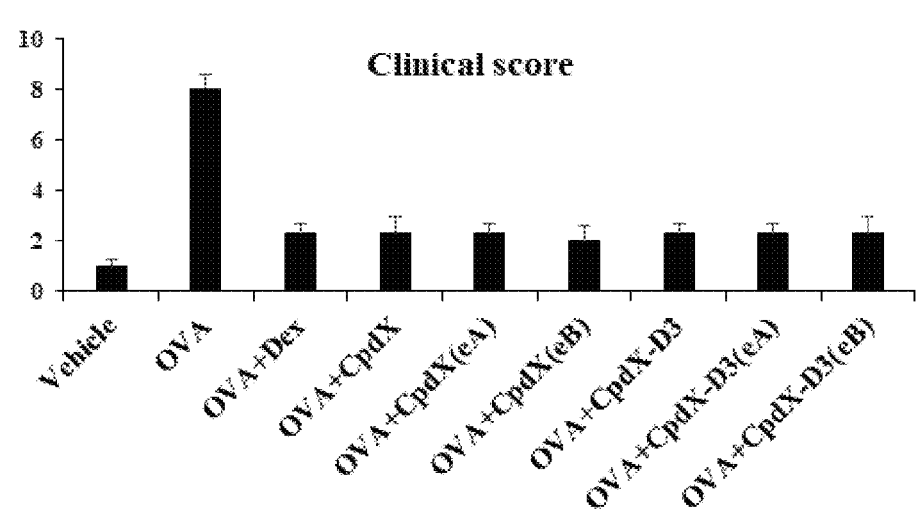
FIG. 21

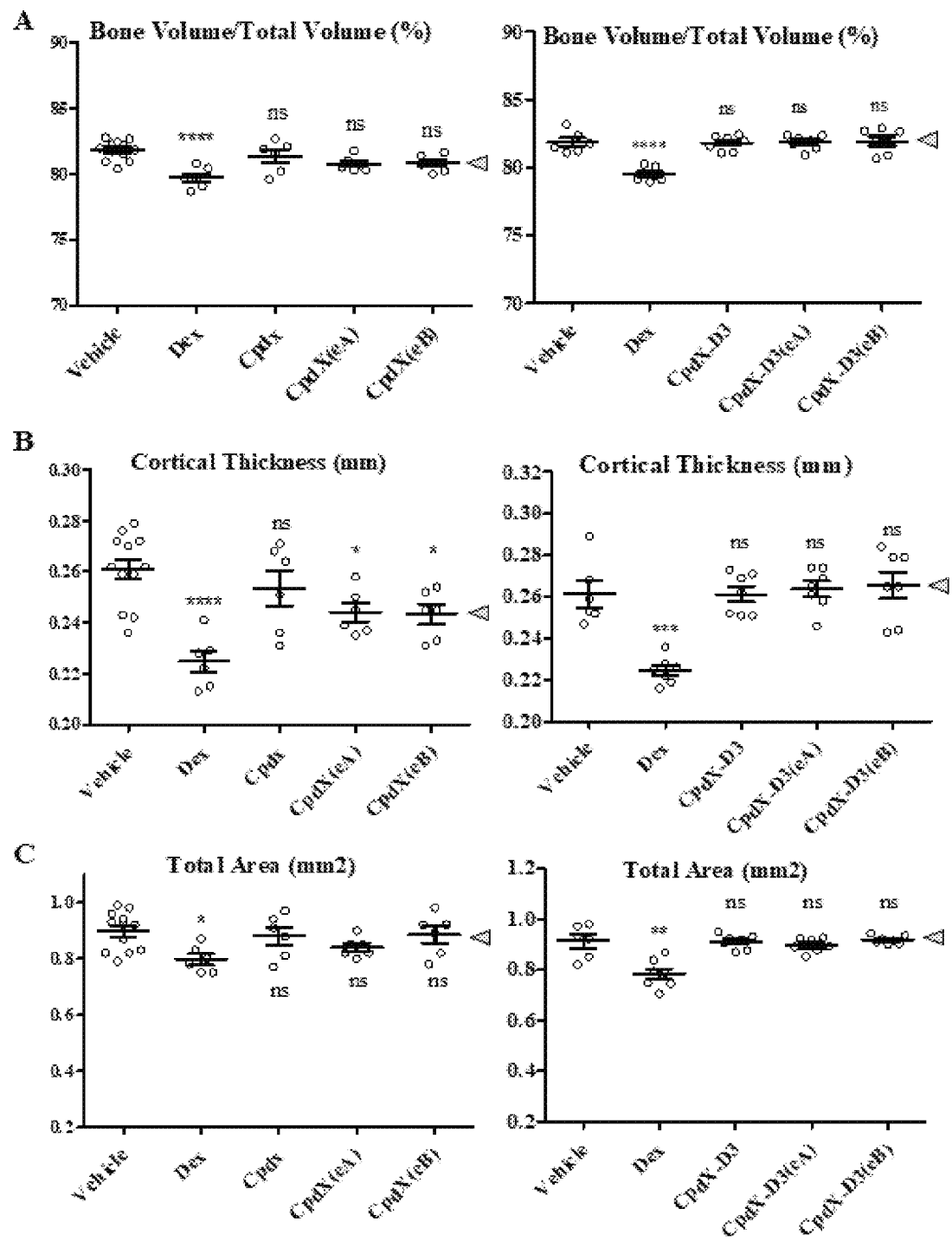
FIG. 25A-C

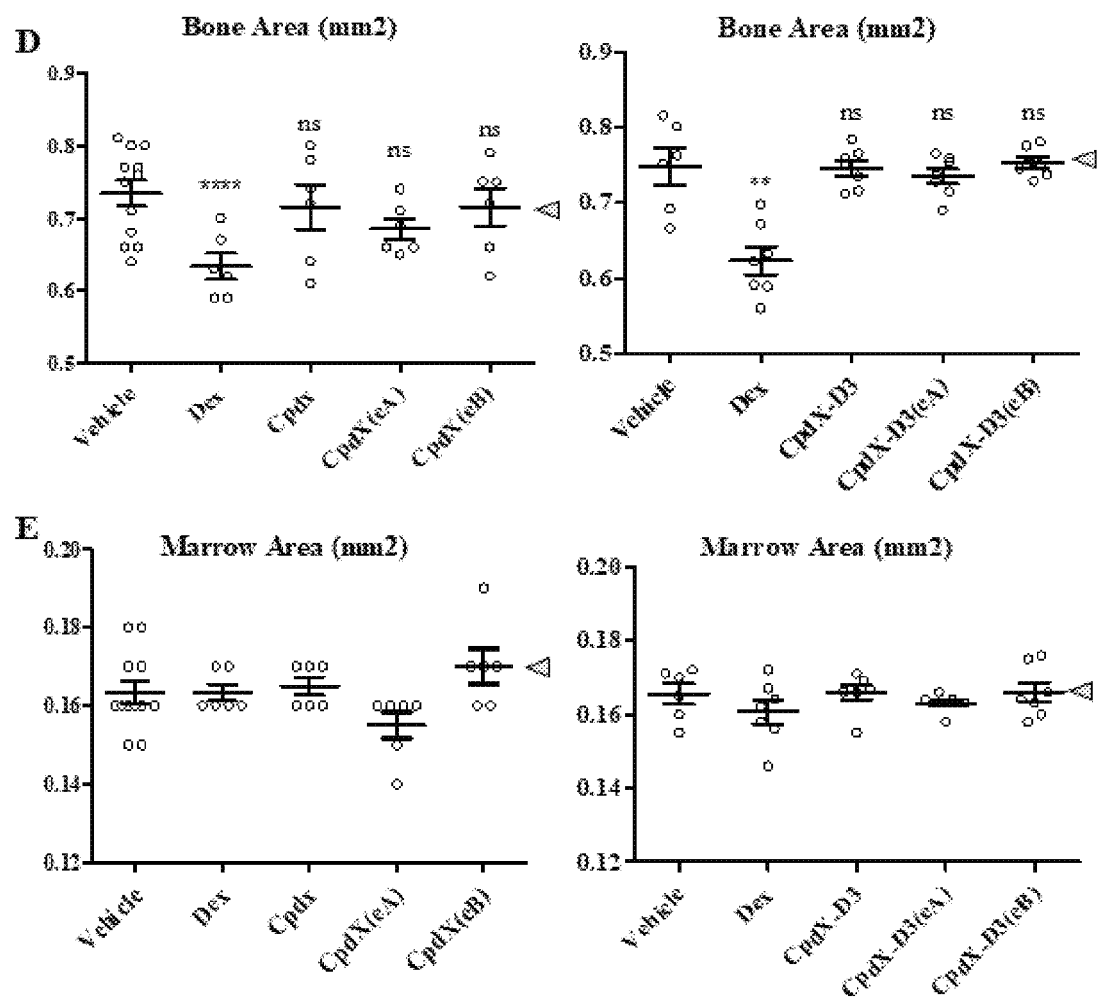
FIG. 25D-E

NON-STEROIDAL SELECTIVE GLUCOCORTICOID RECEPTOR AGONISTIC MODULATORS (SEGRAMS) AND USES THEREOF

FIELD

The present invention relates to SElective Glucocorticoid Receptor Agonistic Modulators (SEGRAMs) for use in the prevention or treatment of an inflammatory disorder in a subject in need thereof. In particular, the SEGRAMs of the present invention do not induce neither the direct transactivation nor the direct transrepression functions of the glucocorticoid receptor, and do not exert the debilitating effects of synthetic glucocorticoids (GC).

BACKGROUND

Glucocorticoids (GCs) are primary stress hormones necessary for life that regulate numerous physiological processes in an effort to maintain homeostasis. They belong to the class of corticosteroids, which bind to their cognate receptor, the glucocorticoid receptor (GR).

GR, also known as NR3C1 (nuclear receptor subfamily 3, group C, member 1), is ubiquitous among almost every vertebrate, in almost every cell. It regulates the expression of genes controlling various important physiological processes, such as development, metabolism and immune response.

Structurally, GR is a modular protein composed of several domains:
- an N-terminal transactivation domain (NTD, or "A/B domain");
- a central DNA-binding domain (DBD, or "C domain"). This domain is the most conserved domain across the nuclear receptor superfamily and contains two zinc finger motifs that recognize and bind target DNA sequences, called glucocorticoid-responsive elements (GREs);
- a flexible hinge region (or "D domain");
- a C-terminal ligand binding domain (LBD, or "E domain"). This domain forms a hydrophobic pocket for binding GCs;
- and a C-terminal domain (CTD or "F domain").

Upon binding of a GC to the GR LBD, the GR undergoes a conformational change resulting in the exposition of two nuclear localization signals located at the DBD/hinge region junction and within the LBD, respectively. GR is then rapidly translocated into the nucleus through nuclear pores, where it can exert one of the three transcriptional regulatory functions detailed hereafter and on FIG. 1.

The first one, called "direct transactivation", is a consequence of binding of GC-associated GR directly to cis-acting positive GREs ((+)GREs), thereby activating the expression of target genes. The consensus (+)GRE sequence, GGAACANNNTGTTCT (with N being any of A, T, C or G) (SEQ ID NO: 1), is an imperfect palindrome comprising two 6-base pair half sites separated by 3 base pairs, hence termed "IR3" (for "inverted repeat 3").

The second function is "indirect tethered transrepression", which arises from the physical interaction of GC-bound GRs with the proinflammatory transcription factors AP-1 and NF-κB. Through binding to the Jun subunit of AP-1 and the p65 subunit of NF-κB, GR antagonizes their activity and interferes with the transcriptional activation function of these two proteins (Nissen and Yamamoto, 2000. *Genes Dev.* 14(18):2314-29; Yang-Yen et al., 1990. *Cell.* 62(6):1205-15).

The third function, called "direct transrepression", is a consequence of GC-associated GR binding directly to the recently (2011) described negative GRE (nGRE) (Surjit et al., 2011. *Cell.* 145(2):224-41), which mediates the direct repression of specific genes. The consensus nGRE sequence, $CTCC(N)_{0-2}GGAGA$ (with N being any of A, T, C or G) (SEQ ID NO: 2), is also palindromic, but differs from the classic (+)GRE in sequence and spacer length (and is therefore named IR0, IR1 or IR2, as the case may be).

The anti-inflammatory properties of natural GCs were demonstrated more than 60 years ago (Carryer et al., 1950. *J Allergy.* 21(4):282-7). Since then, synthetic GCs derivatives have been widely used in treatments aimed at suppressing or alleviating acute and chronic inflammatory and allergic disorders in various diseases. However, GCs treatments are associated with a variety of serious debilitating side effects (Oray et al., 2016. *Expert Opin Drug Saf.* 15(4):457-65), such as type 2 diabetes, dyslipidemia, weight gain, cognitive impairment, gastritis, hepatic steatosis, osteoporosis, hypertension, ischemic heart disease, dermatoporosis, skin atrophy, cataract, glaucoma, mydriasis or suppression of cell-mediated immunity. Different side effects may occur in up to 90% of patients who take GCs for more than 60 days, regardless of the dose and route of administration. Some of these side effects may even occur in patients taking low (≤7.5 mg/day) dosages (Curtis et al., 2006. *Arthritis Rheum.* 55(3):420-6; Pereira et al., 2010. *Clinics (Sao Paulo).* 65(11):1197-1205).

Before the discovery of the direct transrepression pathway in 2011, beneficial anti-inflammatory effects of GCs had been ascribed to the indirect tethered transrepression pathway, while many of the undesirable side effects arising from GC treatments were thought to be related only to the direct transactivation pathway (Clark and Belvisi, 2012. *Pharmacol Ther.* 134(1):54-67) (FIG. 1).

Intense efforts have therefore been made over the past decades to develop novel GR ligands, termed "dissociated" or "SElective" GR Agonistic Modulators (SEGRAMs), that would retain a transrepression profile, while having lost partially or, most ideally, entirely, their transactivation properties (Schäcke et al., 2004. *Proc Natl Acad Sci USA.* 101(1):227-32).

In this regard, a number of putative SEGRAMs have been developed, but few have made it to clinical trials. Such a ligand, RU24858, was found to exhibit such an expected dissociated profile in vitro (Vayssière et al., 1997. *Mol Endocrinol.* 11(9):1245-55). However, upon administration in vivo, pathophysiological studies failed to confirm this dissociation (Belvisi et al., 2001. *J. Immunol.* 166(3):1975-82).

Later, another synthetic non-steroidal ligand, namely Mapracorat (also named ZK245186 or BOL-303242-X), has been shown in vitro to act as an anti-inflammatory agent in corneal epithelial cells challenged with osmotic stress (Cavet et al., 2010. *Mol Vis.* 16:1791-1800), and in vivo in experimental models of dry eye and postoperative inflammation (Shafiee et al., 2011. *Invest Ophthalmol Vis Sci.* 52(3):1422-30), with an activity comparable to that of the synthetic "traditional" steroid dexamethasone, but reduced side effects in intraocular pressure and body weight. Mapracorat has also been the study product of several clinical trials between June 2009 and July 2013: a dose finding phase II clinical trial as an ointment for atopic dermatitis (Clinical trial numbers NCT00944632, NCT01228513, NCT01359787, NCT01407510, NCT01408511 and NCT01736462); and phase I, II and III clinical trials as an ophthalmic suspension for allergic conjunctivitis (Clinical trial number NCT01289431) and inflammation and pain following cataract surgery (Clinical trial numbers NCT00905450, NCT01230125, NCT01298752, NCT01591161, NCT01591655 and NCT01736462). However, as of October 2018, no study results of these trials are available and no marketing authorization has been granted, suggesting that Mapracorat might have revealed problems of efficacy and/or side effects.

As in 2011, the GC-bound GR-mediated direct transrepression function was also shown to be involved in undesirable side effects (Surjit et al., 2011. *Cell*. 145(2):224-41), it appeared that targeting exclusively the indirect tethered transrepression pathway would be efficient in preventing side effects.

There remained thus a need for the development of bona fide SEGRAMs which cannot induce efficiently neither the direct transactivation nor the direct transrepression functions of GR, while still inducing its indirect tethered transrepression activity and anti-inflammatory properties in vivo.

Interestingly, in the late 1990's, Schering AG, now Bayer HealthCare Pharmaceuticals, developed novel nonsteroidal compounds (see, e.g., U.S. Pat. No. 6,245,804), claiming an anti-inflammatory activity dissociated from their metabolic effects, (see, e.g., U.S. Pat. No. 6,323,199). By 2016, the Applicant discovered that among these compounds, one of them namely 5-[4-(5-fluoro-2-methoxyphenyl)-2-hydroxy-4-methyl-2-(trifluoromethyl)pentylamino]isobenzofuran-1 (3H)-one, hereafter named "CpdX", does not induce the transactivation and direct transrepression functions of the GR, while still inducing its indirect tethered transrepression activity (Hua et al., 2016. *Proc Natl Acad Sci USA*. 113(5): E635-43).

Herein, the Inventors show that, contrary to the putative SEGRAMs previously described in the art (such as Mapracorat), CpdX selectively induces the GR "indirect tethered transrepression activity", being thus a bona fide SEGRAM selectively exhibiting the GR indirect transrepression function, whereas Mapracorat exhibits all three GR functions. Most importantly, the Inventors demonstrate that, upon long-term administration to mice, CpdX and novel derivatives thereof are therapeutically as effective as the synthetic glucocorticoid Dexamethasone (Dex), while being devoid of the well-established debilitating side-effects of synthetic glucocorticoids.

SUMMARY

The present invention relates to a SElective Glucocorticoid Receptor Agonistic Modulator (SEGRAM) of Formula 1 (CpdX) or a derivative thereof:

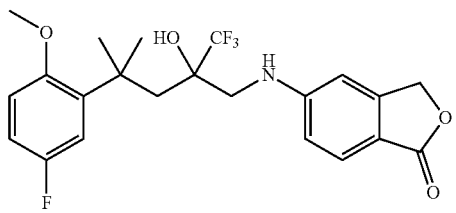

(Formula 1-CpdX)

or a pharmaceutically acceptable salt, solvate and/or prodrug thereof, for use in the prevention or treatment of an inflammatory disorder in a subject in need thereof.

In one embodiment, the SEGRAM of Formula 1 or a derivative thereof is in a deuterated form, preferably the SEGRAM is a compound of Formula 2 (CpdX-D3):

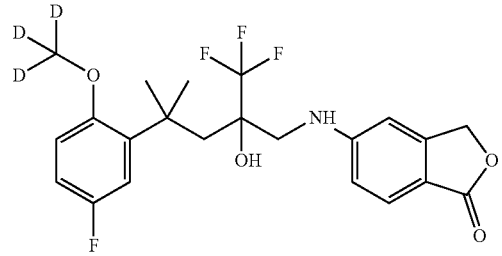

(Formula 2-CpdX-D3)

In one embodiment, the SEGRAM is in a racemic form, or is one of its two enantiomer forms.

In one embodiment, a derivative of the SEGRAM of Formula 1 is a compound of Formula 3:

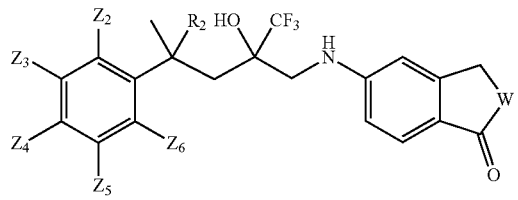

(Formula 3)

wherein:
W is selected from O, S or $CH_2$,
$R_2$ is selected from H or $CH_3$, and
$Z_2$, $Z_3$, $Z_4$, $Z_5$ and $Z_6$ are each independently selected from H, F, Cl, Br, $CH_3$, $OCH_3$, $CH_2CH_3$, $CH_2CH_2CH_3$, $CH(CH_3)_2$, $C(CH_3)_3$, $COCH_3$, $NO_2$, CN, CH=$CH_2$ or $CONH_2$.

In one embodiment, the SEGRAM of Formula 1 or a derivative thereof does not induce or does not substantially induce neither a direct transactivation function nor a direct transrepression function of the glucocorticoid receptor.

In one embodiment, the SEGRAM of Formula 1 or a derivative thereof does not induce or does not substantially induce steroidal anti-inflammatory drugs (SAIDs)-associated side effects upon administration to a subject in need thereof.

In one embodiment, SAIDs-associated side effects are selected from the group comprising skin atrophy; osteoporosis; growth suppression; body weight loss; fat mass gain; lean mass loss; thymus, spleen, kidney and/or adrenal gland apoptosis; corticosterone synthesis inhibition; adrenal suppression; hyperglycemia; insulin resistance; hyperinsulinemia; and fatty liver.

In one embodiment, the inflammatory disorder is characterized by an increased level of at least one secreted cytokine and/or antibody selected from the group comprising IL-1β, IL-2, IL-3, IL-4, IL-5, IL-6, IL-10, IL-12, IL-13, IL-17a, IL-17c, IL-17f, IL-18, IL-21, IL-22, IL-23, IL-33, TSLP, TGFβ, CCL4, TNFα, COX2, MMP13, IgE, IgG1 and IgG2a.

In one embodiment, the inflammatory disorder is selected from the group comprising atopic dermatitis, contact dermatitis, allergic asthma, allergic sinusitis, allergic conjunctivitis, allergic rhinitis, rhinoconjunctivitis, giant-cell arteritis (Horton disease), hay fever, solar dermatitis, eczema, urticaria, angioedema, erythema nodosum, erythema multiforme, cutaneous necrotizing venulitis, insect bite skin inflammation, anaphylaxis, psoriasis, rheumatoid arthritis, inflammatory bowel disease (IBD) (including Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease.

In one embodiment, the inflammatory disorder is selected from the group comprising contact dermatitis, atopic dermatitis, allergic asthma, psoriasis, allergic conjunctivitis, rheumatoid arthritis and ulcerative colitis.

In one embodiment, the inflammatory disorder is selected from the group comprising atopic dermatitis, contact dermatitis, allergic asthma, psoriasis, allergic conjunctivitis, rheumatoid arthritis and ulcerative colitis; and the SEGRAM is an enantiomer of the SEGRAM of Formula 1 or a derivative thereof, said enantiomer corresponding to the first elution peak [CpdX(eA)] of a supercritical fluid chromatography (SFC) of a racemic mixture of the SEGRAM of Formula 1 or a derivative thereof.

In one embodiment, the inflammatory disorder is selected from the group comprising atopic dermatitis, contact dermatitis, psoriasis, allergic conjunctivitis and ulcerative colitis; and the SEGRAM is an enantiomer of the SEGRAM of Formula 1 or a derivative thereof, said enantiomer corresponding to the second elution peak [CpdX(eB)] of a supercritical fluid chromatography (SFC) of a racemic mixture of the SEGRAM of Formula 1 or a derivative thereof.

In one embodiment, the inflammatory disorder is selected from the group comprising atopic dermatitis, contact dermatitis, allergic asthma, psoriasis, allergic conjunctivitis, rheumatoid arthritis and ulcerative colitis; and the SEGRAM is an enantiomer of the SEGRAM of Formula 2 or a derivative thereof, said enantiomer corresponding to the first elution peak [CpdX-D3(eA)] of a supercritical fluid chromatography (SFC) of a racemic mixture of the SEGRAM of Formula 2 or a derivative thereof.

In one embodiment, the inflammatory disorder is selected from the group comprising atopic dermatitis, contact dermatitis, psoriasis, allergic conjunctivitis and ulcerative colitis; and the SEGRAM is an enantiomer of the SEGRAM of Formula 2 or a derivative thereof, said enantiomer corresponding to the second elution peak [CpdX-D3(eB)] of a supercritical fluid chromatography (SFC) of a racemic mixture of the SEGRAM of Formula 2 or a derivative thereof.

The present invention also relates to an enantiomer of a SElective Glucocorticoid Receptor Agonistic Modulator (SEGRAM) of Formula 1, or to a pharmaceutically acceptable salt, solvate and/or prodrug thereof, preferably said enantiomer is CpdX(eA) or CpdX(eB).

In one embodiment, the enantiomer is obtained by separation of a racemic mixture of the compound of Formula 1 or a derivative thereof by supercritical fluid chromatography (SFC), wherein CpdX(eA) corresponds to the first elution peak and CpdX(eB) corresponds to the second elution peak.

The present invention also relates to a deuterated form of a SElective Glucocorticoid Receptor Agonistic Modulator (SEGRAM) of Formula 1, or to a pharmaceutically acceptable salt, solvate and/or prodrug thereof.

In one embodiment, said deuterated form is a compound of Formula 2:

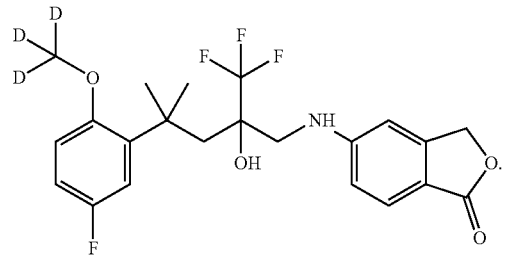

(Formula 2)

In one embodiment, said deuterated form is in a racemic form.

In one embodiment, said deuterated form is either one of the two enantiomers of the compound of Formula 2, preferably said enantiomer is CpdX-D3(eA) or CpdX-D3(eB).

In one embodiment, said deuterated form are obtained by separation of a racemic mixture of the compound of Formula 2 or a derivative thereof by supercritical fluid chromatography (SFC), and wherein CpdX-D3(eA) corresponds to the first elution peak and CpdX-D3(eB) corresponds to the second elution peak.

BRIEF DESCRIPTION OF THE DRAWINGS

FIG. 2 comprises two schemes for the synthesis of either (A) [(R/S)-5[4-(5-fluoro-2-methoxyphenyl)-2-hydroxy-4-methyl-2-(trifluoromethyl)pentylamino]isobenzofuran-1 (3H)-one] [CpdX], or (C) [(R/S)-5-{4-[2-(methoxy-D3)-5-fluorophenyl]-2-hydroxy-4-methyl-2-(trifluoromethyl) pentylamino}isobenzofuran-1(3H)-one] [CpdX-D3]; and two chromatograms showing the separation of the two enantiomers of either (B) [(R/S)-5-[4-(5-fluoro-2-methoxyphenyl)-2-hydroxy-4-methyl-2-(trifluoromethyl)pentylamino]-iso-benzofuran-1(3H)-one] [CpdX], or (D) [(R/S)-5-{4-[2-(methoxy-D3)-5-fluorophenyl]-2-hydroxy-4-methyl-2-(trifluoromethyl)pentylamino}isobenzofuran-1 (3H)-one] [CpdX-D3] through supercritical fluid chromatography (SFC) method.

Figure 4:
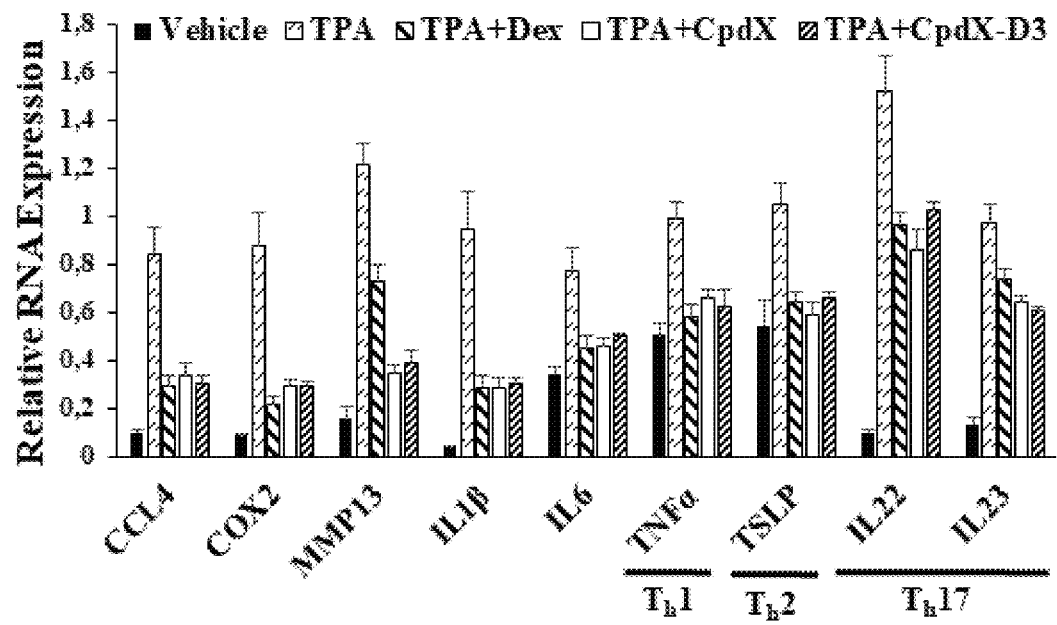

FIG. 4 is a histogram showing the relative RNA expression measured by q-RT-PCR analysis of RNA transcripts of genes encoding macrophage inflammatory protein-1⊕ [CCL4], cyclooxygenase-2 [COX2], collagenase 3 [MMP13], interleukin-1β[IL1β], interleukin-6 [IL6], tumor necrosis factor alpha [TNFα], thymic stromal lymphopoietin [TSLP], interleukin-22 [IL22] and interleukin-23 [IL23]. $T_h1$-, $T_h2$- and $T_h17$-specific pro-inflammatory interleukins are highlighted. RNA transcripts were extracted from mouse ear skin samples after induction of a contact dermatitis-like inflammation by treatment (1 nmole/cm$^2$) with either 12-O-tetradecanoylphorbol-13-acetate alone [TPA], TPA and dexamethasone [TPA+Dex], TPA and (R/S)-5-[4-(5-fluoro-2-methoxyphenyl)-2-hydroxy-4-methyl-2-(trifluoromethyl)pentylamino]isobenzofuran-1 (3H)-one [TPA+CpdX], or TPA and (R/S)-5-{4-[2-(methoxy-D3)-5-fluorophenyl]-2-hydroxy-4-methyl-2-(trifluoromethyl)pentylamino}isobenzofuran-1(3H)-one [TPA+CpdX-D3]. Data are represented as mean±SEM of at least three independent experiments with at least three mice per treatment.

Figure 5:
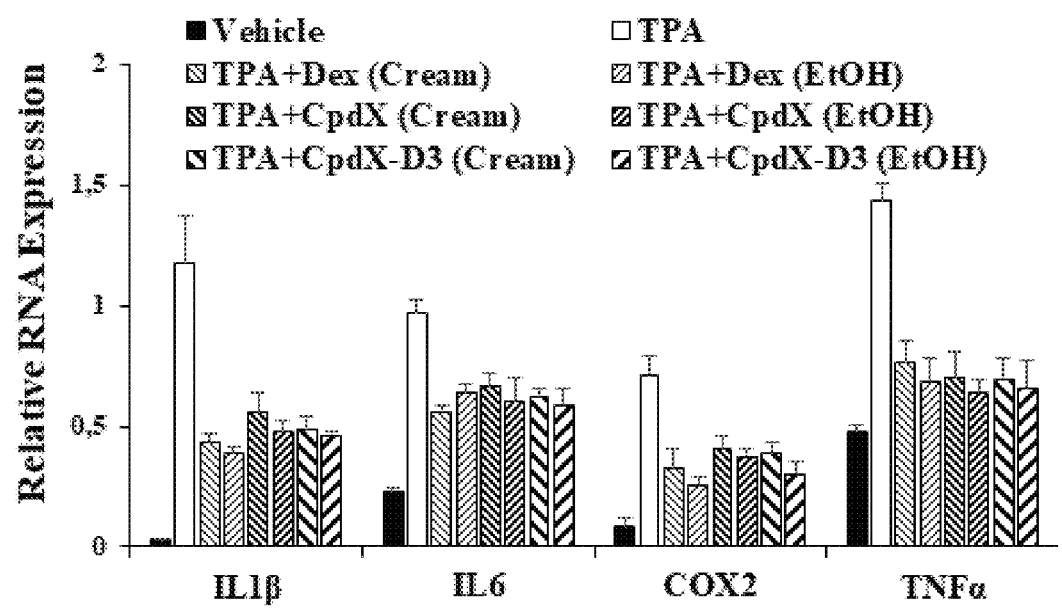

FIG. 5 is a histogram of the relative RNA expression measured by q-RT-PCR analysis of RNA transcripts of genes encoding interleukin-1β [IL1β], interleukin-6 [IL6], cyclooxygenase-2 [COX2] and tumor necrosis factor alpha [TNFα]. RNA transcripts were extracted from mouse ear skin samples as described in FIG. 4. Dexamethasone [Dex], (R/S)-5-[4-(5-fluoro-2-methoxyphenyl)-2-hydroxy-4-methyl-2-(trifluoromethyl)-pentylamino]isobenzofuran-1 (3H)-one [CpdX], as well as (R/S)-5-{4-[2-(methoxy-D3)-5-fluorophenyl]-2-hydroxy-4-methyl-2-(trifluoromethyl) pentylamino}-isobenzofuran-1(3H)-one [CpdX-D3], were administered in either ethanol (EtOH)(1 nmole/cm$^2$) or a Cream (0.05%). Data are represented as mean±SEM of at least three independent experiments with at least three mice per treatment.

Figure 6:
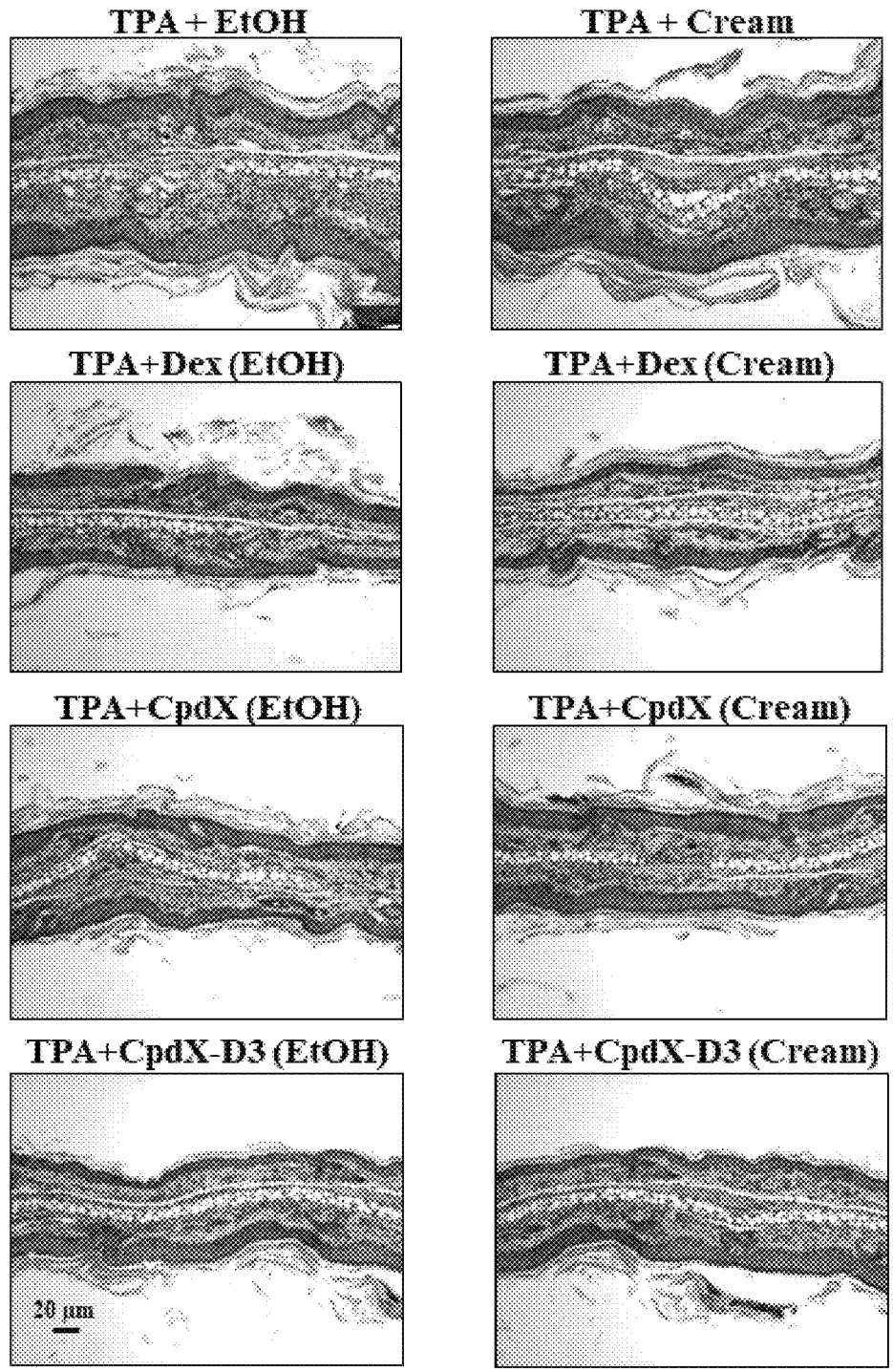

FIG. 6 is a set of eight micrographs showing skin sections of mice as treated in FIG. 5. The mouse ear skin sections were stained with hematoxylin and eosin. Scale bar represents 20 μm.

Figure 7:
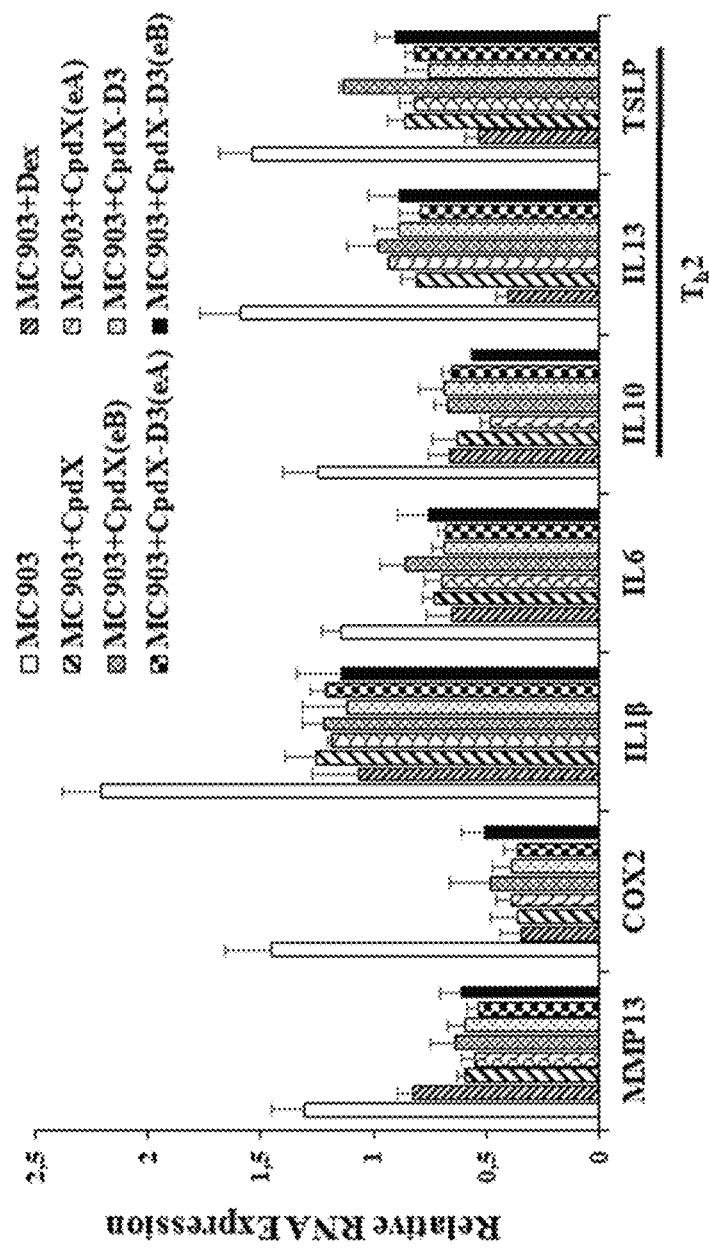

FIG. 7 is a histogram showing the relative RNA expression measured by q-RT-PCR analysis of RNA transcripts of genes encoding collagenase 3[MMP13], cyclooxygenase-2 [COX2], interleukin-1β [IL1β], interleukin-6 [IL6], interleukin-10 [IL10], interleukin-13 [IL13] and thymic stromal lymphopoietin [TSLP1]. $T_h2$-specific pro-inflammatory interleukins are highlighted. RNA transcripts were extracted from mouse ear skin samples after induction of an atopic dermatitis-like inflammation and treatment (1 nmole/cm$^2$) with calcipotriol alone [MC903], calcipotriol and dexamethasone [MC903+Dex], calcipotriol and (R/S)-5-[4-(5-fluoro-2-methoxyphenyl)-2-hydroxy-4-methyl-2-(trifluoromethyl)pentylamino]isobenzofuran-1(3H)-one [MC903+CpdX], calcipotriol and CpdX(eA) [MC903+CpdX(eA)], calcipotriol and CpdX(eB) [MC903+CpdX(eB)], calcipotriol and (R/S)-5-{4-[2-(methoxy-D3)-5-fluorophenyl]-2-hydroxy-4-methyl-2-(trifluoromethyl) pentylamino}isobenzofuran-1(3H)-one [MC903+CpdX-D3], calcipotriol and CpdX-D3(eA) [MC903+CpdX-D3 (eA)] or calcipotriol and CpdX-D3(eB) [MC903+CpdX-D3 (eB)]. Data are represented as mean±SEM of at least three independent experiments with at least three mice per treatment.

Figure 8:
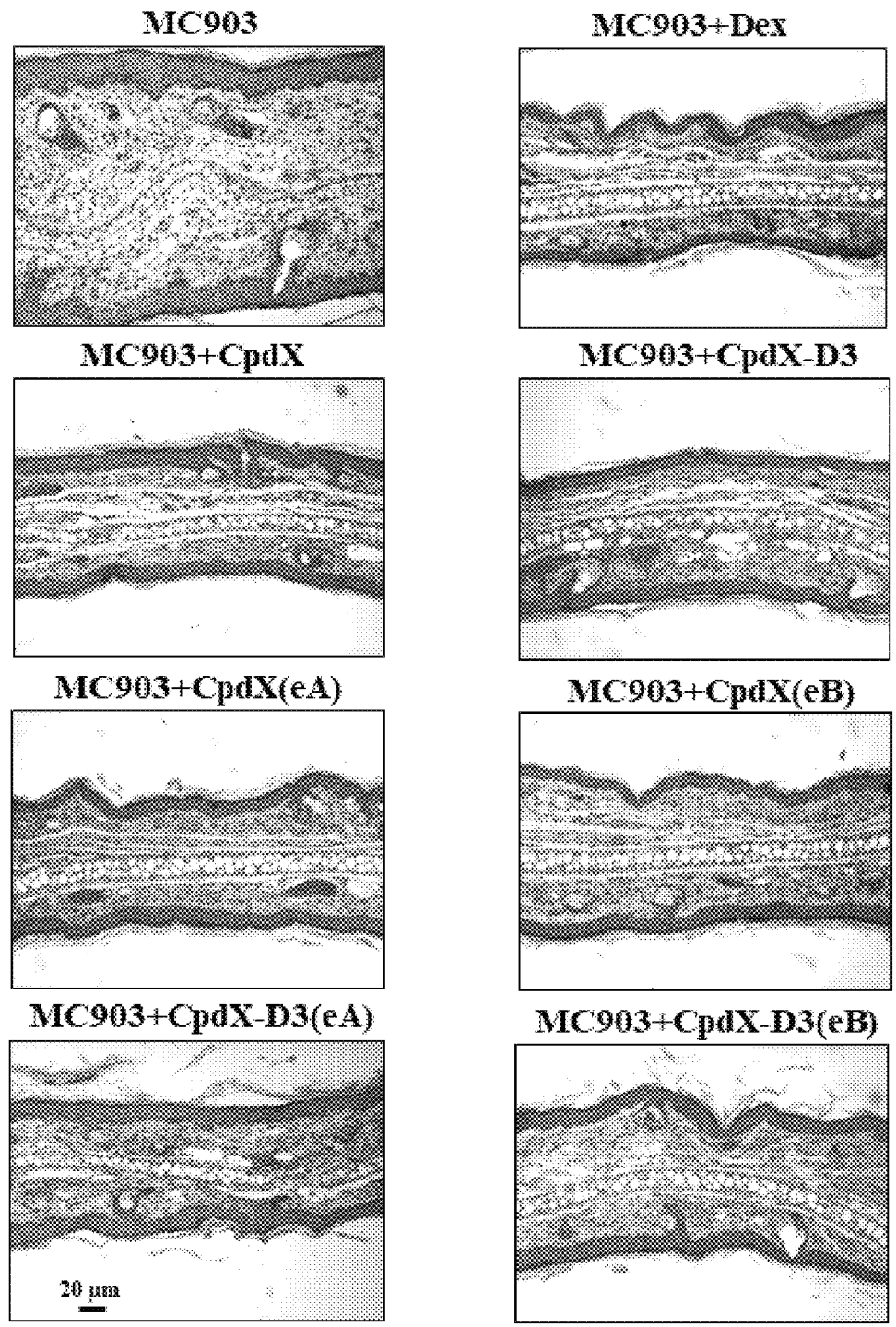

FIG. 8 is a set of eight micrographs showing skin sections of mice treated as in FIG. 7. The mouse ears skin sections were stained with hematoxylin and eosin. Scale bar represents 20 μm.

Figure 9:
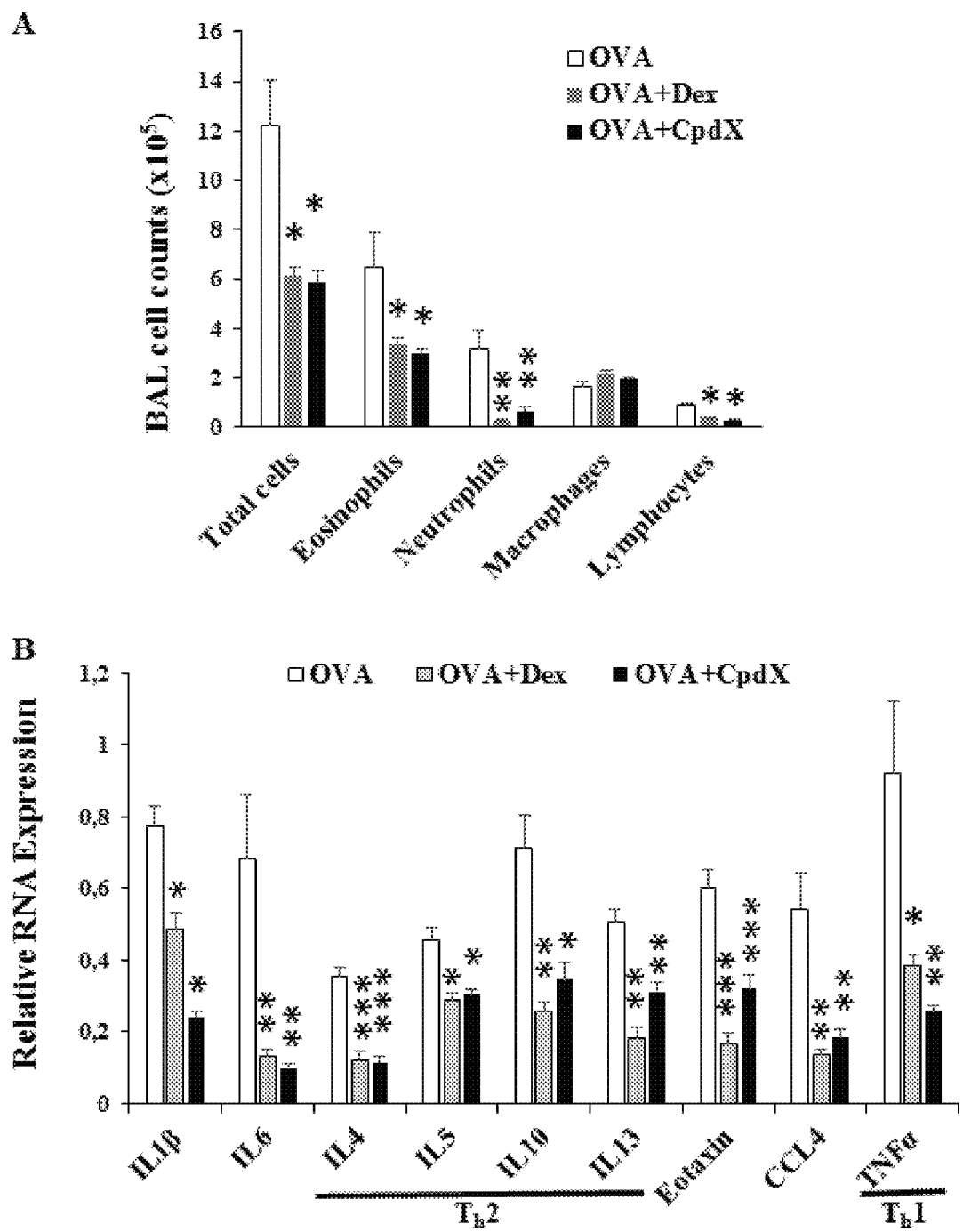

FIG. 9 is a set of two histograms showing (A) the cell counts in a bronchoalveolar lavage [BAL] and (B) the relative RNA expression measured by q-RT-PCR analyses of RNA transcripts extracted from mouse lung samples after a 22-day induction of an asthma-like lung inflammation that includes 18 days of sensitization with ovalbumin (OVA), followed by a 3 day challenge with OVA, either alone [OVA] or together with 1 mg/kg of body weight of dexamethasone [OVA+Dex] or (R/S)-5-[4-(5-fluoro-2-methoxyphenyl)-2-hydroxy-4-methyl-2-(trifluoromethyl)pentylamino]isobenzofuran-1(3H)-one [OVA+CpdX]. (A): the number (×10$^5$) of total cells, eosinophils, neutrophils, macrophages and lymphocytes is reported. (B): the relative RNA expression of the genes encoding interleukin-1β [IL1β], interleukin-6 [IL6], interleukin-4[IL4], interleukin-5 [IL5], interleukin-10 [IL10], interleukin-13 [IL13], eotaxin [Eotaxin], macrophage inflammatory protein-1β [CCL4] and tumor necrosis factor alpha [TNFα] is reported. $T_h2$- and $T_h1$-specific pro-inflammatory interleukins are highlighted. Data are represented as mean±SEM of at least six mice per treatment. The statistical significance compared to the OVA treatment was calculated by student t test; (*) p<0.05; () p<0.01; (*) p<0.001.

Figure 10:
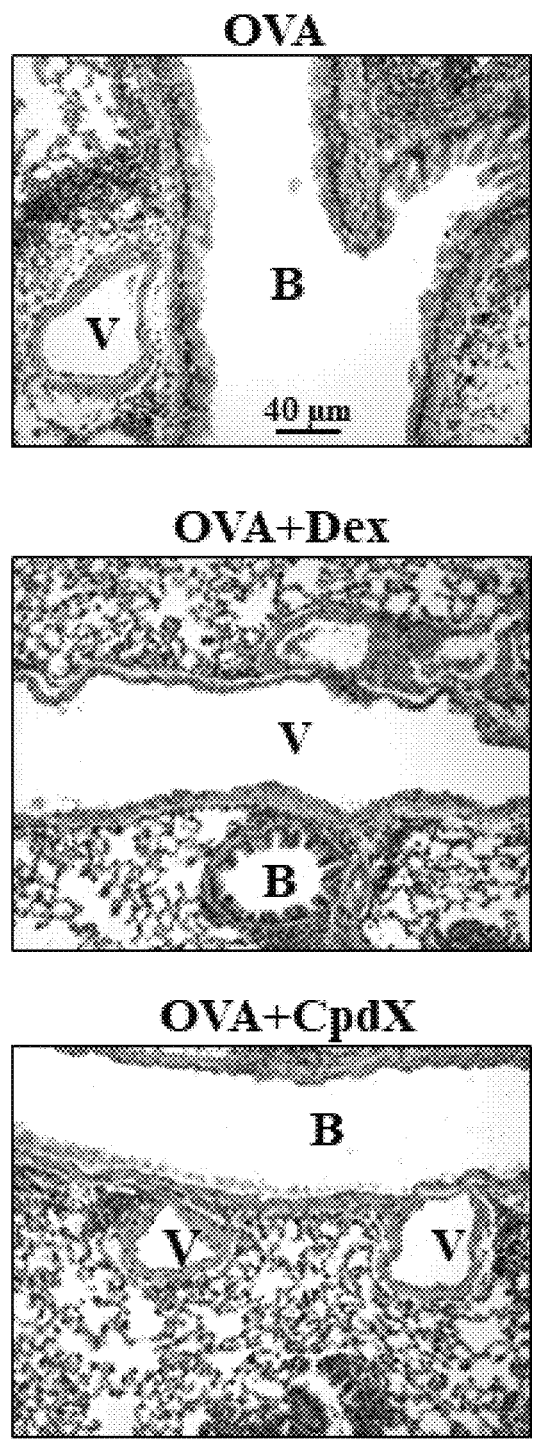

FIG. 10 is a set of three micrographs showing an ovalbumin-induced asthma-like lung inflammation, after 18 days of sensitization with ovalbumin (OVA), followed by a 3-day challenge as described in FIG. 9. Lung sections were stained with hematoxylin and eosin. Peribronchiolar (B) and perivascular (V) regions are indicated. Scale bar represents 40 μm.

FIG. 11 is a set of four histograms showing (A-B) the cell counts in a bronchoalveolar lavage [BAL] and (C-D) the relative RNA expression measured by q-RT-PCR analyses of RNA transcripts extracted from mouse lung samples at D32, after induction of an asthma-like lung inflammation with a 28-day sensitization with house dust mite (HDM), followed by a 3-day HDM challenge, either alone [HDM] or together with either 1 mg/kg of body weight of dexamethasone [HDM+Dex], (R/S)-5-[4-(5-fluoro-2-methoxyphenyl)-2-hydroxy-4-methyl-2-(trifluoromethyl)pentylamino]isobenzofuran-1(3H)-one [HDM+CpdX], CpdX(eA) [HDM+CpdX (eA)], CpdX(eB) [HDM+CpdX(eB)], (R/S)-5-{4-[2-(methoxy-D3)-5-fluorophenyl]-2-hydroxy-4-methyl-2-(trifluoromethyl)penty-lamino}isobenzofuran-1(3H)-one [HDM+CpdX-D3], CpdX-D3(eA) [HDM+CpdX-D3(eA)] or CpdX-D3(eB) [HDM+CpdX-D3(eB)]. (A-B): the number (×10$^5$) of total cells, eosinophils, neutrophils, macrophages and lymphocytes is reported. (C-D): the relative RNA expression of the genes encoding interleukin-1β [IL1β], interleukin-6 [IL6], interleukin-4 [IL4], interleukin-5 [IL5], interleukin-13 [IL13], eotaxin [Eotaxin] and macrophage inflammatory protein-1β[CCL4] is reported. $T_h2$-specific pro-inflammatory interleukins are highlighted. Data are represented as mean±SEM of at least three independent experiments with at least four mice per treatment. The statistical significance compared to the HDM treatment was calculated by student t test; (*) p<0.05; () p<0.01; (*) p<0.001; (ns) not significant.

Figure 12:
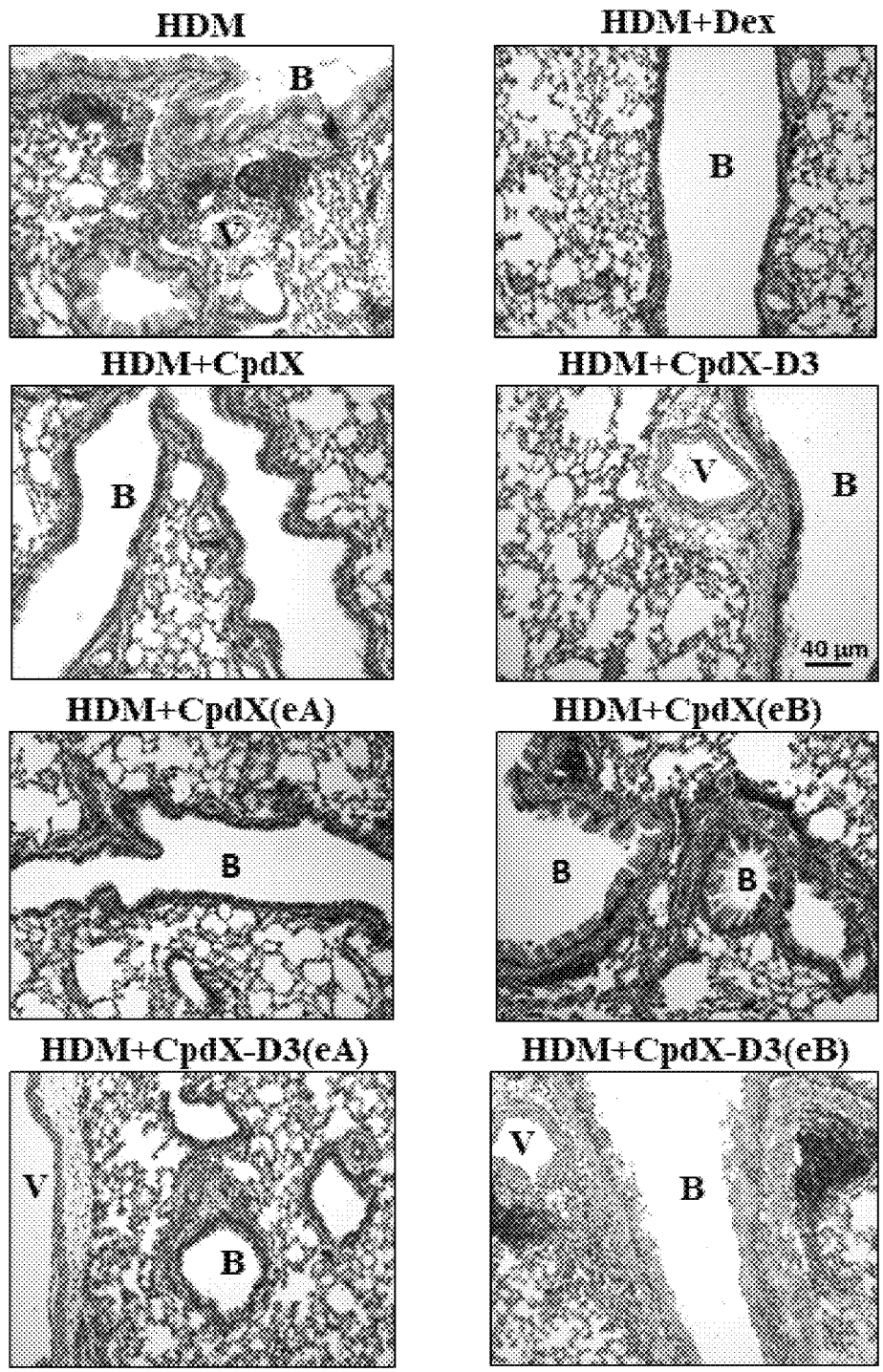

FIG. 12 is a set of eight micrographs showing a house dust mite (HDM)-induced asthma-like lung inflammation, after 28 days of sensitization with HDM, followed by a 3-day challenge as described in FIG. 11. The lung sections were stained with hematoxylin and eosin. Peribronchiolar (B) and perivascular (V) regions are indicated. Scale bar represents 40 µm.

Figure 13:
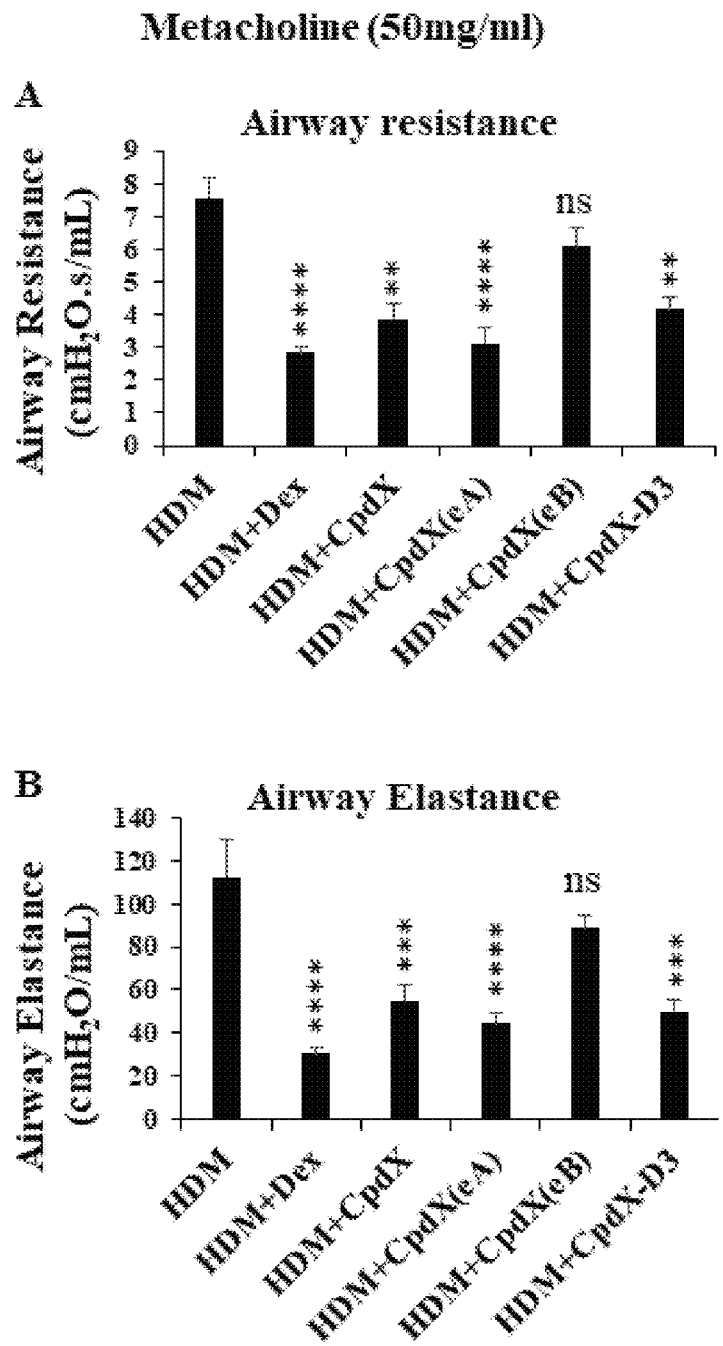

FIG. 13 is a set of two histograms showing the airway hyperresponsiveness to methacholine (MCh, 50 mg/mL) of mice in which a house dust mite (HDM)-induced asthma-like lung inflammation was induced by a 28-day sensitization with HDM, followed by a 3-day challenge as described in FIG. 11. (A) airway resistance, (B) airway elastance. Data are represented as mean±SEM with at least eight mice per treatment. The statistical significance as compared to the HDM treatment on its own was calculated through Two-way ANOVA followed by Bonferroni multiple comparisons; () $p<0.01$; (*) $p<0.001$; (****) $p<0.0001$; (ns) not significant.

Figure 14:
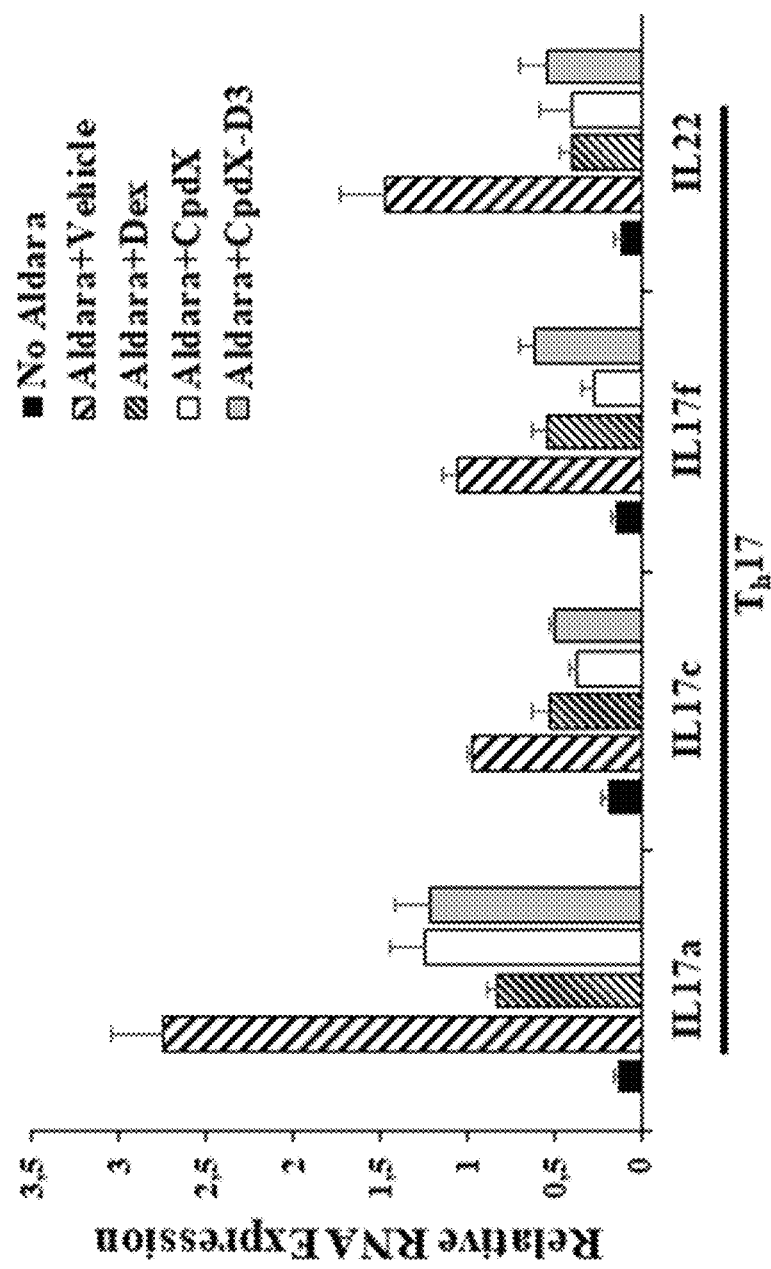

FIG. 14 is a histogram showing the relative RNA expression measured by q-RT-PCR analysis of RNA transcripts of the genes encoding interleukin-17a [IL17a], interleukin-17c [IL17c], interleukin-17 [IL17f] and interleukin-22 [IL22]. RNA transcripts were extracted from mouse ear skin samples after a 9 day induction of an Aldara®-induced psoriasis-like inflammation, including a topical treatment for the last 5 days with either ethanol [Aldara+Vehicle], 1 nmole/cm² dexamethasone [Aldara+Dex], (R/S)-5-[4-(5-fluoro-2-methoxyphenyl)-2-hydroxy-4-methyl-2-(trifluoromethyl)pentylamino]isoben-zofuran-1(3H)-one [Aldara+CpdX], (R/S)-5-{4-[2-(methoxy-D3)-5-fluorophenyl]-2-hydroxy-4-methyl-2-(trifluoromethyl) pentylamino}isobenzofuran-1(3H)-one [Aldara+CpdX-D3]. The $T_h17$-specific pro-inflammatory interleukins are highlighted. Data are represented as mean±SEM of at least three independent experiments with at least three mice per treatment.

Figure 15:
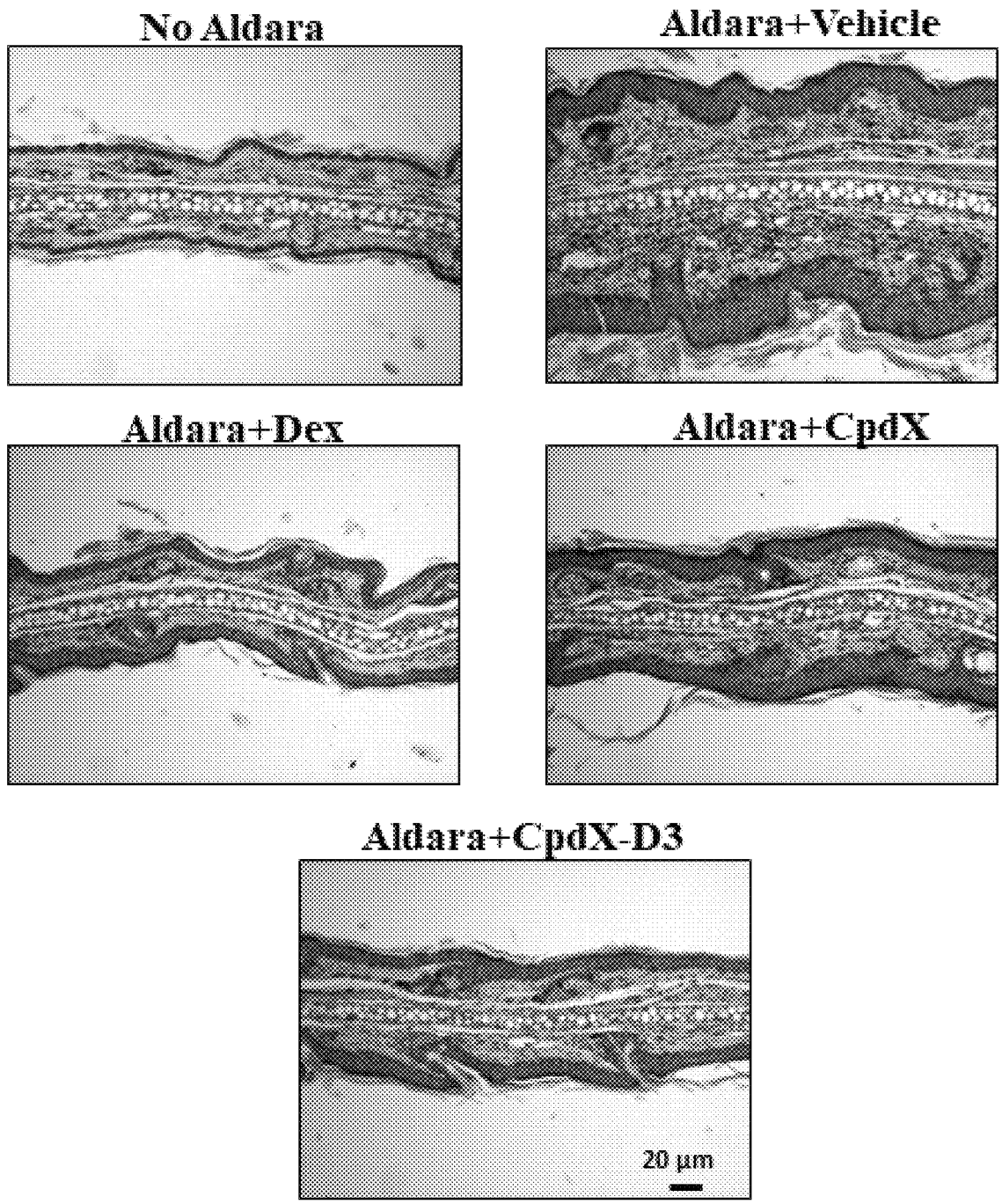

FIG. 15 is a set of five micrographs showing an Aldara®-generated psoriasis-like ear skin inflammation, followed by 5-day topical treatments as described in FIG. 14. The mouse ear skin samples were stained with hematoxylin and eosin. Scale bar represents 20 µm.

Figure 16:
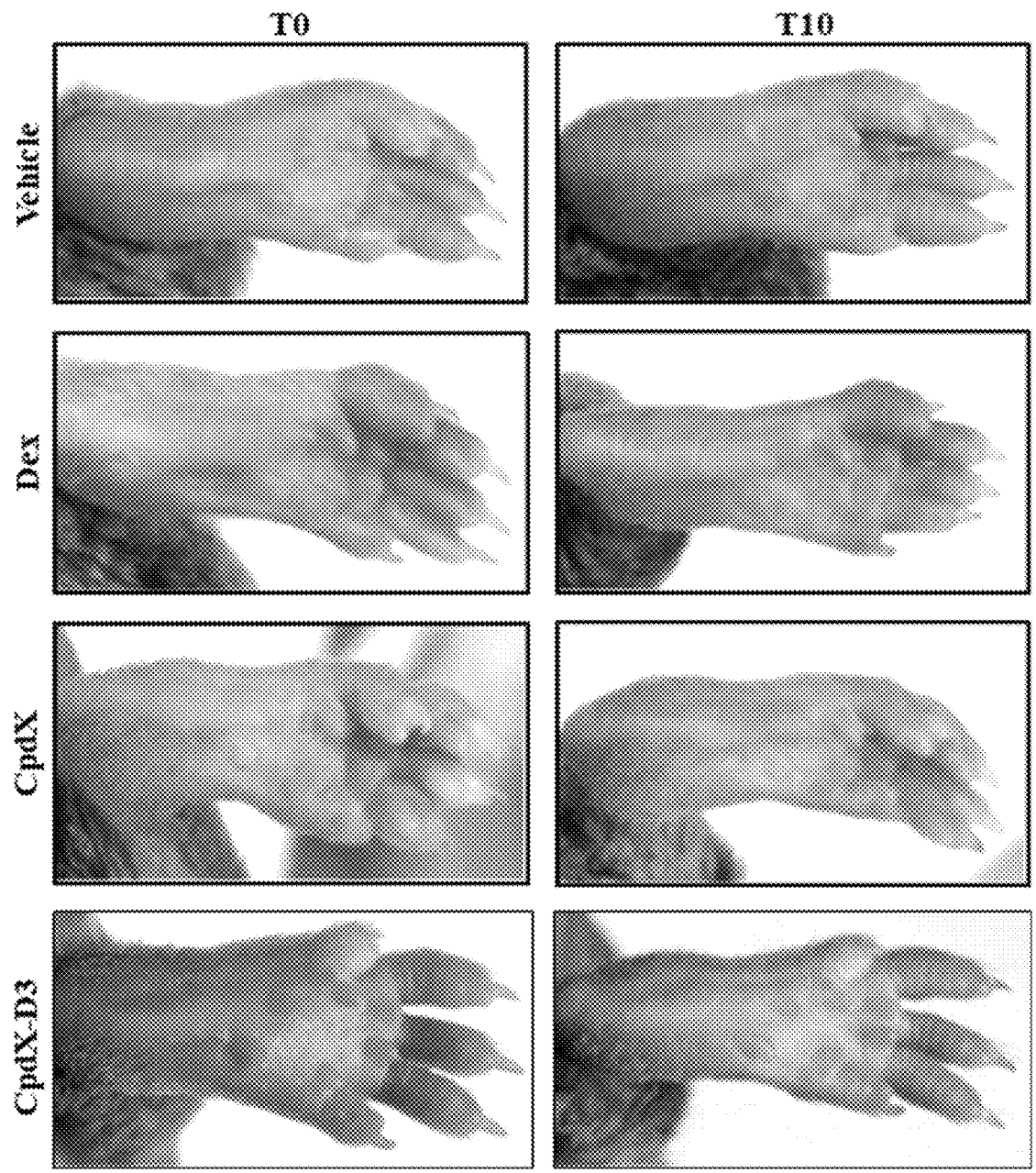

FIG. 16 is a set of eight micrographs showing the hind paws of mice in which a collagen-induced arthritis-like inflammation was induced (T0, left panels) and treated with a 10-day (T10) intraperitoneal administration (right panels), with NaCl 0.9% [Vehicle], 1 mg/kg body weight of either dexamethasone [Dex], (R/S)-5-[4-(5-fluoro-2-methoxyphenyl)-2-hydroxy-4-methyl-2-(trifluoromethyl)pentylamino]isoben-zofuran-1(3H)-one [CpdX], (R/S)-5-{4-[2-(methoxy-D3)-5-fluorophenyl]-2-hydroxy-4-methyl-2-(trifluoromethyl)-pentylamino}isobenzofuran-1(3H)-one [CpdX-D3].

Figure 17:
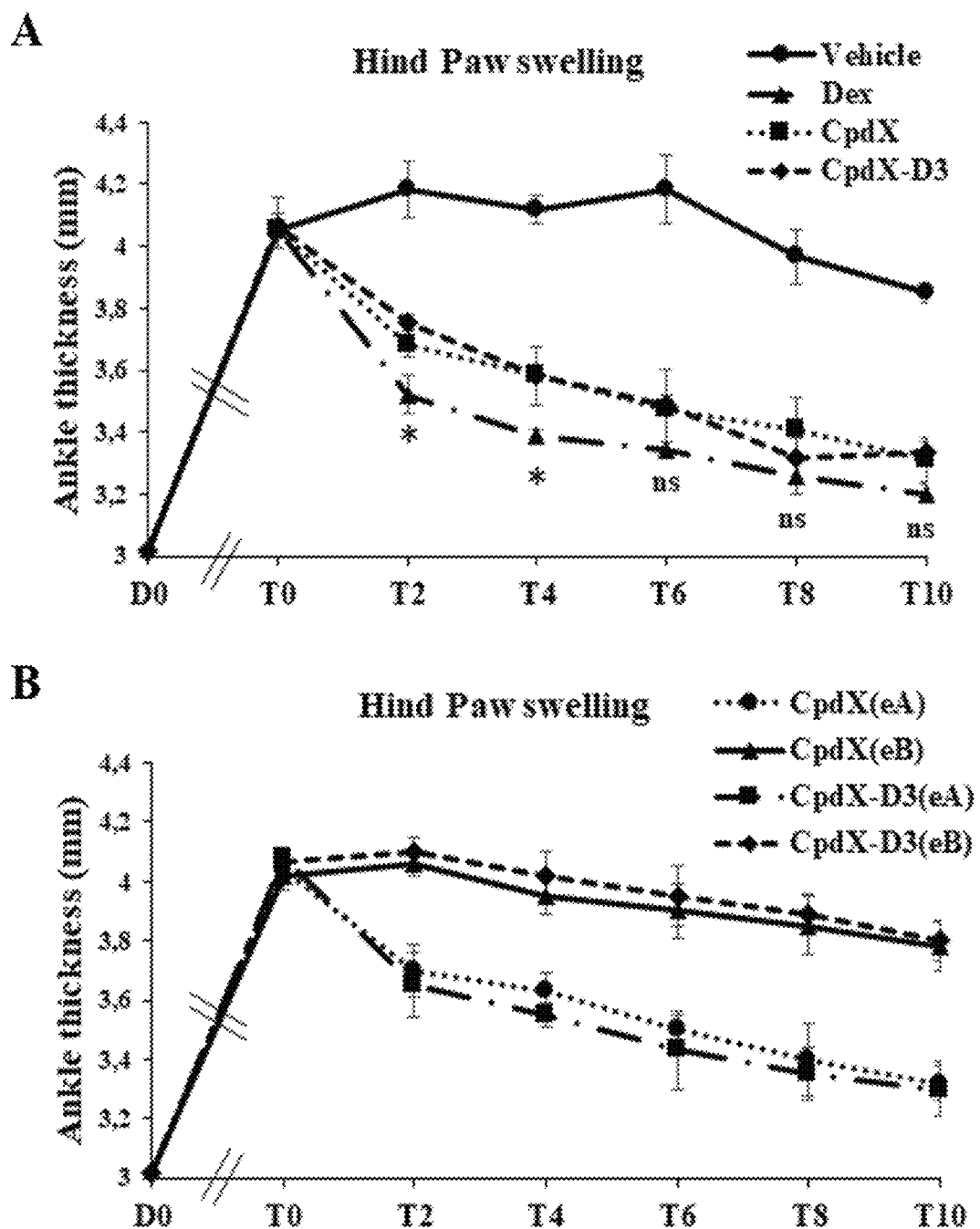

FIG. 17 is a set of two graphs showing the thickness (in mm) of the hind paws (at the ankle level) of mice after induction of an arthritis-like inflammation (at T0) and an intraperitoneal administration for 10 days (T10) (A) with NaCl 0.9% [Vehicle], 1 mg/kg body weight of either dexamethasone [Dex], (R/S)-5-[4-(5-fluoro-2-methoxyphenyl)-2-hydroxy-4-methyl-2-(trifluoromethyl)pentylamino] isobenzofuran-1(3H)-one [CpdX] or (R/S)-5-{4-[2-(methoxy-D3)-5-fluorophenyl]-2-hydroxy-4-methyl-2-(trifluoromethyl)-pentylamino}isobenzofuran-1(3H)-one [CpdX-D3]; and (B) with [CpdX-(eA)], [CpdX(eB)], [CpdX-D3(eA)] or [CpdX-D3(eB)]. Data are represented as mean±SEM with at least six mice per treatment. The statistical significance compared to the Dex treatment was calculated by student t test. (*) $p<0.05$; (ns) indicates that the difference observed between Dex-treated, CpdX-treated and CpdX-D3-treated mice are not significant.

Figure 18:
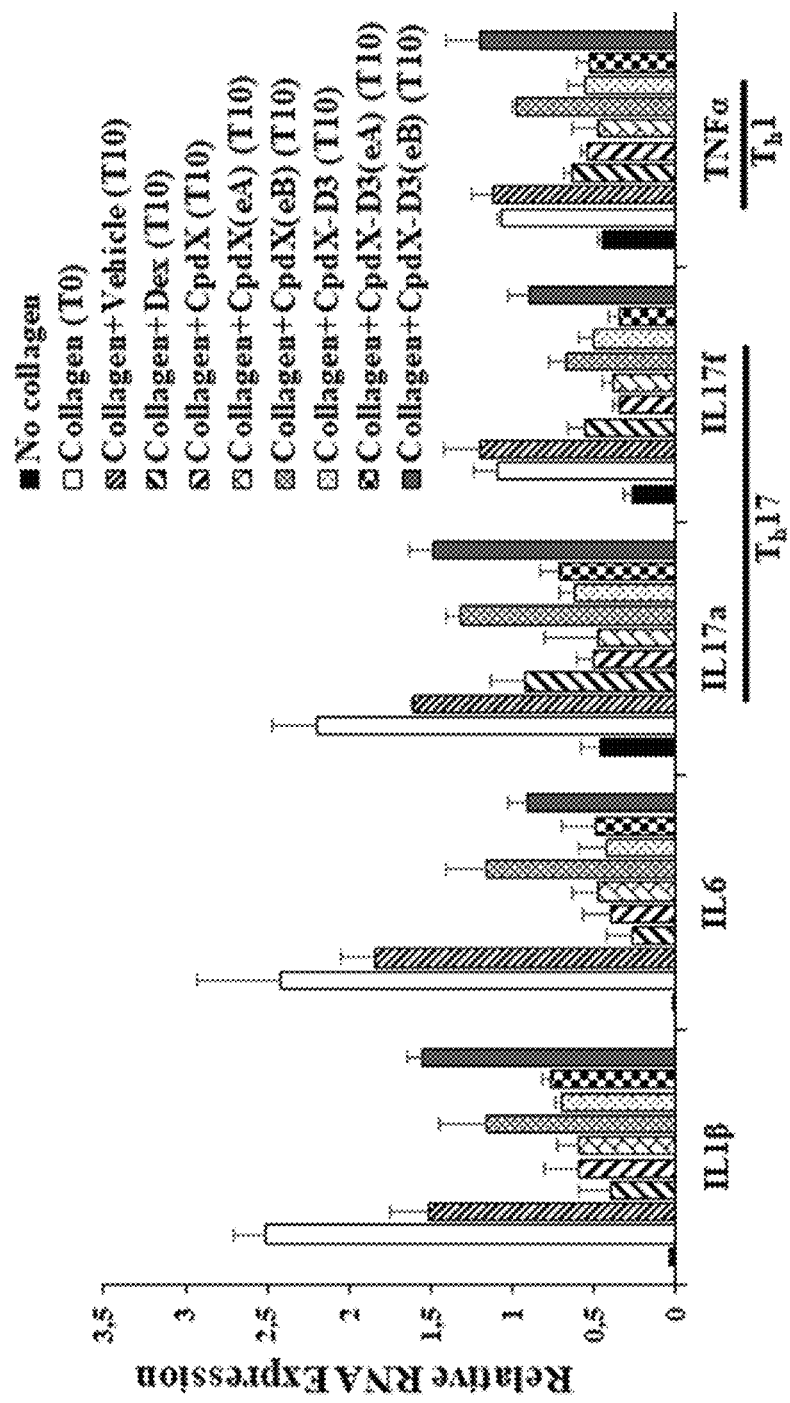

FIG. 18 is a histogram showing the relative RNA expression measured by q-RT-PCR analysis of RNA transcripts of interleukin-1β [IL1β], interleukin-6 [IL6], interleukin-17a [IL17a], interleukin-17f [IL17f] and tumor necrosis factor alpha [TNFα]. Total RNA transcripts were extracted from mouse whole hind paws either before (T0) or after a 10-day treatment (T10) as described in FIG. 17. $T_h17$- and $T_h1$-specific pro-inflammatory interleukins are highlighted. Data are represented as mean±SEM with at least six mice per treatment.

Figure 19:
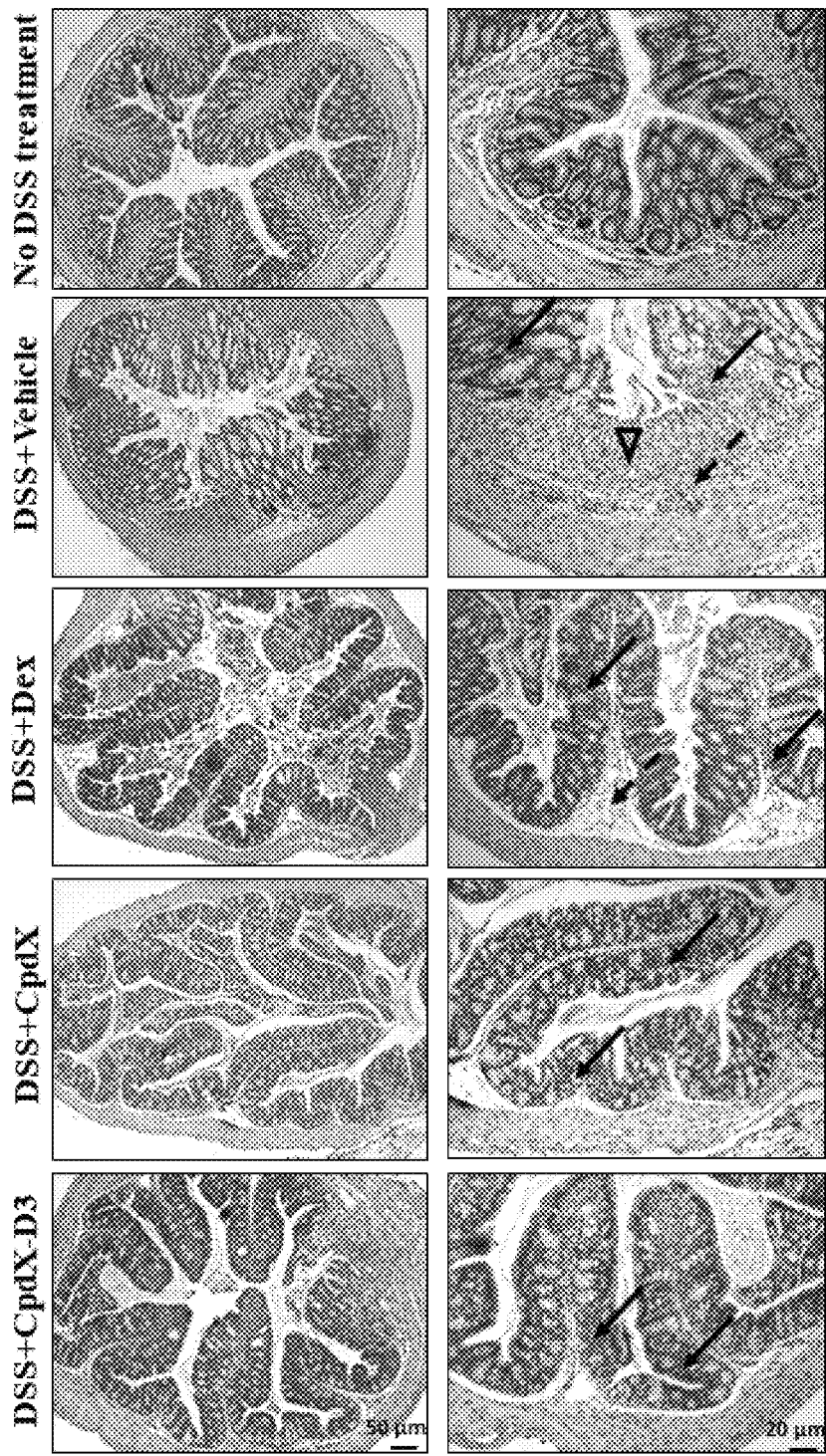

FIG. 19 is a set of ten micrographs of colon sections (at two magnifications with scale bar representing 50 µm or 20 µm respectively) showing an ulcerative colitis induced by a 13-day DSS (3% dextran sodium sulfate) treatment, as compared to a normal colon section [No DSS treatment], and to sections from mice treated on D11, D12 and D13 with either an intraperitoneal administration of NaCl 0.9% [DSS+Vehicle], 1 mg/kg body weight dexamethasone [DSS+Dex], (R/S)-5-[4-(5-fluoro-2-methoxy-phenyl)-2-hydroxy-4-methyl-2-(trifluoromethyl)pentylamino]isobenzofuran-1 (3H)-one [DSS+CpdX] or (R/S)-5-{4-[2-(methoxy-D3)-5-fluoro-phenyl]-2-hydroxy-4-methyl-2-(trifluoromethyl)-pentylamino}isobenzofuran-1(3H)-one [DSS+CpdX-D3]. Colon sections were initially stained with hematoxylin and eosin. Solid arrows: mucosal inflammatory cell infiltration; dotted arrows: submucosal inflammatory cell infiltration; arrow head: ulceration.

Figure 20:
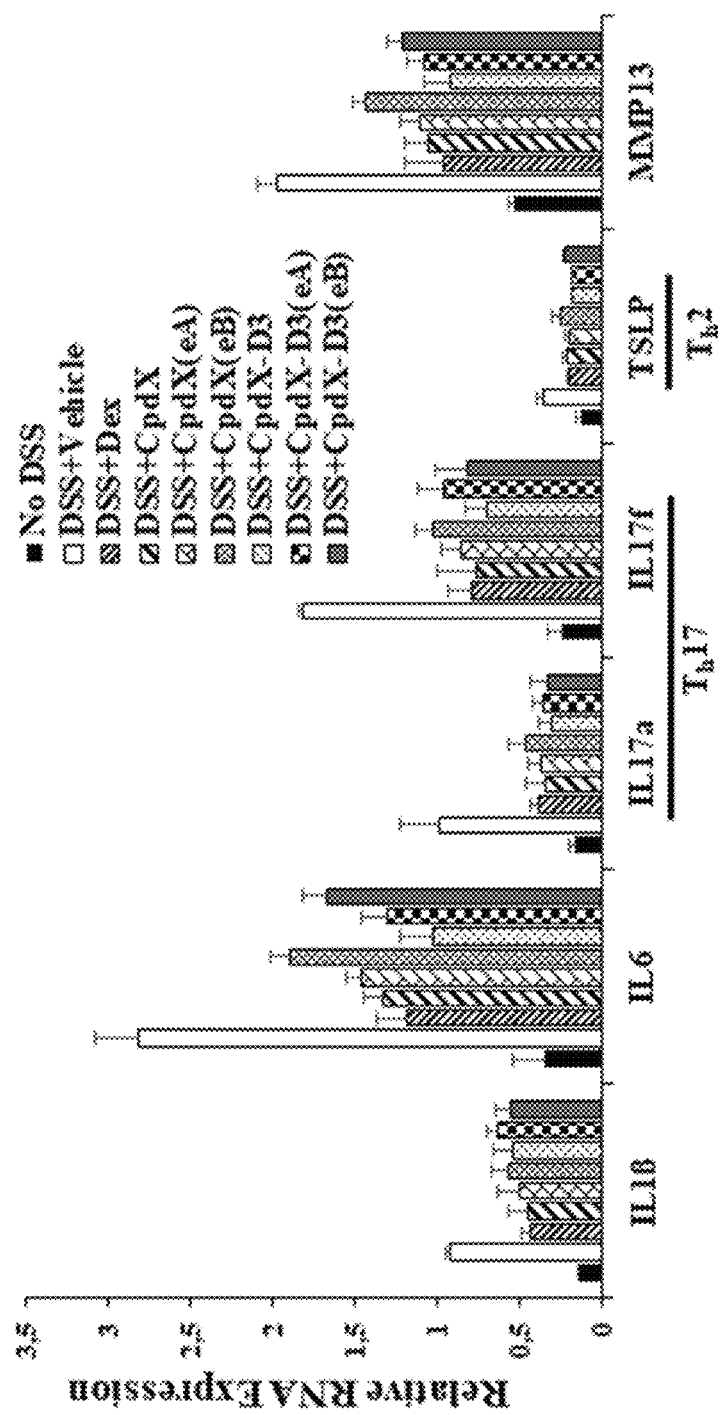

FIG. 20 is a histogram showing the comparative q-RT-PCR analyses of RNA transcripts of the genes encoding interleukin-1β [IL1β], interleukin-6[IL6], interleukin-17a [IL 17a], interleukin-17f [IL17f], thymic stromal lymphopoietin [TSLP] and collagenase 3 [MMP13]. $T_h17$- and $T_h2$-specific pro-inflammatory interleukins are highlighted. RNA transcripts were extracted from colon samples of mice orally-treated with 3% DSS (in drinking water) for 13 days, together with an intraperitoneal administration on D11, D12 and D13, of either NaCl 0.9% [DSS+Vehicle], 1 mg/kg body weight of either dexamethasone [DSS+Dex], (R/S)-5-[4-(5-fluoro-2-methoxyphenyl)-2-hydroxy-4-methyl-2-(trifluoromethyl)pentylamino]-isobenzofuran-1(3H)-one [DSS+CpdX], CpdX(eA) [DSS+CpdX(eA)], CpdX(eB) [DSS+CpdX(eB)], (R/S)-5-{4-[2-(methoxy-D3)-5-fluorophenyl]-2-hydroxy-4-methyl-2-(trifluoromethyl) pentylamino}isobenzo-furan-1(3H)-one [DSS+CpdX-D3], CpdX-D3(eA) [DSS+CpdX-D3(eA)] or CpdX-D3(eB) [DSS+CpdX-D3(eB)]. Data are represented as mean±SEM of at least three independent experiments with at least four mice per treatment.

FIG. 21 is (A) a set of nine micrographs showing, 20 minutes after the last treatment on day 24, the clinical appearance of mouse eyes upon induction of an ovalbumin (OVA)-induced allergic conjunctivitis that includes 14 days of OVA sensitization, followed by a 10-day challenge with either NaCl 0.9% (Vehicle) or OVA. On day 22, 23 and 24, the OVA-challenged mouse eyes were co-treated with NaCl 0.9% [OVA], 0.1% of either dexamethasone [OVA+Dex], (R/S)-5-[4-(5-fluoro-2-methoxyphenyl)-2-hydroxy-4-methyl-2-(trifluoromethyl)pentylamino]isobenzofuran-1 (3H)-one [OVA+CpdX], CpdX-(eA) [OVA+CpdX(eA)], CpdX(eB) [OVA+CpdX(eB)], (R/S)-5-{4-[2-(methoxy-D3)-5-fluorophenyl]-2-hydroxy-4-methyl-2-(trifluoromethyl)pentylamino}isobenzofuran-1(3H)-one [OVA+CpdX-D3], CpdX-D3(eA) [OVA+CpdX-D3(eA)] or CpdX-D3(eB) [OVA+CpdX-D3(eB)]; and (B) a graph showing the clinical score (conjunctival hyperemia, lid edema and tearing) of mouse eyes treated as described under (A). Scoring was performed, and each parameter was graded on a scale ranging from 0 to 3, (0=absence, 1=mild, 2=moderate, and 3=severe symptoms). Thus, each animal received a total clinical score of ranging from 0 to 9, and the data were expressed as mean±SEM with at least four mice per treatment.

Figure 22:
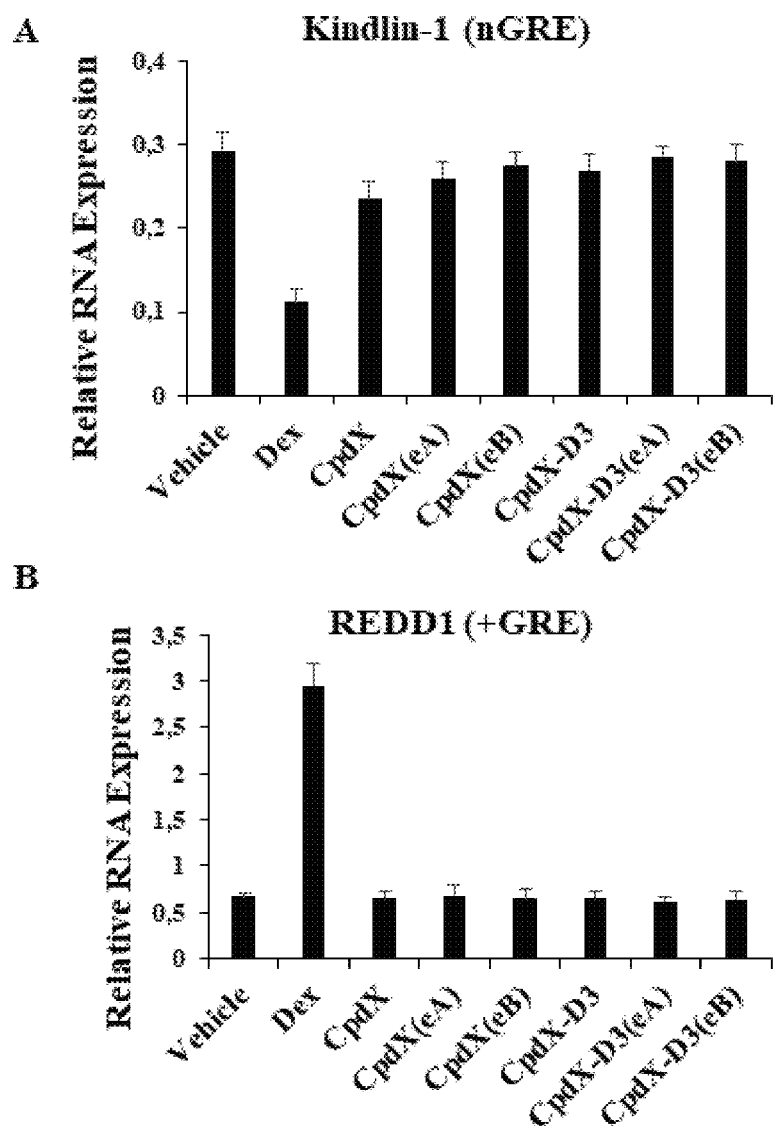

FIG. 22 is a set of two histograms showing the relative expression (measured by q-RT-PCR analyses) of RNA transcripts of (A) Kindlin-1 (a nGRE-containing gene) and (B) REDD1 (a +GRE-containing gene) genes. Mice were shaved on the dorsal skin and then topically treated with ethanol [Vehicle], 1 nmole/cm$^2$ of either dexamethasone [Dex], (R/S)-5-[4-(5-fluoro-2-methoxyphenyl)-2-hydroxy-4-methyl-2-(trifluoromethyl)penty-lamino]-isobenzofuran-1(3H)-one [CpdX], [CpdX(eA)], [CpdX(eB)], (R/S)-5-{4[2-(methoxy-D3)-5-fluorophenyl]-2-hydroxy-4-methyl-2-(trifluoromethyl)pentylamino}-isobenzofuran-1-(3H)-one [CpdX-D3], [CpdX-D3(eA)] or [CpdX-D3(eB)] for 8 days. Data are represented as mean±SEM of at least three independent experiments with at least three mice per treatment.

Figure 23:
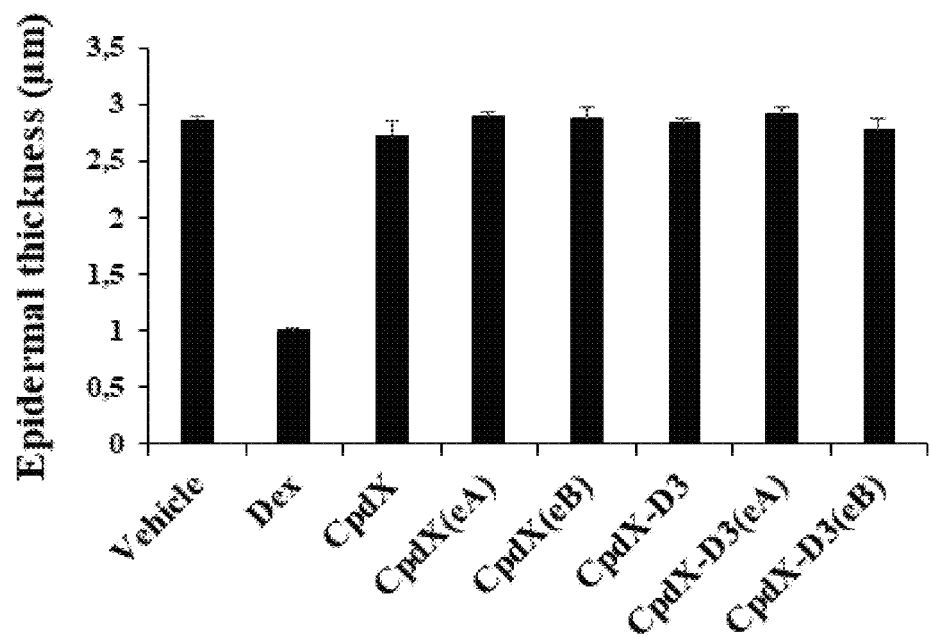

FIG. 23 is a histogram showing a morphometric analysis of the epidermal thickness (in μm) in mice shaved on the dorsal skin and then topically treated for 8 days as described in FIG. 22. Data are represented as mean±SEM of at least three independent experiments with at least three mice per treatment.

Figure 24:
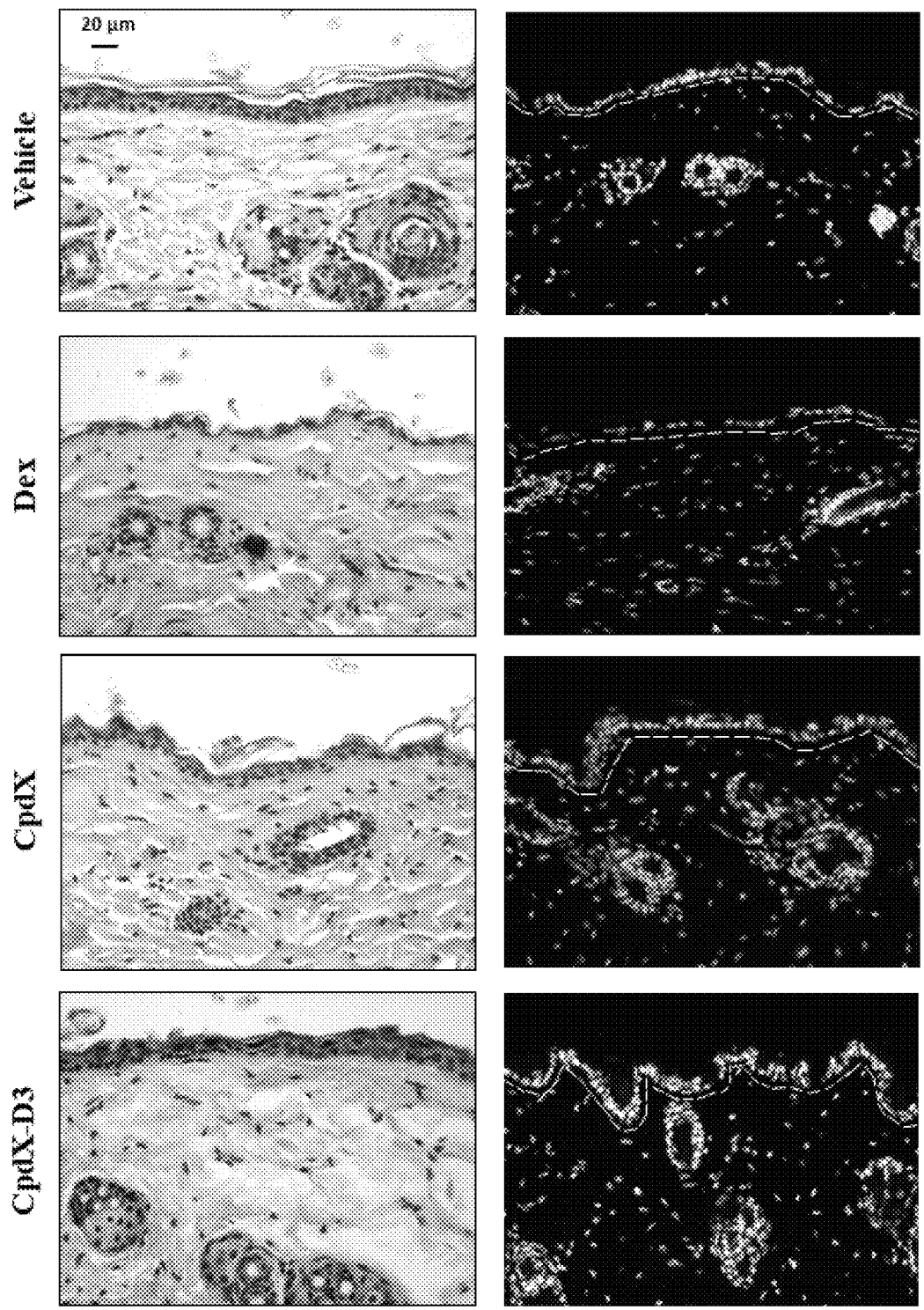
Figure 24:
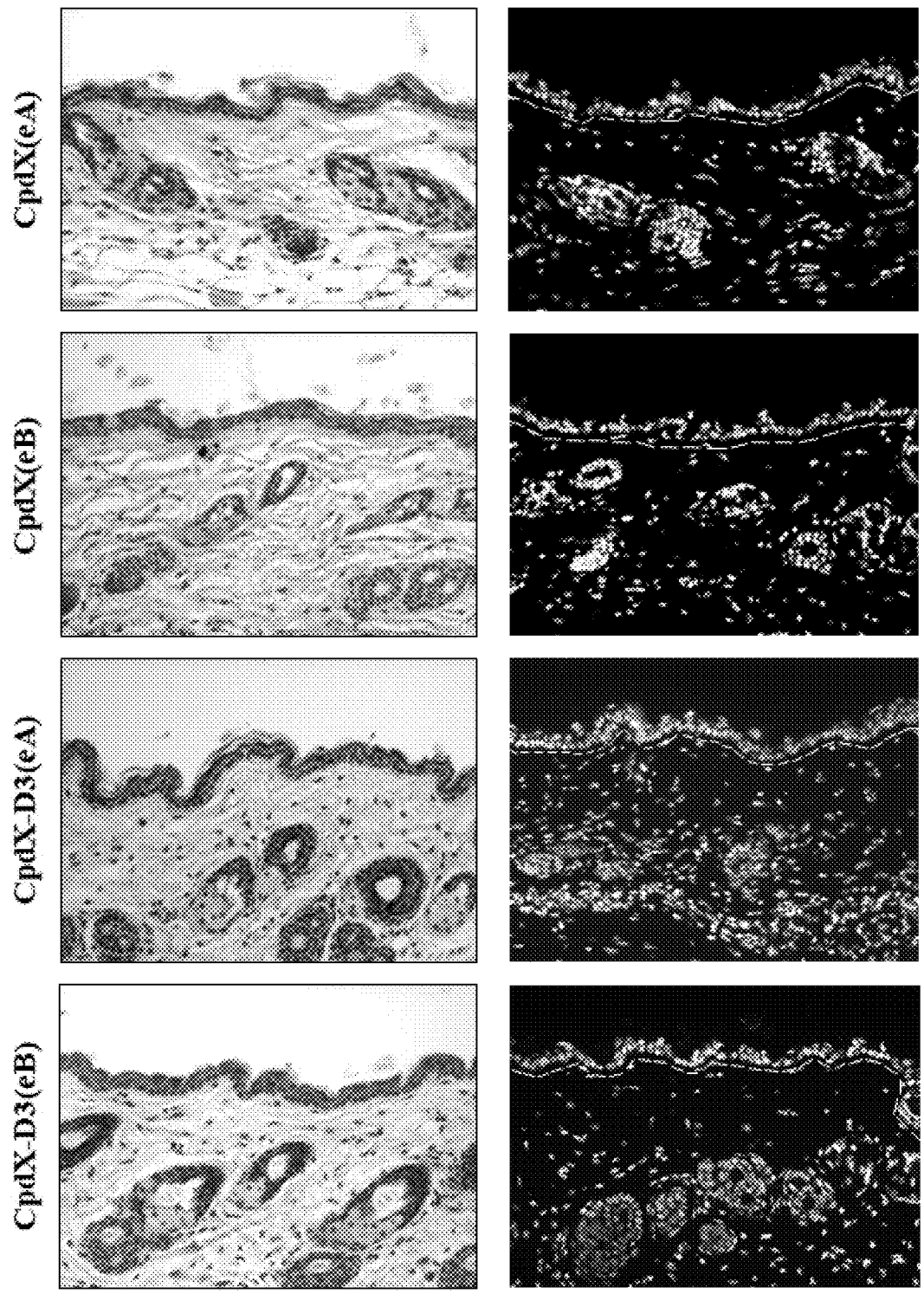

FIG. 24 is a set of sixteen micrographs showing the skin atrophy in mice shaved on the dorsal skin and then topically treated as described in FIG. 22. Left panels: the skin samples were stained with hematoxylin and eosin. Right panels: nucleus was stained by DAPI. The scale bar represents 20 μm.

FIG. 25 is a set of ten graphs for five cortical bone parameters measured by microCT: (A) bone volume/total volume (%); (B) cortical thickness (mm); (C) total area (mm$^2$); (D) bone area (mm$^2$) and (E) marrow area (mm$^2$). 8 week-old mice were treated for three months with a daily subcutaneous injection of either NaCl 0.9% [Vehicle], 1 mg/kg body weight dexamethasone [Dex], (R/S)-5-[4-(5-fluoro-2-methoxyphenyl)-2-hydroxy-4-methyl-2-(trifluoromethyl)pentylamino]isobenzofuran-1(3H)-one [CpdX], [CpdX(eA)], [CpdX(eB)], (R/S)-5-{4-[2-(methoxy-D3)-5-fluorophenyl]-2-hydroxy-4-methyl-2-(trifluoromethyl)pentylamino}isobenzofuran-1(3H)-one [CpdX-D3], [CpdX-D3(eA)] or [CpdX-D3(eB)]. The FX Quantum micro-CT scanner (Perkin Elmer) was used to perform measurements at the midshaft tibia. The data correspond to the mean (as pointed by arrow heads) ±SEM for at least six mice per treatment. The statistical significance compared to the vehicle treatment was calculated through One-way ANOVA test followed by Dunnett's multiple comparison test (*) p<0.05; () p<0.01 (*) p<0.001; (****) p<0,0001; (ns): not significant.

Figure 26:
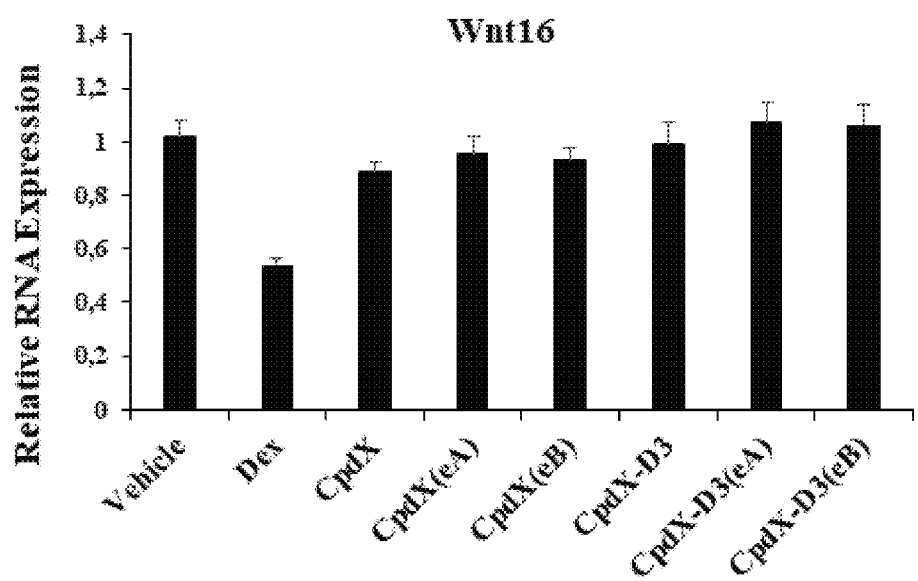

FIG. 26 is a histogram showing the relative expression (measured by q-RT-PCR analyses) of RNA transcripts of the Wnt16 gene in mouse tibia. 8-week-old mice were treated as indicated in FIG. 25. Data are represented as mean±SEM with at least six mice per treatment.

Figure 27:
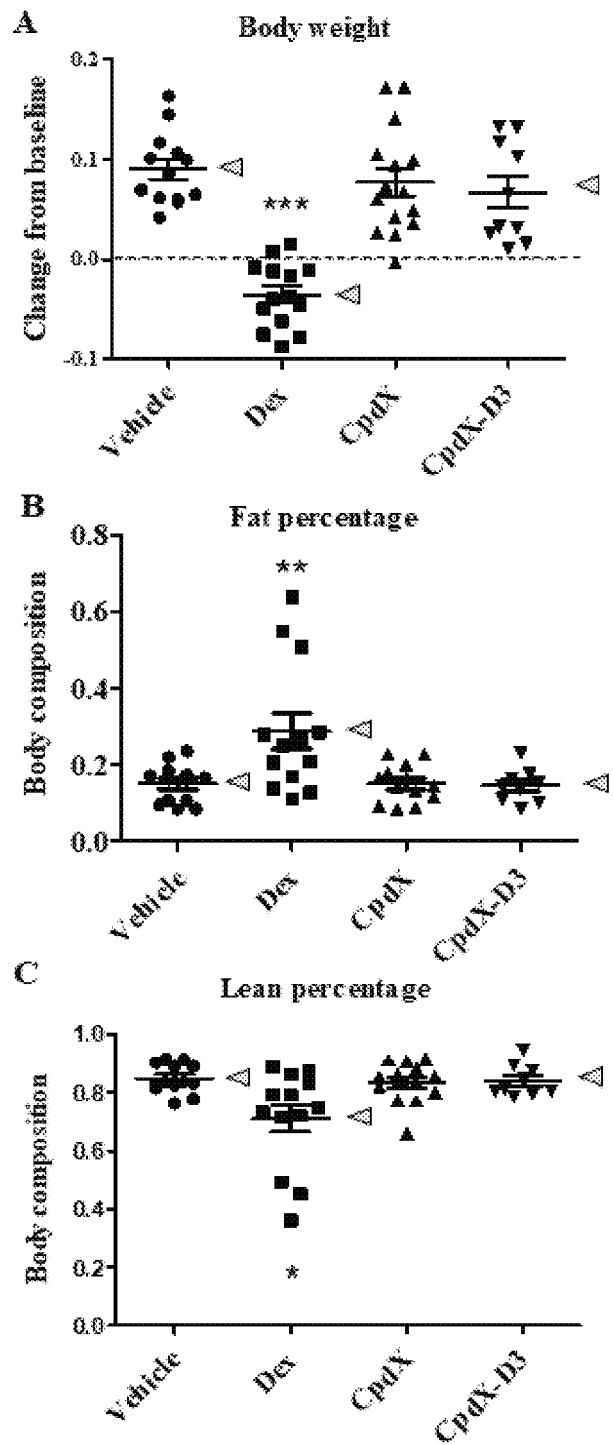

FIG. 27 is a set of three graphs showing the change from baseline (before treatment) of (A) the body weight, (B) the fat percentage and (C) the lean percentage of 8-week-old mice treated as indicated for three additional months with a daily subcutaneous injection of either NaCl 0.9% [Vehicle], 1 mg/kg body weight dexamethasone [Dex], (R/S)-5[4-(5-fluoro-2-methoxyphenyl)-2-hydroxy-4-methyl-2-(trifluoromethyl)pentylamino]iso-benzofuran-1(3H)-one [CpdX] or (R/S)-5-{4-[2-(methoxy-D3)-5-fluorophenyl]-2-hydroxy-4-methyl-2-(trifluoromethyl)pentylamino}isobenzofuran-1(3H)-one [CpdX-D3]. The data correspond to the mean (as pointed by arrow heads) ±SEM for at least nine mice per treatment. The statistical significance was calculated through Krustal-Walis test followed by Dunn's multiple comparison test; (*) p<0.05; () p<0.01 (*) p<0.001.

Figure 28:
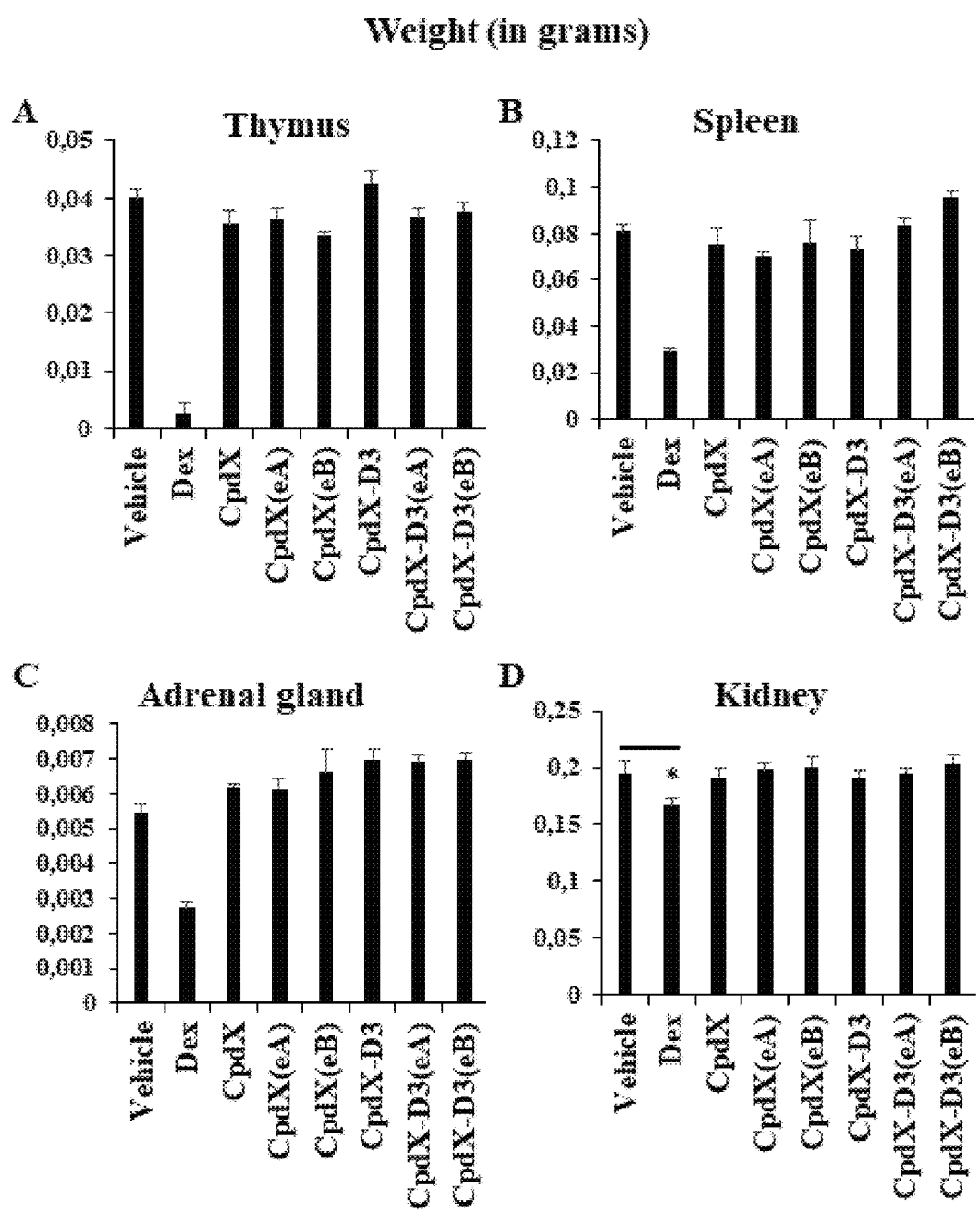

FIG. 28 is a set of four histograms showing the weight (in grams) of (A) thymus, (B) spleen, (C) adrenal gland and (D) kidney of 8-week-old mice treated for three additional months with a daily subcutaneous injection of NaCl 0.9% [Vehicle], 1 mg/kg body weight dexamethasone [Dex] or (R/S)-5-[4-(5-fluoro-2-methoxyphenyl)-2-hydroxy-4-methyl-2-(trifluoromethyl)pentylamino]isobenzofuran-1(3H)-one [CpdX], [CpdX(eA)], [CpdX-(eB)], (R/S)-5-{4-[2-(methoxy-D3)-5-fluorophenyl]-2-hydroxy-4-methyl-2-(trifluoro-methyl)pentylamino}isobenzofuran-1(3H)-one [CpdX-D3], [CpdX-D3(eA)] or [CpdX-D3(eB)]. Data are represented as mean±SEM for at least nine mice per treatment. The statistical significance was calculated by student t test; (*) p<0.05.

Figure 29:
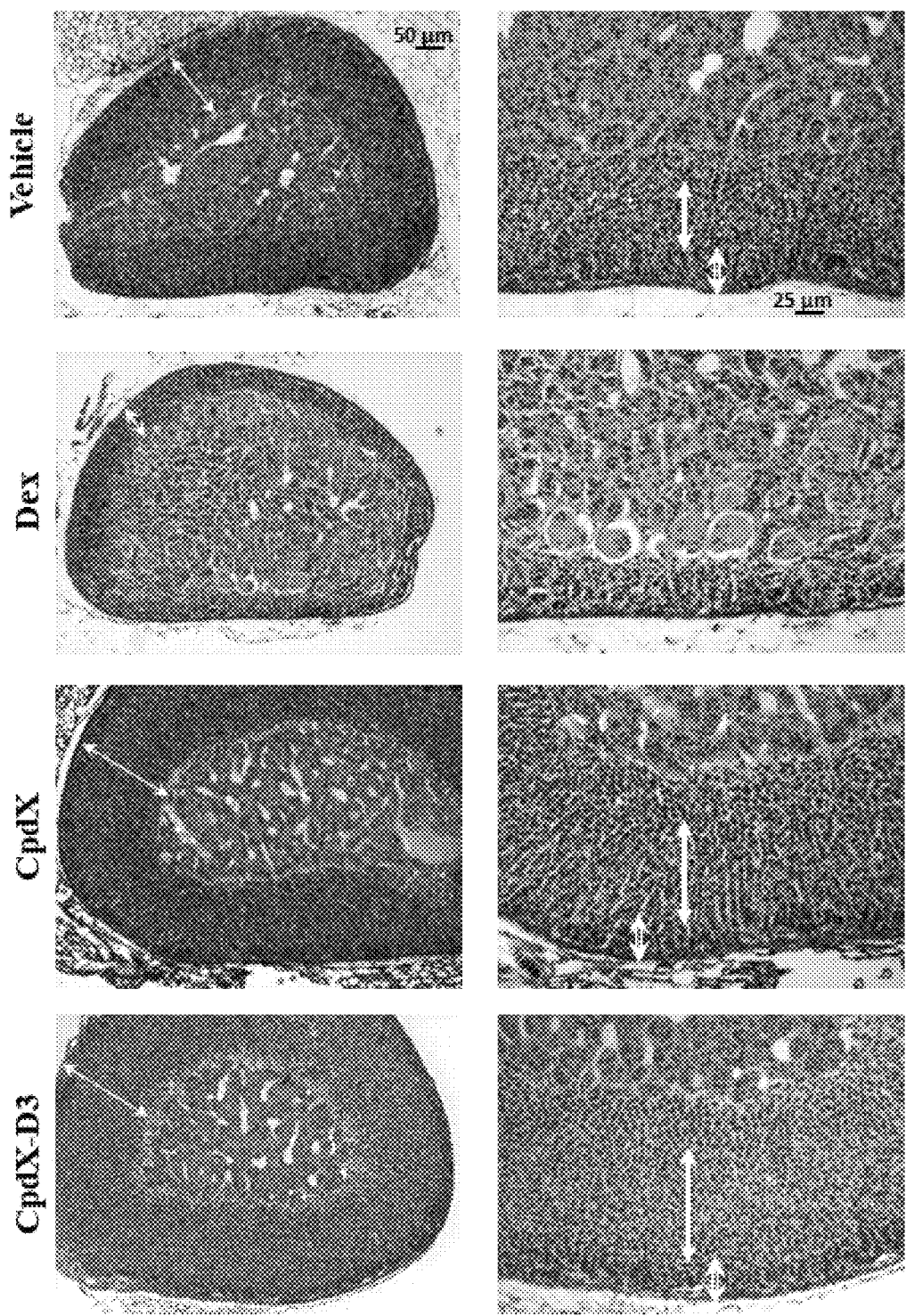

FIG. 29 is a set of eight micrographs (at two different magnifications with scale bar representing 50 μm or 25 μm respectively) showing sections of adrenal glands of 8-week-old mice treated as indicated in FIG. 27. The cortex layer of the adrenal gland is indicated in left panels by double-headed arrows, while the fasciculata and the glomerulosa zones of the cortex are indicated by long bold double-headed arrows and small empty double-headed arrows in right panels, respectively.

Figure 30:
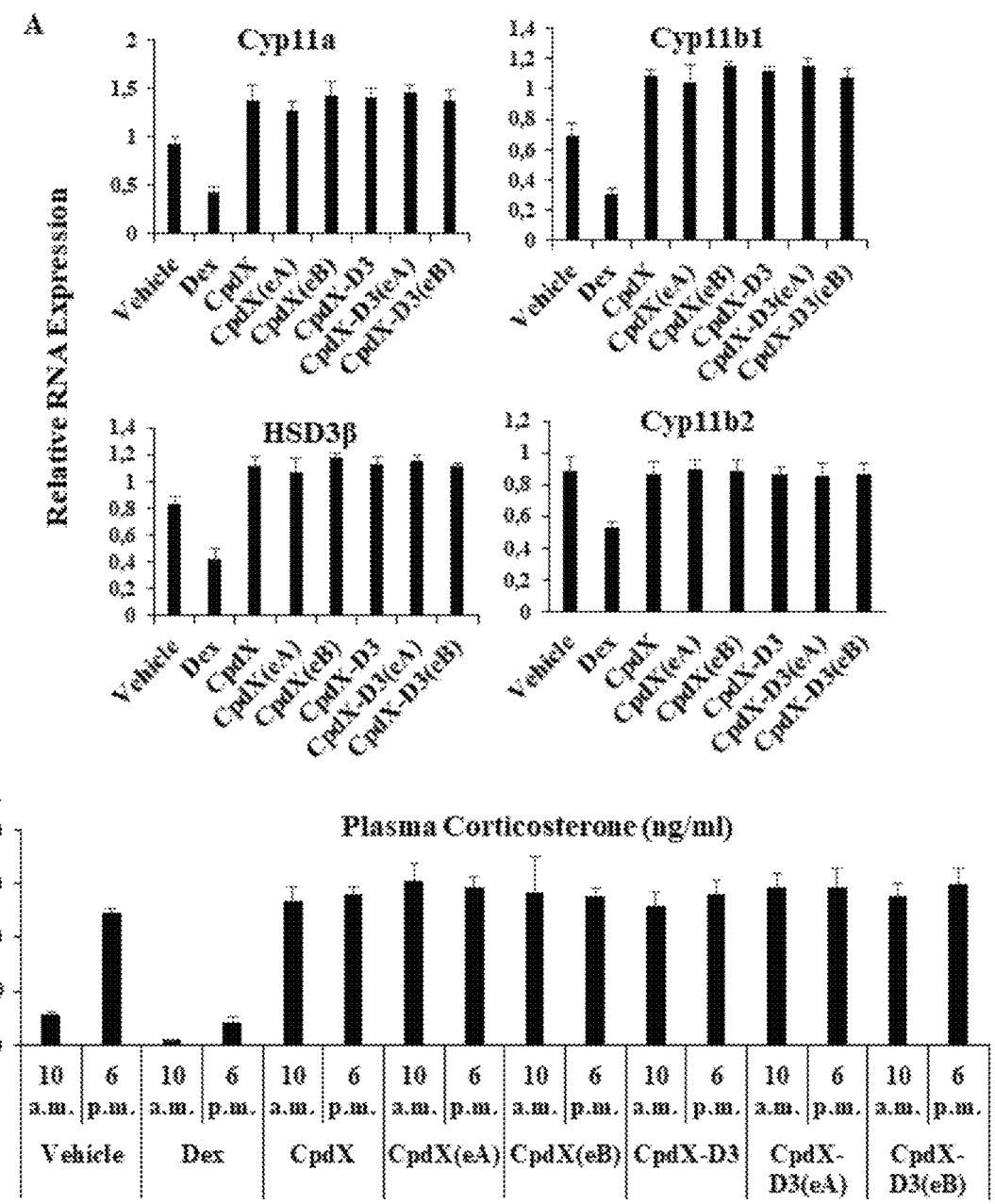

FIG. 30 shows the corticosterone synthesis in 8-week-old mice treated as indicated in FIG. 28. (A): relative expression in mouse adrenal glands of RNA transcripts (as determined by q-RT-PCR analyses) of steroid 11α-hydroxylase (Cyp11a), steroid 11β-hydroxylase (Cyp11b1), 3β-hydroxysteroid dehydrogenase (HSD3β) and aldosterone synthase (Cyp11b2) genes; (B): plasmatic corticosterone levels at 10 a.m. and 6 p.m. in mice treated as indicated. Data are represented as mean±SEM for at least nine mice per treatment.

Figure 31:
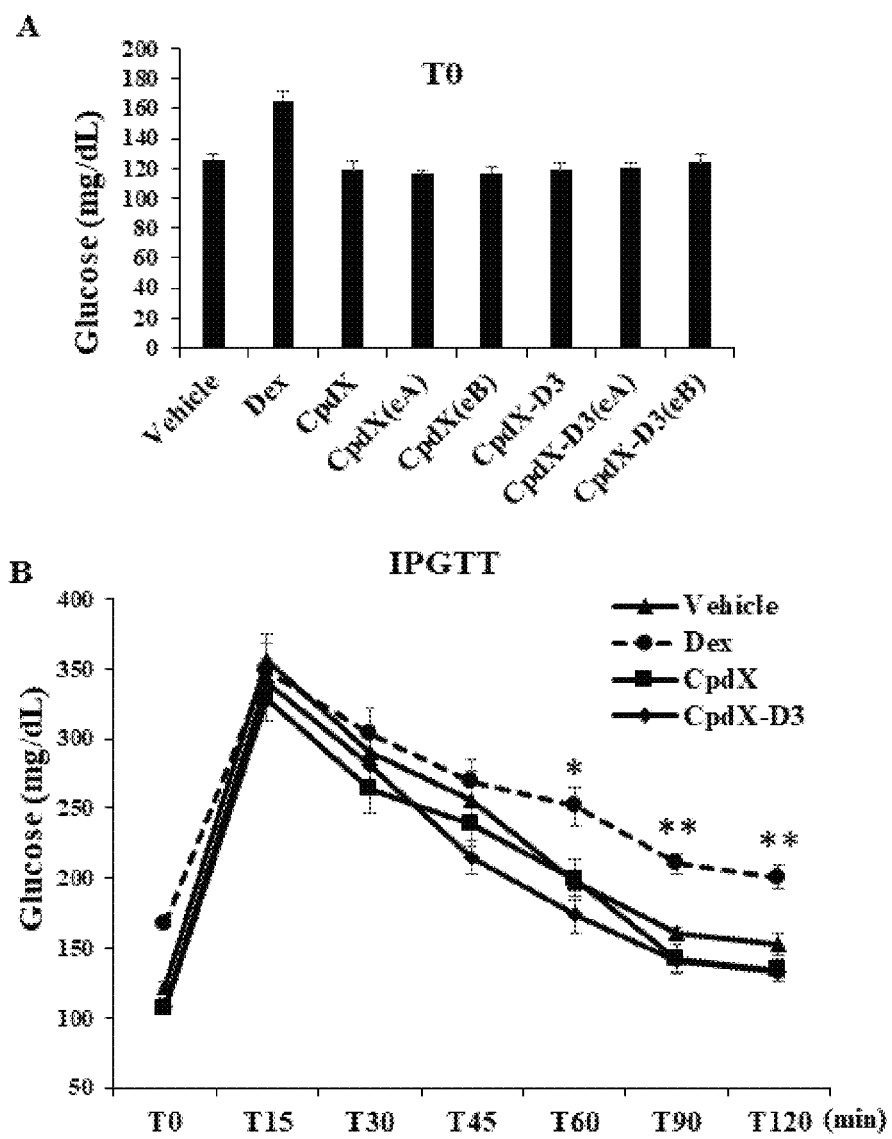

FIG. 31 is a set of two histograms showing the blood glucose levels (mg/dL) in 8-week-old mice treated as indicated in FIG. 28. (A): plasmatic glucose levels after an over-night 14-hour fasting; (B): 2-hour intraperitoneal glucose tolerance test (IPGTT) after a glucose i.p. injection (2 mg/kg body weight). Data are represented as mean±SEM for at least six mice per treatment. The statistical significance compared to the vehicle treatment was calculated by student t test; (*) p<0.05; (**) p<0.01.

Figure 32:
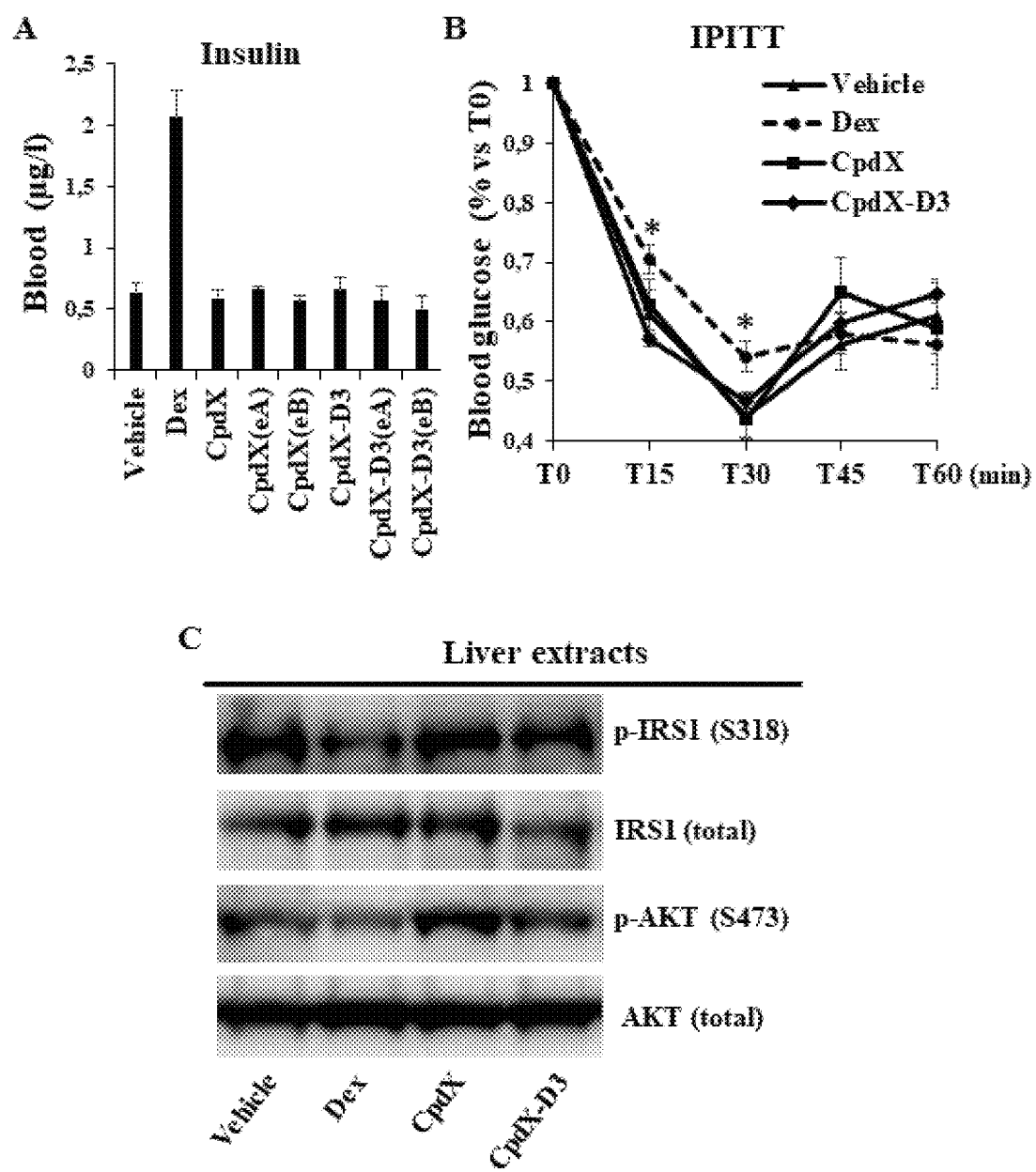

FIG. 32(A) is a histogram showing the blood insulin levels (μg/L) in 8-week-old mice treated as indicated in FIG. 28. Data are represented as mean±SEM for at least nine mice per treatment. (B): 1-hour intraperitoneal insulin tolerance test (IPITT) after an intraperitoneal injection of 0.75 U Insulin/kg body weight. Data are represented as mean±SEM with at least six mice per treatment. The statistical significance compared to the vehicle treatment was calculated by student t test, * p<0.01. (C): western blot analyses of mouse liver samples for phospho-insulin receptor substrate-1 phosphorylated at serine 318 (p-IRS1 S318), pan-insulin receptor substrate-1 (IRS total), phospho-protein kinase B phosphorylated at serine 473 (p-AKT S473) and pan-protein kinase B (AKT total) proteins.

Figure 33:
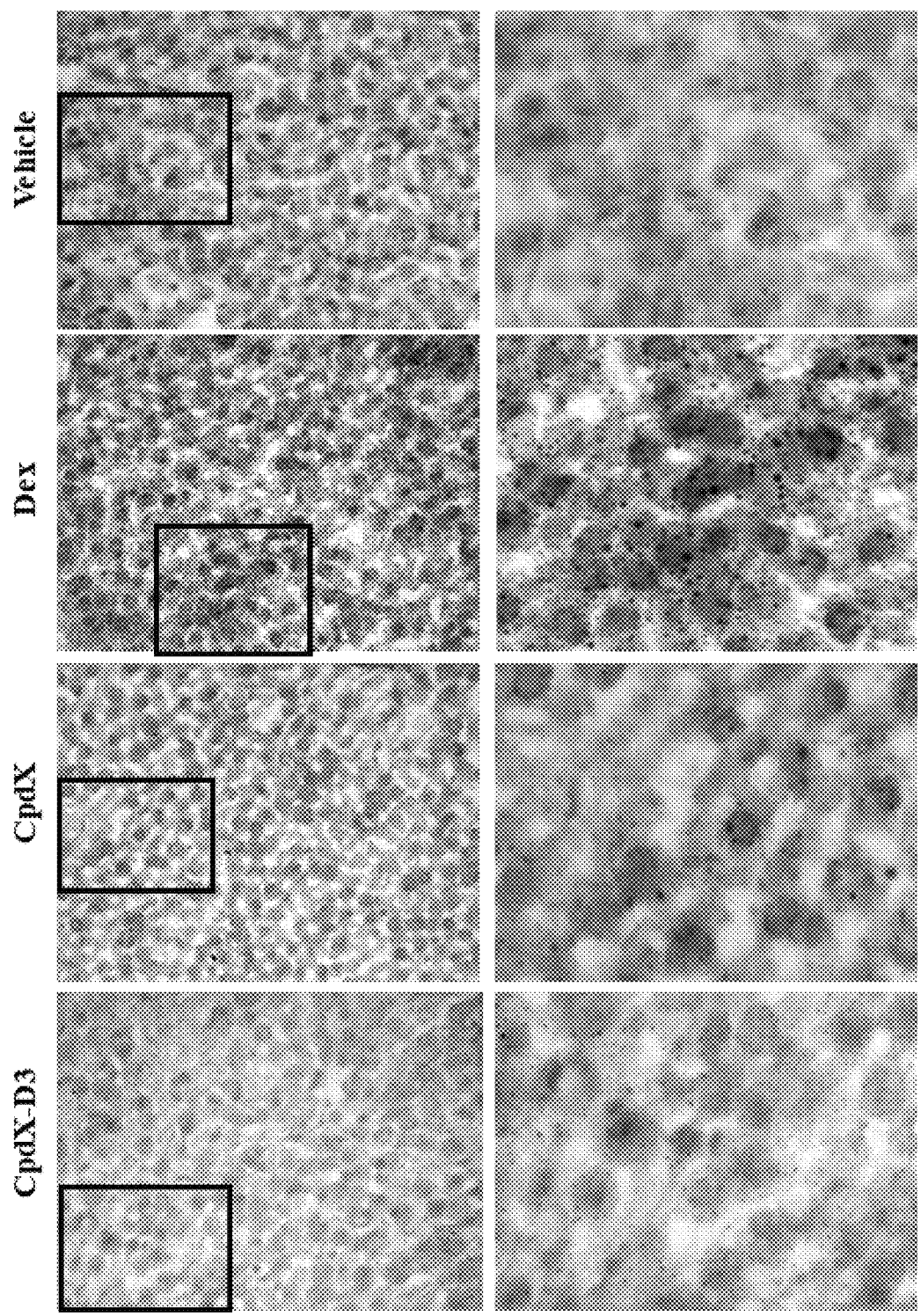
Figure 33:
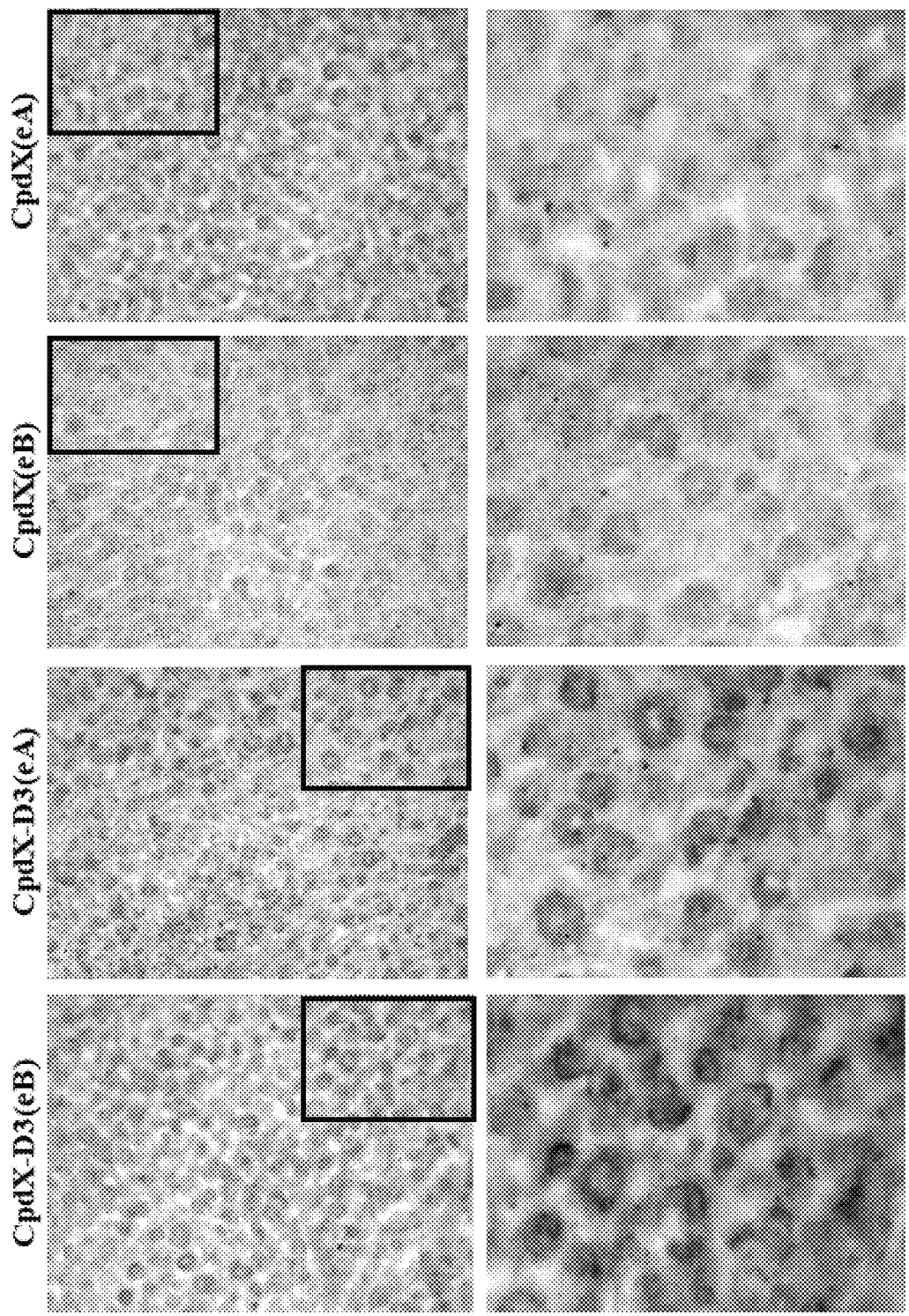

FIG. 33 is a set of sixteen micrographs (at two magnifications) showing a selective lipid deposition (revealed by 5% red oil staining of frozen liver sections) in the liver of 8-week-old mice treated as indicated in FIG. 28.

Figure 34:
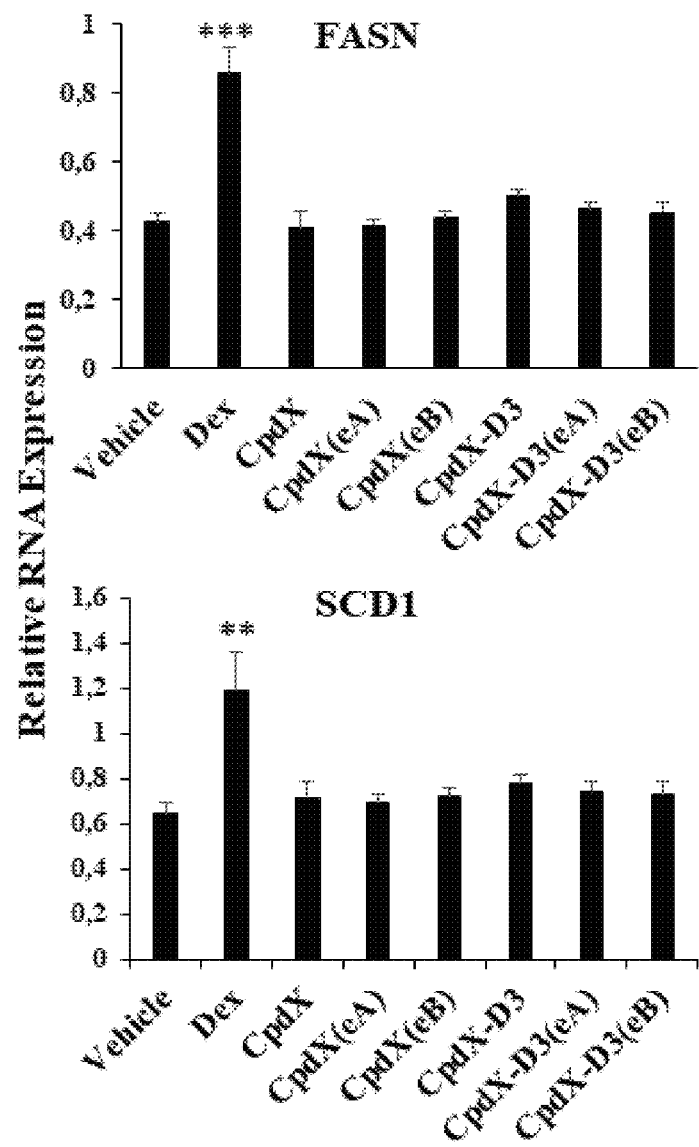

FIG. 34 is a set of two histograms showing the relative RNA expression (q-RT-PCR analysis) of transcripts of fatty acid synthase (FASN) and stearoyl-CoA desaturase-1 (SCD1) in mouse livers. 8-week-old mice were treated as indicated in FIG. 28. The data correspond to the mean±SEM for at least nine mice per treatment. The statistical significance was calculated by student t test; () p<0.01; (*) p<0.001.

Figure 35:
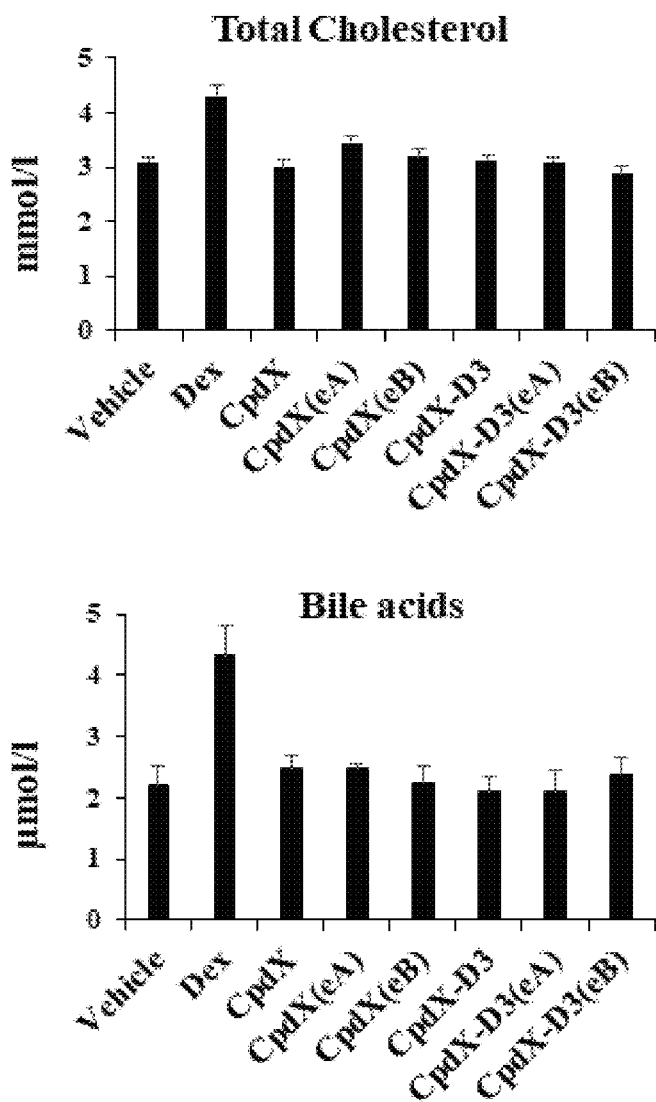

FIG. 35 is a set of two histograms showing the total cholesterol level (mmol/L) and bile acids levels (μmol/L) in blood from 8-week-old mice treated as indicated in FIG. 28. Data are represented as mean±SEM for at least nine mice per treatment.

DETAILED DESCRIPTION

"Adrenal suppression", or "adrenal insufficiency" as used herein, refers to a condition in which the adrenal glands do not produce adequate amounts of cortisol. Use of high-dose steroids for more than a week begins to produce suppression of the subject's adrenal glands because the exogenous glucocorticoids suppress hypothalamic corticotropin-releasing hormone (CRH) and pituitary adrenocorticotropic hormone (ACTH), as well as inhibit the syntheses of adrenal corticosterone synthesizing enzymes. With prolonged suppression, the adrenal glands atrophy and may take up to 9 months to recover full function after discontinuation of the exogenous glucocorticoid. During this recovery time, the subject is vulnerable to adrenal insufficiency during times of stress, such as illness, due to both adrenal atrophy and suppression of CRH and ACTH release.

"CpdX", as used herein, refers to the SElective Glucocorticoid Receptor Agonistic Modulator (SEGRAM) of Formula 1:

(Formula 1)

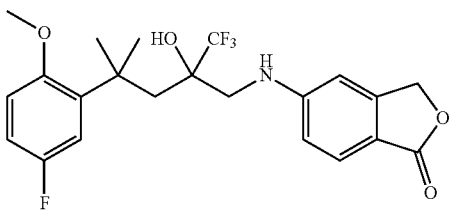

or a pharmaceutically acceptable enantiomer, deuterated form, salt, solvate and/or prodrug thereof. "CpdX" corresponds to 5-[4-(5-fluoro-2-methoxyphenyl)-2-hydroxy-4-methyl-2-(trifluoromethyl)pentylamino]-isobenzofuran-1 (3H)-one (see Example 1, FIG. 2A).

"CpdX(eA)", as used herein, refers to one of the two enantiomers of the SEGRAM of Formula 1 or a pharmaceutically acceptable salt, solvate or prodrug thereof. "CpdX (eA)" corresponds to the first elution peak of 5-[4-(5-fluoro-2-methoxyphenyl)-2-hydroxy-4-methyl-2-(trifluoromethyl) pentylamino]-isobenzofuran-1(3H)-one separated by preparative supercritical fluid chromatography (see Example 1, FIG. 2B).

"CpdX(eB)", as used herein, refers to one of the two enantiomers of the SEGRAM of Formula 1 or a pharmaceutically acceptable salt, solvate or prodrug thereof. "CpdX (eB)" corresponds to the second elution peak of 5-[4-(5-fluoro-2-methoxyphenyl)-2-hydroxy-4-methyl-2-(trifluoromethyl)pentylamino]-isobenzofuran-1(3H)-one separated by preparative supercritical fluid chromatography (see Example 1, FIG. 2B).

"CpdX-D3", as used herein, refers to a deuterated racemic form of the SEGRAM of Formula 1 or a pharmaceutically acceptable salt, solvate or prodrug thereof. "CpdX-D3" corresponds to 5-{4-[2-(methoxy-D3)-5-fluorophenyl]-2-hydroxy-4-methyl-2-(trifluoromethyl) pentylamino}isobenzofuran-1(3H)-one of Formula 2 (see Example 1, FIG. 2C):

(Formula 2)

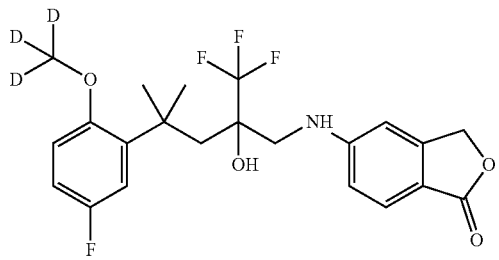

"CpdX-D3(eA)", as used herein, refers to one of the two enantiomers of the SEGRAM of Formula 2 or a pharmaceutically acceptable salt, solvate or prodrug thereof. "CpdX-D3(eA)" corresponds to the first elution peak of 5-{4-[2-(methoxy-D3)-5-fluorophenyl]-2-hydroxy-4-methyl-2-(trifluoromethyl)pentylamino}isobenzofuran-1 (3H)-one separated by preparative supercritical fluid chromatography (see Example 1, FIG. 2D).

"CpdX-D3(eB)", as used herein, refers to one of the two enantiomers of the SEGRAM of Formula 2 or a pharmaceutically acceptable salt, solvate or prodrug thereof. "CpdX-D3(eB)" corresponds to the second elution peak of 5-{4-[2-(methoxy-D3)-5-fluorophenyl]-2-hydroxy-4-methyl-2-(trifluoromethyl)pentylamino}isobenzofuran-1 (3H)-one separated by preparative supercritical fluid chromatography (see Example 1, FIG. 2D).

"Direct transactivation function of the glucocorticoid receptor (GR)" refers to the transcriptional activation of genes comprising a positive glucocorticoid response element ((+)GRE) (with SEQ ID NO: 1) bound by a glucocorticoid (GC)-associated GR in their promoter region.

"Direct transrepression function of the glucocorticoid receptor (GR)" refers to the transcriptional repression of genes comprising a negative glucocorticoid response element (nGRE) (with SEQ ID NO: 2) bound by a glucocorticoid (GC)-associated GR in their promoter region.

"Enhanced $T_h2$ activity" means that a diseased subject has an increase (e.g., at least 2-fold, 3-fold, 4-fold, 5-fold, 6-fold, 8-fold, 10-fold or more) in its $T_h2$ activity, as compared to a healthy subject. An enhanced $T_h2$ activity may be measured by an increase in the level of secreted cytokines and antibodies (e.g., IL-1β, IL-4, IL-5, IL-6, IL-10, IL-13, TSLP, IgE and IgG1) according to methods known in the art.

"Enhanced $T_h17$ activity" means that a diseased subject has an increase (e.g., at least 2-fold, 3-fold, 4-fold, 5-fold, 6-fold, 8-fold, 10-fold or more) in its $T_h17$ activity, as compared to a healthy subject. An enhanced $T_h17$ activity may be measured by an increase in the level of secreted cytokines (e.g., IL-1β, IL-6, IL-17a, IL-17c, IL-17f, IL-21, IL-22, IL-23 and TGFβ) according to methods known in the art.

"Enhanced $T_h1$ activity" means that a diseased subject has an increase (e.g., at least 2-fold, 3-fold, 4-fold, 5-fold, 6-fold, 8-fold, 10-fold or more) in its $T_h1$ activity, as compared to a healthy subject. An enhanced $T_h1$ activity may be measured by an increase in the level of secreted cytokines and antibodies (e.g., IL-1β, IL-2, IL-3, IL-6, IL-12, IL-18, IL-23, IFN-γ, TNFα and IgG2a) according to methods known in the art.

"Fatty liver", also referred to as "hepatic steatosis", as used herein, refers to a condition wherein large vacuoles of triglyceride fat accumulate in liver cells via the process of steatosis (i.e., abnormal retention of lipids within a cell). This accumulation of fat may also be accompanied by a progressive inflammation of the liver (hepatitis), called steatohepatitis.

"Growth suppression" is an important and well-recognized adverse effect of steroidal anti-inflammatory drugs (SAID) therapy, in particular in children. The mechanism of growth suppression includes, without limitation, the effect of SAIDs on the essential components of anabolism and growth including bone metabolism, nitrogen retention, and the effect on collagen formation. SAID therapies also result in inhibition of growth hormone release and insulin-like growth factor-1 (IGF-1) bioavailability. In one embodiment, growth suppression upon SAID therapy affects the whole body, with a stunted physical growth. In one embodiment, growth suppression upon SAID therapy affects internal organs, and includes, but is not limited to, thymus, spleen, kidney, liver and adrenal gland.

"Hyperglycemia" is a condition in which an excessive amount of glucose circulates in the blood plasma, such as, e.g., higher than 11.1 mmol of glucose per L of blood (200 mg of glucose per dL of blood). The American Diabetes Association guidelines classifies subjects in several subgroups, from slightly hyperglycemic (with a glucose level ranging from about 5.6 to about 7 mmol/L of blood, i.e., from about 100 to about 126 mg/dL of blood), to diabetic (with a glucose level above 7 mmol/L of blood, i.e., above 126 mg/dL of blood). The effect of SAIDs on glucose metabolism is dose-dependent and causes a mild increase in fasting blood glucose levels and a larger increase in postprandial blood glucose in patients without preexisting diabetes mellitus. SAID-induced hyperglycemia is multifactorial in origin and can be explained by the augmentation of hepatic gluconeogenesis, inhibition of glucose uptake in adipose tissue and/or alteration of receptor and post-receptor functions induced by SAIDs. Techniques to assess the development of hyperglycemia upon SAID therapy or upon administration of the SEGRAM of the present invention to a subject in need thereof are well-known from the skilled artisan, and include, without limitation, blood test with biochemical analysis and glucose test (including fasting blood sugar (FBS) test, fasting plasma glucose (FPG) test, glucose tolerance test, postprandial glucose (PG) test and random glucose test).

"Hyperinsulinemia" or "hyperinsulinism" as used herein, refers to a condition in which an excessive amount of insulin circulates in the blood plasma. Hyperinsulinemia is associated with hypertension, obesity, dyslipidemia and glucose intolerance (all collectively known as "metabolic syndrome").

"Indirect tethered transrepression function of the glucocorticoid receptor (GR)" refers to the transcriptional repression of genes comprising an AP-1 binding site (with a nucleic acid sequence ATGAGTCAT) and/or a NF-κB-binding site (with a nucleic acid sequence SEQ ID NO: 3-GGGRNNYYCC, with R being any one of G or A, Y being any one of T or C, and N being any one of A, T, C or G) in their promoter region, bound by the Jun subunit of AP-1 and/or the p65 subunit of NF-κB respectively, themselves bound by a glucocorticoid (GC)-associated GR.

"Inflammatory disorder" refers to a pathological state resulting in inflammation, e.g., caused by influx of leukocytes and/or neutrophil chemotaxis. Inflammation may result from infection with pathogenic organisms and viruses, or from noninfectious means such as, e.g., immune response to foreign antigen, autoimmune responses, trauma or reperfusion following myocardial infarction or stroke. $T_h1$, $T_h2$ and $T_h17$ cells are three subsets of T helper cells known to be involved in several inflammatory disorders. They differentiate from naïve CD4 T cells (or $T_h0$ cells) depending on their cytokine environment: IFN-γ drives $T_h1$ cell production while IL-10 and IL-4 inhibit $T_h1$ cell production; conversely, IL-4 drives $T_h2$ cell production and IFN-γ inhibits $T_h2$ cells. As to $T_h17$ cells, their production is driven by TGF-β, IL-6, IL-21, IL-23 and IL-33.

"Osteoporosis" is a progressive disease characterized by low bone mass, microarchitecture deterioration of bone tissue, bone fragility, and a consequent increase in fracture risk. Secondary osteoporosis, as the consequence of systemic drug use such as SAIDs, is one of the most debilitating complications of glucocorticoid therapy, which has been recognized since 1940. The cumulative dose as well as the duration of SAID's exposure are the key determinants in the development of osteoporosis. Inhibition of osteoblast function is the main effect of SAIDs on bone metabolism leading to a decrease in bone formation. Bone loss starts promptly after the initiation of SAID therapy and is mainly taking place in the first six months of treatment. In addition to bone loss, SAID therapy can also result in changes in the architectural integrity of the bone. Techniques to assess the development of osteoporosis upon SAID therapy or upon administration of the SEGRAM of the present invention to a subject in need thereof are well-known from the skilled artisan, and include, without limitation, measuring the bone mineral density at baseline and comparing the baseline result to subsequent measurements during and after treatment. Techniques to prevent osteoporosis are also well-known from the skilled artisan and include, without limitation, administering to a patient in need thereof a supplementation in calcium and/or vitamin D, and appropriate physical activity.

"Prodrug", as used herein, refers to the pharmacologically acceptable derivatives of the SEGRAM of the invention, preferably of the compound of Formula 1 or a derivative thereof, such as esters whose in vivo biotransformation product is the active drug. Prodrugs are characterized by increased bio-availability and are readily metabolized into the active compounds in vivo. Suitable prodrugs for the purpose of the invention include carboxylic esters (in particular alkyl esters, aryl esters, acyloxyalkyl esters and dioxolene carboxylic esters) and ascorbic acid esters.

"Reduced $T_h2$ activity" means that a diseased subject has a decrease (e.g., at least 2-fold, 3-fold, 4-fold, 5-fold, 6-fold, 8-fold, 10-fold or fewer) in its $T_h2$ response, as compared to a healthy subject. A reduced $T_h2$ activity may be measured by a decrease in the level of secreted cytokines and antibodies (e.g., IL-1β, IL-3, IL-4, IL-5, IL-6, IL-10, IL-13, TSLP, IgE and IgG1) according to methods known in the art.

"Reduced $T_h17$ activity" means that a diseased subject has a decrease (e.g., at least 2-fold, 3-fold, 4-fold, 5-fold, 6-fold, 8-fold, 10-fold or fewer) in its $T_h17$ response, as compared to a healthy subject. A reduced $T_h17$ activity may be measured by a decrease in the level of secreted cytokines (e.g., IL-1β, IL-6, IL-17a, IL-17c, IL-17f, IL-21, IL-22, IL-23 and TGFβ) according to methods known in the art.

"Reduced $T_h1$ activity" means that a diseased subject has a decrease (e.g., at least 2-fold, 3-fold, 4-fold, 5-fold, 6-fold, 8-fold, 10-fold or fewer) in its $T_h1$ response, as compared to a healthy subject. A reduced $T_h1$ activity may be measured by a decrease in the level of secreted cytokines and antibodies (e.g., IL-1β, IL-2, IL-3, IL-6, IL-12, IL-18, IL-23, IFN-γ, TNFα and IgG2a) according to methods known in the art.

"Skin atrophy", also referred as to "steroid atrophy" or "corticosteroid-induced dermal atrophy", consists of a reduction in epidermal and/or dermal thickness, regression of the sebaceous glands, subcutaneous fat loss and/or muscle-layer atrophy. It results from the SAID-driven inhibition of mitotic activity of fibroblasts and/or of collagenase, leading to a decrease in collagen and glycosaminoglycan synthesis and a reduction in the diameter of the fibrils. Techniques to assess the development of skin atrophy upon SAID therapy or upon administration of the SEGRAM of the present invention to a subject in need thereof are well-known from the skilled artisan, and include, without limitation, visual control of the skin thinning and of the vascular prominence, use of calipers (including the Harpenden skinfold caliper), gravimetric, ultrasound, soft tissue X-ray, histiometric, electrical resistivity and transcriptional analysis of the Kindlin-1 (Ussar et al., 2008. *PLoS Genet.* 4(12):e1000289) and REDD1 (Britto et al., 2014. *Am J Physiol Endocrinol Metab.* 307(11):E983-93; Baida et al., 2015. *EMBO Mol Med.* 7(1):42-58) genes.

"Solvate", as used herein, refers to a molecular complex comprising the SEGRAMs of the invention, preferably the compounds of Formula 1 or a derivative thereof and one or more pharmaceutically acceptable solvent molecules, e.g., ethanol. The term "hydrate" is employed when said solvent is water.

"Steroidal anti-inflammatory drugs (SAIDs)-associated side effects", as used herein, refers to side effects (also termed "debilitating effects") commonly observed in subjects undergoing a short-term, middle-term or long-term treatment with a steroidal anti-inflammatory drugs (SAIDs).

"$T_h2$-related inflammatory disorder" refers to any disease, disorder or condition, in which $T_h2$ cells support, cause or mediate the disease, disorder or condition process or in which $T_h2$ cells are involved in curing or alleviating the symptoms of the disease, disorder or condition, which may be represented by an enhanced or reduced $T_h2$ activity.

"$T_h17$-related inflammatory disorder" refers to any disease, disorder or condition, in which $T_h17$ cells support, cause or mediate the disease, disorder or condition process or in which $T_h17$ cells are involved in curing or alleviating the symptoms of the disease, disorder or condition, which may be represented by an enhanced or reduced $T_h17$ activity.

"$T_h1$-related inflammatory disorder" refers to any disease, disorder or condition, in which $T_h1$ cells support, cause or mediate the disease, disorder or condition process or in which $T_h1$ cells are involved in curing or alleviating the symptoms of the disease, disorder or condition, which may be represented by an enhanced or reduced $T_h1$ activity.

DETAILED DESCRIPTION

The present invention relates to methods for preventing and/or treating an inflammatory disorder comprising administering to a subject in need thereof a therapeutically effective amount of a SElective GR Agonistic Modulator (SEGRAM).

In one embodiment, the methods of the invention are for preventing and/or treating a T helper 2 cells ($T_h2$)-related inflammatory disorder. In one embodiment, the methods of the invention are for preventing and/or treating a T helper 17 cells ($T_h17$)-related inflammatory disorder. In one embodiment, the methods of the invention are for preventing and/or treating a T helper 1 cells ($T_h1$)-related inflammatory disorder.

In one embodiment, the methods of the invention are for preventing and/or treating a $T_h2$- and $T_h17$-related inflammatory disorder (also referred to as "mixed $T_h2/T_h17$ inflammatory disorder"). In one embodiment, the methods of the invention are for preventing and/or treating a $T_h1$- and $T_h17$-related inflammatory disorder (also referred to as "mixed $T_h1/T_h17$ inflammatory disorder"). In one embodiment, the methods of the invention are for preventing and/or treating a $T_h1$- and $T_h2$-related inflammatory disorder (also referred to as "mixed $T_h1/T_h2$ inflammatory disorder"). In one embodiment, the methods of the invention are for preventing and/or treating a $T_h1$-, $T_h2$- and $T_h17$-related inflammatory disorder (also referred to as "mixed $T_h1/T_h2/T_h17$ inflammatory disorder").

Inflammatory Disorders

Examples of inflammatory disorders include, without limitation, atopic dermatitis, contact dermatitis, asthma including allergic asthma, psoriasis, allergic conjunctivitis, rheumatoid arthritis, giant-cell arteritis (Horton disease), inflammatory bowel disease (IBD) (including, but not limited to, Crohn's disease, ulcerative colitis and colitis), post-menopausal-induced metabolic syndrome and steatosis, periodontitis, Pagets disease, osteoporosis, multiple myeloma, uveitis, acute myelogenous leukemia, chronic myelogenous leukemia, pancreatic β cell destruction, rheumatoid spondylitis, osteoarthritis, gouty arthritis and other arthritis conditions, gout, adult respiratory distress syndrome (ARDS), chronic pulmonary inflammatory diseases, silicosis, pulmonary sarcoidosis, rhinitis, anaphylaxis, pancreatitis, muscle degeneration, cachexia including cachexia secondary to infection, to malignancy or to acquired immune deficiency syndrome, Reiter's syndrome, type I diabetes, bone resorption disease, graft-versus-host disease (GVHD), ischemia reperfusion injury, brain trauma, multiple sclerosis, cerebral malaria, sepsis, septic shock, toxic shock syndrome, endotoxic shock, gram negative sepsis, fever and myalgias due to infection such as influenza and pyrosis.

$T_h2$-Related Inflammatory Disorders

In one embodiment, the methods of the present invention are for preventing and/or treating a $T_h2$-related inflammatory disorder. In one embodiment, $T_h2$-related inflammatory disorders include any disease, disorder or condition in which $T_h2$ cells support, cause or mediate the disease, disorder or condition process. In one embodiment, $T_h2$-related inflammatory disorders include any disease, disorder or condition, in which $T_h2$ cells are involved in curing or alleviating the symptoms of the disease, disorder or condition.

In one embodiment, a $T_h2$-related inflammatory disorder is represented by an enhanced $T_h2$ activity. In one embodiment, a $T_h2$-related inflammatory disorder is represented by a reduced $T_h2$ activity.

$T_h2$-related inflammatory disorders include, but are not limited to, allergic diseases and infectious diseases (particularly extracellular infections).

$T_h2$-related allergic diseases encompassed within the present invention include, but are not limited to, atopic dermatitis, allergic asthma, allergic sinusitis, allergic conjunctivitis, allergic rhinitis, rhinoconjunctivitis, hay fever, solar dermatitis, eczema, urticaria, angioedema, erythema nodosum, erythema multiforme, cutaneous necrotizing venulitis, insect bite skin inflammation and anaphylaxis.

In one embodiment, the methods of the invention are for preventing and/or treating atopic dermatitis (see Example 5).

In one embodiment, the methods of the invention are for preventing and/or treating allergic asthma (see Example 6).

In one embodiment, the methods of the invention are for preventing and/or treating allergic conjunctivitis (see Example 10).

$T_h17$-Related Inflammatory Disorders

In one embodiment, the methods of the present invention are for preventing and/or treating a $T_h17$-related inflammatory disorder. In one embodiment, $T_h17$-related inflammatory disorders include any disease, disorder or condition in which $T_h17$ cells support, cause or mediate the disease, disorder or condition process. In one embodiment, $T_h17$-related inflammatory disorders include any disease, disorder or condition, in which $T_h17$ cells are involved in curing or alleviating the symptoms of the disease, disorder or condition.

In one embodiment, a $T_h17$-related inflammatory disorder is represented by an enhanced $T_h17$ activity. In one embodiment, a $T_h17$-related inflammatory disorder is represented by a reduced $T_h17$ activity.

$T_h17$-related inflammatory disorders include, but are not limited to, autoimmune diseases and proliferative disorders (e.g., cancer).

$T_h17$-related autoimmune diseases encompassed within the present invention include, but are not limited to, contact dermatitis, psoriasis, rheumatoid arthritis, inflammatory bowel disease (IBD) (including, but not limited to, Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease.

In one embodiment, the methods of the invention are for preventing and/or treating contact dermatitis (see Example 3).

In one embodiment, the methods of the invention are for preventing and/or treating psoriasis (see Example 7).

In one embodiment, the methods of the invention are for preventing and/or treating rheumatoid arthritis (see Example 8).

In one embodiment, the methods of the invention are for preventing and/or treating colitis (see Example 9).

In one embodiment, the methods of the invention are for preventing and/or treating periodontitis.

$T_h1$-Related Inflammatory Disorders

In one embodiment, the methods of the present invention are for preventing and/or treating a $T_h1$-related inflammatory disorder. In one embodiment, $T_h1$-related inflammatory disorders include any disease, disorder or condition in which $T_h1$ cells support, cause or mediate the disease, disorder or condition process. In one embodiment, $T_h1$-related inflammatory disorders include any disease, disorder or condition, in which $T_h1$ cells are involved in curing or alleviating the symptoms of the disease, disorder or condition.

In one embodiment, a $T_h1$-related inflammatory disorder is represented by an enhanced $T_h1$ activity. In one embodiment, a $T_h1$-related inflammatory disorder is represented by a reduced $T_h1$ activity.

$T_h1$-related inflammatory disorders include, but are not limited to, infectious diseases (particularly intracellular infections such as, e.g., viral infections) and proliferative disorders (e.g., cancer).

Methods for Measuring Cytokines/Ig Levels

Methods for measuring an increase or decrease in the level of secreted cytokines and antibodies are well-known from the skilled artisan, and include, without limitation, histologic analysis and analysis of cytokine and/or immunoglobulin profiles.

Cytokines and/or immunoglobulin profiles may be measured by conventional methods using anti-cytokine (such as, e.g., anti-IL-1β, anti-IL-2, anti-IL-3, anti-IL-4, anti-IL-5, anti-IL-6, anti-IL-10, anti-IL-12, anti-IL-13, anti-IL-17a, anti-IL-17c, anti-IL-17f, anti-IL-18, anti-IL-21, anti-IL-22, anti-IL-23, anti-IL-33, anti-IFN-γ, anti-TNFα, anti-TGFβ or anti-TSLP) and/or anti-isotype antibodies (such as, e.g., anti-IgA, anti-IgE, anti-IgG1, anti-IgG2a, anti-IgG2b, anti-IgG3 or anti-IgM antibodies) in a flow cytometry assay, ELISA assay, sandwich ELISA assay, ELISPOT assay or the like. Other methods to measure a cytokine profile include, but are not limited to, reverse transcription polymerase chain reaction (RT-PCR), including real-time polymerase chain reaction (RT-PCR), quantitative reverse transcription polymerase chain reaction (q-RT-PCR) and the like.

Properties of the SEGRAMs of the Invention

Function on GR

In one embodiment, the SEGRAM of the present invention does not induce or does not substantially induce the direct transactivation function of the glucocorticoid receptor (GR).

By "does not induce the direct transactivation function of the glucocorticoid receptor (GR)" is meant that upon binding of the SEGRAM of the present invention to GR, the transcription level of genes comprising a positive glucocorticoid response element ((+)GRE) is not higher than their transcription level before binding of the SEGRAM of the present invention to GR. In other words, upon binding of the SEGRAM of the present invention to GR, the transcription of genes comprising a positive glucocorticoid response element ((+)GRE) is not increased as compared to before binding of the SEGRAM of the present invention to GR.

By "does not substantially induce the direct transactivation function of the glucocorticoid receptor (GR)" is meant that upon binding of the SEGRAM of the present invention to GR, the transcription level of genes comprising a positive glucocorticoid response element ((+)GRE) is not higher than three times, twice, 1.8 times, 1.6 times, 1.5 times, 1.4 times, 1.3 times, 1.2 times, 1.1 times or less their transcription level before binding of the SEGRAM of the present invention to GR. In other words, upon binding of the SEGRAM of the present invention to GR, the transcription of genes comprising a positive glucocorticoid response element ((+)GRE) is not increased by more than three-fold, two-fold, 1.8-fold, 1.6-fold, 1.5-fold, 1.4-fold, 1.3-fold, 1.2-fold, 1.1-fold or less as compared to before binding of the SEGRAM of the present invention to GR.

In one embodiment, the SEGRAM of the present invention does not induce or does not substantially induce the direct transrepression function of the GR.

By "does not induce the direct transrepression function of the GR" is meant that upon binding of the SEGRAM of the present invention to GR, the transcription level of genes comprising a negative glucocorticoid response element (nGRE) is not lower than their transcription level before binding of the SEGRAM of the present invention to GR. In other words, upon binding of the SEGRAM of the present invention to GR, the transcription of genes comprising a negative glucocorticoid response element (nGRE) is not decreased as compared to before binding of the SEGRAM of the present invention to GR.

By "does not substantially induce the direct transrepression function of the GR" is meant that upon binding of the SEGRAM of the present invention to GR, the transcription level of genes comprising a negative glucocorticoid response element (nGRE) is not lower than three times, twice, 1.8 times, 1.6 times, 1.5 times, 1.4 times, 1.3 times, 1.2 times, 1.1 times or less their transcription level before binding of the SEGRAM of the present invention to GR. In other words, upon binding of the SEGRAM of the present invention to GR, the transcription of genes comprising a negative glucocorticoid response element (nGRE) is not decreased by more than three-fold, two-fold, 1.8-fold, 1.6-fold, 1.5-fold, 1.4-fold, 1.3-fold, 1.2-fold, 1.1-fold or less as compared to before binding of the SEGRAM of the present invention to GR.

In one embodiment, the SEGRAM of the present invention does not induce or does not substantially induce neither direct transactivation, nor direct transrepression functions of the GR.

In one embodiment, the SEGRAM of the present invention selectively induces the indirect tethered transrepression function of the GR.

Function on $T_h$ Cells

Function on $T_h2$ Cells

In one embodiment, the SEGRAM of the invention inhibits or substantially inhibits $T_h2$ cells differentiation from $T_h0$ cells.

By "inhibits $T_h2$ cells differentiation from $T_h0$ cells" is meant that upon binding of the SEGRAM of the invention to GR, the number of $T_h2$ cells is not higher than their number before binding of the SEGRAM of the present invention to GR. In one embodiment, the number of $T_h2$ cells is lower than their number before binding of the SEGRAM of the present invention to GR. In one embodiment, the number of $T_h2$ cells is 1.1 times, 1.2 times, 1.5 times, twice, 3 times, 5 times, 10 times, 25 times, 50 times, 100 times or more lower than their number before binding of the SEGRAM of the present invention to GR.

By "substantially inhibits $T_h2$ cells differentiation from $T_h0$ cells" is meant that upon binding of the SEGRAM of the invention to GR, the number of $T_h2$ cells is not higher than twice, 1.8 times, 1.6 times, 1.5 times, 1.4 times, 1.3 times, 1.2 times, 1.1 times or less their number before binding of the SEGRAM of the present invention to GR.

In one embodiment, the SEGRAM of the invention inhibits or substantially inhibits the production of any one or more of the cytokines selected from the group comprising or consisting of IL-4, IL-5, IL-10, IL-13 and TSLP. In one embodiment, the SEGRAM of the invention inhibits or substantially inhibits the production of any one or more of the immunoglobulins selected from the group comprising or consisting of IgE and IgG1.

By "inhibits the production of any one or more of the cytokines" and "inhibits the production of any one or more of the immunoglobulins" is meant that upon binding of the SEGRAM of the invention to GR, the expression level of said cytokines or immunoglobulins is not higher than their expression level before binding of the SEGRAM of the present invention to GR. In one embodiment, the expression level of said cytokines or immunoglobulins is lower than their expression level before binding of the SEGRAM of the present invention to GR. In one embodiment, the expression level of said cytokines or immunoglobulins is 1.1 times, 1.2 times, 1.5 times, twice, 3 times, 5 times, 10 times, 25 times, 50 times, 100 times or more lower than their expression level before binding of the SEGRAM of the present invention to GR.

By "substantially inhibits the production of any one or more of the cytokines" and "substantially inhibits the production of any one or more of the immunoglobulins" is meant that upon binding of the SEGRAM of the invention to GR, the expression level of said cytokines or immunoglobulins is not higher than twice, 1.8 times, 1.6 times, 1.5 times, 1.4 times, 1.3 times, 1.2 times, 1.1 times or less their expression level to before binding of the SEGRAM of the present invention to GR.

Function on $T_h17$ Cells

In one embodiment, the SEGRAM of the invention inhibits or substantially inhibits $T_h17$ cells differentiation from $T_h0$ cells.

By "inhibits $T_h17$ cells differentiation from $T_h0$ cells" is meant that upon binding of the SEGRAM of the invention to GR, the number of $T_h17$ cells is not higher than their number before binding of the SEGRAM of the present invention to GR. In one embodiment, the number of $T_h17$ cells is lower than their number before binding of the SEGRAM of the present invention to GR. In one embodiment, the number of $T_h17$ cells is 1.1 times, 1.2 times, 1.5 times, twice, 3 times, 5 times, 10 times, 25 times, 50 times, 100 times or more lower than their number before binding of the SEGRAM of the present invention to GR.

By "substantially inhibits $T_h17$ cells differentiation from $T_h0$ cells" is meant that upon binding of the SEGRAM of the invention to GR, the number of $T_h17$ cells is not higher than twice, 1.8 times, 1.6 times, 1.5 times, 1.4 times, 1.3 times, 1.2 times, 1.1 times or less their number before binding of the SEGRAM of the present invention to GR.

In one embodiment, the SEGRAM of the invention inhibits or substantially inhibits the production of any one or more of the cytokines selected from the group comprising or consisting of IL-17a, IL-17c, IL-17f, IL-21, IL-22, IL-23 and TGFβ.

By "inhibits the production of any one or more of the cytokines" is meant that upon binding of the SEGRAM of the invention to GR, the expression level of said cytokines is not higher than their expression level before binding of the SEGRAM of the present invention to GR. In one embodiment, the expression level of said cytokines is lower than their expression level before binding of the SEGRAM of the present invention to GR. In one embodiment, the expression level of said cytokines is 1.1 times, 1.2 times, 1.5 times, twice, 3 times, 5 times, 10 times, 25 times, 50 times, 100 times or more lower than their expression level before binding of the SEGRAM of the present invention to GR.

By "substantially inhibits the production of any one or more of the cytokines" is meant that upon binding of the SEGRAM of the invention to GR, the expression level of said cytokines is not higher than twice, 1.8 times, 1.6 times, 1.5 times, 1.4 times, 1.3 times, 1.2 times, 1.1 times or less their expression level to before binding of the SEGRAM of the present invention to GR.

Function on $T_h1$ Cells

In one embodiment, the SEGRAM of the invention inhibits or substantially inhibits $T_h1$ cells differentiation from $T_h0$ cells.

By "inhibits $T_h1$ cells differentiation from $T_h0$ cells" is meant that upon binding of the SEGRAM of the invention to GR, the number of $T_h1$ cells is not higher than their number before binding of the SEGRAM of the present invention to GR. In one embodiment, the number of $T_h1$ cells is lower than their number before binding of the SEGRAM of the present invention to GR. In one embodiment, the number of $T_h1$ cells is 1.1 times, 1.2 times, 1.5 times, twice, 3 times, 5 times, 10 times, 25 times, 50 times, 100 times or more lower than their number before binding of the SEGRAM of the present invention to GR.

By "substantially inhibits $T_h1$ cells differentiation from $T_h0$ cells" is meant that upon binding of the SEGRAM of the invention to GR, the number of $T_h1$ cells is not higher than twice, 1.8 times, 1.6 times, 1.5 times, 1.4 times, 1.3 times, 1.2 times, 1.1 times or less their number before binding of the SEGRAM of the present invention to GR.

In one embodiment, the SEGRAM of the invention inhibits or substantially inhibits the production of any one or more of the cytokines selected from the group comprising or consisting of IL-2, IL-12, IL-18, IFN-γ and TNFα. In one embodiment, the SEGRAM of the invention inhibits or substantially inhibits the production of any one or more of the immunoglobulins selected from the group comprising or consisting of IgG2a.

By "inhibits the production of any one or more of the cytokines" and "inhibits the production of any one or more of the immunoglobulins" is meant that upon binding of the SEGRAM of the invention to GR, the expression level of said cytokines or immunoglobulins is not higher than their expression level before binding of the SEGRAM of the present invention to GR. In one embodiment, the expression level of said cytokines or immunoglobulins is lower than their expression level before binding of the SEGRAM of the present invention to GR. In one embodiment, the expression level of said cytokines or immunoglobulins is 1.1 times, 1.2 times, 1.5 times, twice, 3 times, 5 times, 10 times, 25 times, 50 times, 100 times or more lower than their expression level before binding of the SEGRAM of the present invention to GR.

By "substantially inhibits the production of any one or more of the cytokines" and "substantially inhibits the production of any one or more of the immunoglobulins" is meant that upon binding of the SEGRAM of the invention to GR, the expression level of said cytokines or immunoglobulins is not higher than twice, 1.8 times, 1.6 times, 1.5 times, 1.4 times, 1.3 times, 1.2 times, 1.1 times or less their expression level to before binding of the SEGRAM of the present invention to GR.

Side Effects

In one embodiment, the SEGRAM of the invention does not induce or does not substantially induce side effects upon administration to a subject in need thereof.

In one embodiment, the SEGRAM of the invention does not induce or does not substantially induce steroidal anti-inflammatory drugs (SAIDs)-associated side effects upon administration to a subject in need thereof.

Examples of SAIDs include, but are not limited to, natural glucocorticoids and synthetic glucocorticoids. Examples of natural glucocorticoids include, without limitation, cortisone, cortodoxone, desoxycortone, hydrocortisone, prebediolone acetate and pregnenolone. Synthetic glucocorticoids include, without limitation, alclometasone, amcinonide, beclomethasone, betamethasone, budesonide, chloroprednisone, chloroprednisone, ciclesonide, clobetasol, clobetasone, clocortolone, cloprednol, cortivazol, deflazacort, desonide, desoximetasone, dexamethasone, diflorasone, diflucortolone, difluprednate, fluclorolone, fluclorolone, fludrocortisone, fludroxycortide, flugestoneacetate, flumetasone, flunisolide, fluocinolone, fluocinonide, fluocortin, fluocortolone, fluorometholone, fluperolone, fluprednidene, fluprednisolone, fluticasone, formocortal, halcinonide, halometasone, loteprednol, medrysone, meprednisone, methylprednisolone, mometasone, paramethasone, prednicarbate, prednisolone, prednisoneandtixocortol, prednylidene, rimexolone, triamcinolone, triamcinolone and ulobetasol.

Examples of SAIDs-associated side effects include, but are not limited to, musculoskeletal side effects, endocrine and metabolic side effects, gastrointestinal side effects, cardiovascular side effects, dermatologic side effects, neuropsychiatric side effects, ophthalmologic side effects and immunologic side effects.

SAIDs-associated musculoskeletal side effects include, but are not limited to, osteoporosis, avascular necrosis of bone and myopathy.

SAIDs-associated endocrine and metabolic side effects include, but are not limited to, metabolic syndrome; growth suppression; body weight loss; fat mass gain; lean mass loss; thymus, spleen, kidney and/or adrenal gland apoptosis; corticosterone synthesis inhibition; adrenal suppression; hyperglycemia; insulin resistance; hyperinsulinemia; type 2 diabetes; dyslipidemia; fatty liver; and cushingoid features.

SAIDs-associated gastrointestinal side effects include, but are not limited to, gastritis, peptic ulcer, gastrointestinal bleeding, visceral perforation and pancreatitis.

SAIDs-associated cardiovascular side effects include, but are not limited to, hypertension, coronary heart disease, ischemic heart disease and heart failure.

SAIDs-associated dermatologic side effects include, but are not limited to, skin atrophy, dermatoporosis, ecchymoses, purpura, erosions, striae, delayed wound healing, easy bruising, acne, hirsutism and hair loss.

SAIDs-associated neuropsychiatric side effects include, but are not limited to, mood changes, depression, euphoria, mood lability, irritability, akathisia, anxiety, cognitive impairment, psychosis, dementia and delirium.

SAIDs-associated ophthalmologic side effects include, but are not limited to, cataract, glaucoma, ptosis, mydriasis, opportunistic ocular infections and central serous chorioretinopathy.

SAIDs-associated immunologic side effects include, but are not limited to, suppression of cell-mediated immunity, predisposition to infections and reactivation of latent infections.

In one embodiment, the SEGRAM of the invention does not induce or does not substantially induce any one or more of a SAIDs-associated side effect selected from the group comprising or consisting of osteoporosis; avascular necrosis of bone; myopathy; metabolic syndrome; growth suppression; body weight loss; fat mass gain; lean mass loss; thymus, spleen, kidney and/or adrenal gland apoptosis; corticosterone synthesis inhibition; adrenal suppression; hyperglycemia; insulin resistance; hyperinsulinemia; type 2 diabetes; dyslipidemia; fatty liver; gastritis; peptic ulcer; gastrointestinal bleeding; visceral perforation; hepatic steatosis; pancreatitis; hypertension; coronary heart disease; ischemic heart disease; heart failure; skin atrophy; dermatoporosis; ecchymoses; purpura; erosions; striae; delayed wound healing; easy bruising; acne; hirsutism; hair loss; mood changes; depression; euphoria; mood lability; irritability; akathisia; anxiety; cognitive impairment; psychosis; dementia; delirium; cataract; glaucoma; ptosis; mydriasis; opportunistic ocular infections; central serous chorioretinopathy; suppression of cell-mediated immunity; predisposition to infections and reactivation of latent infections.

In one embodiment, the SEGRAM of the invention does not induce or does not substantially induce any one or more of a SAIDs-associated side effect selected from the group comprising or consisting of skin atrophy; osteoporosis;

growth suppression; body weight loss; fat mass gain; lean mass loss; thymus, spleen, kidney and/or adrenal gland apoptosis; corticosterone synthesis inhibition; adrenal suppression; hyperglycemia; insulin resistance; hyperinsulinemia; and fatty liver.

In one embodiment, the SEGRAM of the present invention does not induce skin atrophy upon administration to a subject in need thereof (see Example 11).

In one embodiment, the SEGRAM of the present invention does not induce osteoporosis upon administration to a subject in need thereof (see Example 12).

In one embodiment, the SEGRAM of the present invention does not induce growth suppression upon administration to a subject in need thereof (see Example 13).

In one embodiment, the SEGRAM of the present invention does not induce body weight loss upon administration to a subject in need thereof (see Example 13).

In one embodiment, the SEGRAM of the present invention does not induce fat mass gain and/or lean mass loss upon administration to a subject in need thereof (see Example 13).

In one embodiment, the SEGRAM of the present invention does not induce thymus, spleen, kidney and/or adrenal gland apoptosis upon administration to a subject in need thereof (see Example 14).

In one embodiment, the SEGRAM of the present invention does not induce corticosterone synthesis inhibition upon administration to a subject in need thereof (see Example 15).

In one embodiment, the SEGRAM of the present invention does not induce adrenal suppression upon administration to a subject in need thereof (see Example 15).

In one embodiment, the SEGRAM of the present invention does not induce hyperglycemia upon administration to a subject in need thereof (see Example 16).

In one embodiment, the SEGRAM of the present invention does not induce insulin resistance upon administration to a subject in need thereof (see Example 17).

In one embodiment, the SEGRAM of the present invention does not induce hyperinsulinemia, upon administration to a subject in need thereof (see Example 17).

In one embodiment, the SEGRAM of the present invention does not induce fatty liver upon administration to a subject in need thereof (see Example 18).

Structure

In one embodiment, the SEGRAMs according to the present invention are either one or the two enantiomers of a compound of Formula 1 or a derivative thereof:

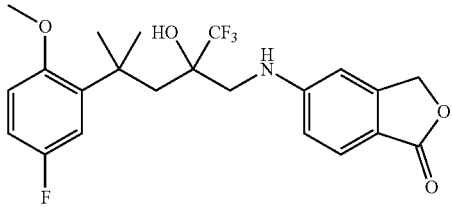

(Formula 1)

or a pharmaceutically acceptable deuterated form, salt, solvate and/or prodrug thereof.

As used herein, the compound of Formula 1 is a 5-[4-(5-fluoro-2-methoxyphenyl)-2-hydroxy-4-methyl-2-(trifluoromethyl)pentylamino]-isobenzofuran-1(3H)-one and is referred to as "CpdX".

In one embodiment, the compound of Formula 1 is the racemic (R/S)-5-[4-(5-fluoro-2-methoxyphenyl)-2-hydroxy-4-methyl-2-(trifluoromethyl)pentylamino]-isobenzofuran-1(3H)-one. In one embodiment, each of the two enantiomers of the compound of Formula 1 are obtained by separation of a racemic mixture of the compound of Formula 1 or a derivative thereof by supercritical fluid chromatography (SFC), said two enantiomers corresponding to the first elution peak [CpdX(eA)] and to the second elution peak [CpdX(eB)], respectively.

SFC is a technique well-known from the one skilled in the art. In one embodiment, each enantiomer of the compound of Formula 1 can be efficiently purified by SFC using an amylose tris-(3,5-dimethylphenylcarbamate) column.

In one embodiment, the compound of Formula 1 is deuterated. In one embodiment, at least one hydrogen atom in the compound of Formula 1 is deuterated. In one embodiment, at least 2, 3, 4, 5, 6, 7, 8, 9, 10, 11, 12, 13, 14, 15, 16, 17, 18, 19, 20 or 21 hydrogen atoms in the compound of Formula 1 are deuterated.

In one embodiment, three hydrogen atoms in the compound of Formula 1 are deuterated. Accordingly, in one embodiment, a deuterated form of Formula 1 is a compound of Formula 2 or a pharmaceutically acceptable enantiomer, salt, solvate and/or prodrug thereof, and is referred to as "CpdX-D3":

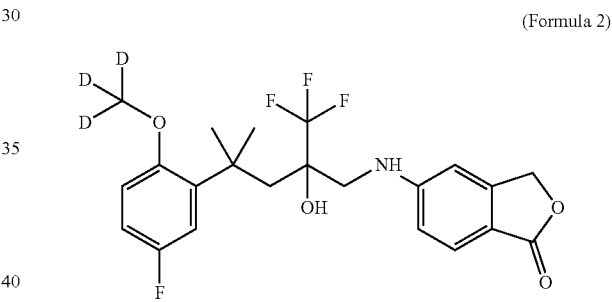

(Formula 2)

In one embodiment, the compound of Formula 2 is the racemic (R/S)-5-{4-[2-(methoxy-$D_3$)-5-fluorophenyl]-2-hydroxy-4-methyl-2-(trifluoro-methyl)-pentylamino}-isobenzofuran-1(3H)-one. In one embodiment, the two enantiomers of the compound of Formula 2 are obtained by separation of a racemic mixture of the compound of Formula 2 or a derivative thereof by supercritical fluid chromatography (SFC), said two enantiomers corresponding to the first elution peak [CpdX-D3(eA)] and to the second elution peak [CpdX-D3(eB)], respectively.

SFC is a technique well-known from the one skilled in the art. In one embodiment, each enantiomer of the compound of Formula 2 can be efficiently purified by SFC using an amylose tris-(3,5-dimethylphenylcarbamate) column.

In the following, any reference to a compound of Formula 1 also includes compounds of Formula 2 as defined hereinabove, unless explicitly mentioned otherwise.

In one embodiment, a derivative of the compound of Formula 1 comprises compounds disclosed in U.S. Pat. No. 6,245,804.

In one embodiment, the compound of Formula 1 is comprised in the possible compounds derived from Formula 3.

In one embodiment, a derivative of a compound of Formula 1 is a compound of Formula 3:

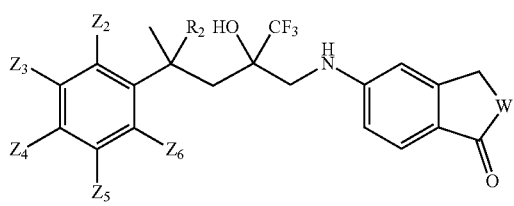

(Formula 3)

wherein:
W is selected from 0, S or $CH_2$;
$R_2$ is selected from H or $CH_3$; and
$Z_2, Z_3, Z_4, Z_5$ and $Z_6$ are each independently selected from H, F, Cl, Br, $CH_3$, $OCH_3$, $CH_2CH_3$, $CH_2CH_2CH_3$, $CH(CH_3)_2$, $C(CH_3)_3$, $COCH_3$, $NO_2$, CN, $CH=CH_2$ or $CONH_2$,
or a pharmaceutically acceptable enantiomer, deuterated form, salt, solvate and/or prodrug thereof.

In one embodiment, the compound of Formula 3 is deuterated. In one embodiment, at least one hydrogen atom in the compound of Formula 3 is deuterated. In one embodiment, at least 2, 3, 4, 5, 6, 7, 8, 9, 10, 11, 12, 13, 14, 15, 16, 17, 18, 19, 20 or more hydrogen atoms in the compound of Formula 3 are deuterated.

In a specific embodiment, when the compound of Formula 3 is deuterated, $Z_2$ is selected from D, $CD_3$, $OCD_3$, $CH_2CD_3$, $CH_2CH_2CD_3$, $CH(CD_3)_2$, $C(CD_3)_3$, $COCD_3$ or $CH=CD_2$.

In a specific and preferred embodiment, when the compound of Formula 3 is deuterated, $Z_2$ is $OCD_3$.

Pharmaceutically acceptable salts of the SEGRAM of the invention, preferably of the compound of Formula 1 or a derivative thereof, include the acid addition and base salts thereof.

Suitable acid addition salts are formed from acids which form non-toxic salts. Examples include, but are not limited to, acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include, but are not limited to, aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts.

Hemisalts of acids and bases may also be formed, for example, hemisulphate and hemicalcium salts.

Preferably, pharmaceutically acceptable salts include, but are not limited to, hydrochloride/chloride, hydrobromide/bromide, bisulphate/sulphate, nitrate, citrate and acetate.

Pharmaceutically acceptable salts of the SEGRAM of the invention, preferably of the compound of Formula 1 or a derivative thereof, may be prepared by one or more of these methods:

(i) by reacting the SEGRAM of the invention, preferably the compound of Formula 1 or a derivative thereof, with the desired acid;
(ii) by reacting the SEGRAM of the invention, preferably the compound of Formula 1 or a derivative thereof, with the desired base;
(iii) by removing an acid- or base-labile protecting group from a suitable precursor of the SEGRAM of the invention, preferably of the compound of Formula 1 or a derivative thereof; or by ring-opening a suitable cyclic precursor, for example, a lactone or lactam, using the desired acid; or
(iv) by converting one salt of the SEGRAM of the invention, preferably of the compound of Formula 1 or a derivative thereof, to another by reaction with an appropriate acid or by means of a suitable ion exchange column.

All these reactions are typically carried out in solution. The salt may precipitate from solution and be collected by filtration or may be recovered by evaporation of the solvent. The degree of ionization in the salt may vary from completely ionized to almost non-ionized.

All references to the SEGRAM of the invention, preferably to the compound of Formula 1 or a derivative thereof, include references to enantiomers, deuterated forms, salts, solvates, multicomponent complexes and liquid crystals thereof, as well as combinations of these.

The compounds of the invention include the SEGRAM of the invention, preferably the compound of Formula 1 or a derivative thereof, as herein defined, including all polymorphs and crystal habits thereof, prodrugs and isomers thereof (including optical, geometric and tautomeric isomers) and isotopically-labeled compounds.

In addition, although generally, with respect to the salts, pharmaceutically acceptable salts are preferred, it should be noted that the invention in its broadest sense also included non-pharmaceutically acceptable salts, which may for example be used in the isolation and/or purification of the SEGRAM of the invention, preferably of the compound of Formula 1 or a derivative thereof. For example, salts formed with optically active acids or bases may be used to form diastereoisomeric salts that can facilitate the separation of optically active isomers of the SEGRAM of the invention, preferably of the compound of Formula 1 or a derivative thereof.

The invention also generally covers all pharmaceutically acceptable predrugs and prodrugs of the SEGRAM of the invention, preferably of the compound of Formula 1 or a derivative thereof.

Enantiomers

The present invention also relates to either one or the two enantiomers of a compound of Formula 1 or a derivative thereof:

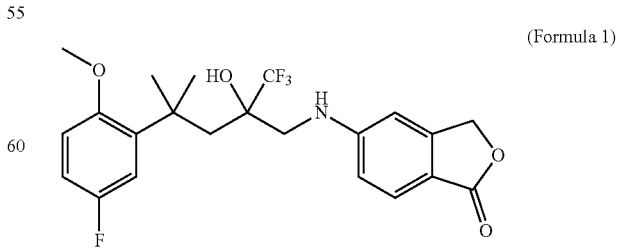

(Formula 1)

or a pharmaceutically acceptable deuterated form, salt, solvate and/or prodrug thereof.

In one embodiment, the enantiomers of a compound of Formula 1 or a derivative thereof are de novo synthetized (Example 1, FIG. 2A).

In one embodiment, the enantiomers of a compound of Formula 1 or a derivative thereof are obtained by separation the two racemic components present in the compound of Formula 1 or a derivative thereof (Example 1, FIG. 2B).

In one embodiment, the separation of the two racemic components is carried out by supercritical fluid chromatography (SFC). SFC is a technique well-known from the one skilled in the art. In this embodiment, each enantiomer of the compound of Formula 1 or a derivative thereof can be efficiently separated by SFC using an amylose tris-(3,5-dimethylphenylcarbamate) column.

In one embodiment in which a racemic mixture of a compound of Formula 1 or a derivative thereof is separated by SFC, the first elution peak is referred as to "CpdX(eA)", whereas the second elution peak is referred as to "CpdX (eB)".

Deuterated SEGRAMs

The present invention also relates to a deuterated form of a compound of Formula 1 or a derivative thereof:

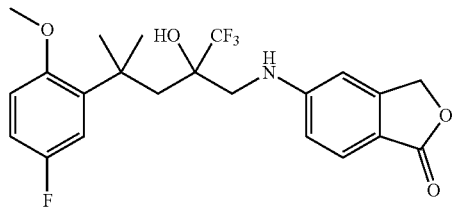

(Formula 1)

or a pharmaceutically acceptable enantiomer, salt, solvate and/or prodrug thereof.

In one embodiment, the deuterated form of a compound of Formula 1 comprises at least one deuterated hydrogen atom. In one embodiment, the deuterated form of a compound of Formula 1 comprises at least 2, 3, 4, 5, 6, 7, 8, 9, 10, 11, 12, 13, 14, 15, 16, 17, 18, 19, 20 or 21 deuterated hydrogen atoms.

In one embodiment, the deuterated form of a compound of Formula 1 comprises three deuterated hydrogen atoms. Accordingly, in one embodiment, the deuterated form of a compound of Formula 1 is a compound of Formula 2 or a pharmaceutically acceptable enantiomer, salt, solvate and/or prodrug thereof, and is referred to as "CpdX-D3":

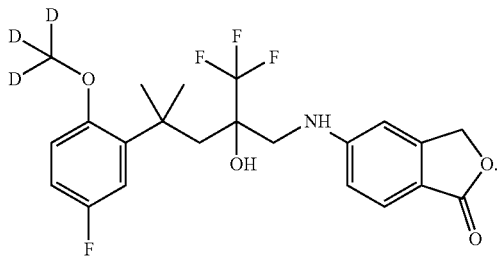

(Formula 2)

Deuterated Enantiomers

The present invention also relates to either one or the two enantiomers of a compound of Formula 2 or a derivative thereof:

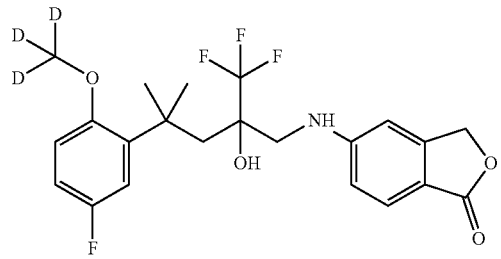

(Formula 2)

or a pharmaceutically acceptable salt, solvate and/or prodrug thereof.

In one embodiment, the enantiomers of a compound of Formula 2 or a derivative thereof are de novo synthetized (Example 1, FIG. 2C).

In one embodiment, the enantiomers of a compound of Formula 2 or a derivative thereof are obtained by separation the two racemic components present in the compound of Formula 2 or a derivative thereof (Example 1, FIG. 2D).

In some embodiments, the separation of the two racemic components is carried out by supercritical fluid chromatography (SFC). SFC is a technique well-known from the one skilled in the art. In one embodiment, each enantiomer of the compound of Formula 2 or a derivative thereof can be efficiently separated by SFC using an amylose tris-(3,5-dimethylphenylcarbamate) column.

In one embodiment in which a racemic mixture of a compound of Formula 2 or a derivative thereof is separated by SFC, the first elution peak is referred as to "CpdX-D3 (eA)", whereas the second elution peak is referred as to "CpdX-D3(eB)".

Compositions

Composition

The present invention also relates to a composition comprising or consisting of or consisting essentially of the SEGRAM of the invention, preferably a compound of Formula 1 or a derivative thereof.

The present invention also relates to a composition for preventing or treating, or for use in preventing or treating an inflammatory disorder in a subject in need thereof, comprising or consisting of or consisting essentially of the SEGRAM of the invention, preferably a compound of Formula 1 or a derivative thereof.

The present invention also relates to a composition for preventing or treating, or for use in preventing or treating a $T_h1$-, $T_h2$- and/or $T_h17$-related inflammatory disorder in a subject in need thereof, comprising or consisting of or consisting essentially of the SEGRAM of the invention, preferably a compound of Formula 1 or a derivative thereof.

Pharmaceutical Composition

The present invention also relates to a pharmaceutical composition comprising or consisting of or consisting essentially of the SEGRAM of the invention, preferably a compound of Formula 1 or a derivative thereof, in combination with at least one pharmaceutically acceptable excipient.

The present invention also relates to a pharmaceutical composition for preventing or treating, or for use in preventing or treating an inflammatory disorder in a subject in need thereof, comprising or consisting of or consisting essentially of the SEGRAM of the invention, preferably a compound of Formula 1 or a derivative thereof, and at least one pharmaceutically acceptable excipient.

The present invention also relates to a pharmaceutical composition for preventing or treating, or for use in preventing or treating a $T_h1$-, $T_h2$- and/or $T_h17$-related inflammatory disorder in a subject in need thereof, comprising or consisting of or consisting essentially of the SEGRAM of the invention, preferably a compound of Formula 1 or a derivative thereof, and at least one pharmaceutically acceptable excipient.

Pharmaceutically acceptable excipients include, but are not limited to, water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, e.g., BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, some pharmaceutically acceptable excipients may include, surfactants (e.g., hydroxypropylcellulose); suitable carriers, such as, e.g., solvents and dispersion media containing, e.g., water, ethanol, polyol (e.g., glycerol, propylene glycol, and liquid polyethylene glycol, and the like), suitable mixtures thereof, and vegetable oils, such as, e.g., peanut oil and sesame oil; isotonic agents, such as, e.g., sugars or sodium chloride; coating agents, such as, e.g., lecithin; agents delaying absorption, such as, e.g., aluminum monostearate and gelatin; preservatives, such as, e.g., benzalkonium chloride, benzethonium chloride, chlorobutanol, thimerosal and the like; buffers, such as, e.g., boric acid, sodium and potassium bicarbonate, sodium and potassium borates, sodium and potassium carbonate, sodium acetate, sodium biphosphate and the like; tonicity agents, such as, e.g., dextran 40, dextran 70, dextrose, glycerin, potassium chloride, propylene glycol, sodium chloride; antioxidants and stabilizers, such as, e.g., sodium bisulfite, sodium metabisulfite, sodium thiosulfite, thiourea and the like; nonionic wetting or clarifying agents, such as, e.g., polysorbate 80, polysorbate 20, poloxamer 282 and tyloxapol; viscosity modifying agents, such as, e.g., dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

Medicament

The present invention also relates to a medicament comprising or consisting of or consisting essentially of the SEGRAM of the invention, preferably a compound of Formula 1 or a derivative thereof.

The present invention also relates to a medicament for preventing or treating, or for use in preventing or treating an inflammatory disorder in a subject in need thereof, wherein said medicament comprises or consists of or consists essentially of the SEGRAM of the invention, preferably a compound of Formula 1 or a derivative thereof.

The present invention also relates to a medicament for preventing or treating, or for use in preventing or treating a $T_h1$-, $T_h2$- and/or $T_h17$-related inflammatory disorder in a subject in need thereof, wherein said medicament comprises or consists of or consists essentially of the SEGRAM of the invention, preferably a compound of Formula 1 or a derivative thereof.

Cosmeceutical Composition

The present invention also relates to a cosmeceutical composition comprising or consisting of or consisting essentially of the SEGRAM of the invention, preferably a compound of Formula 1 or a derivative thereof.

The present invention also relates to a cosmeceutical composition for preventing or treating, or for use in preventing or treating an inflammatory disorder in a subject in need thereof, wherein said medicament comprises or consists of or consists essentially of the SEGRAM of the invention, preferably a compound of Formula 1.

Administration Modes

In one embodiment, the composition, pharmaceutical composition, medicament or cosmeceutical composition of the invention is to be administered systemically or locally.

In one embodiment, the composition, pharmaceutical composition, medicament or cosmeceutical composition of the invention is to be administered orally, by injection, topically, transdermally, subcutaneously, transmucosally, percutaneously, nasally (such as, e.g., by intranasal spray or drops), buccally, sublingually, ocularly, intraaurally, intratracheally, endoscopically, intraarticularly, intraarterially, intramedullarly, intrathecally, intraventricularly, intraperitoneally, enterally, rectally or vaginaly.

Injection

In one embodiment, the composition, pharmaceutical composition, medicament or cosmeceutical composition of the invention is injected, preferably systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal and intraperitoneal injection, and perfusion. In another embodiment, when injected, the composition, the pharmaceutical composition or the medicament of the invention is sterile. Methods for obtaining a sterile pharmaceutical composition include, but are not limited to, GMP synthesis (GMP stands for "Good manufacturing practice").

Oral Administration

In another embodiment, the composition, pharmaceutical composition, medicament or cosmeceutical composition of the invention is orally administered.

Examples of formulations adapted to oral administration include, but are not limited to, solid forms, liquid forms and gels.

Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet.

Examples of liquid form adapted to oral administration include, but are not limited to, solutions, suspensions, drinkable solutions, elixirs, sealed phial, potion, drench, syrup and liquor.

Topical Administration

In another embodiment, the composition, pharmaceutical composition, medicament or cosmeceutical composition of the invention is topically administered.

Topical administration characterizes the delivery, administration or application of the composition, pharmaceutical composition, medicament or cosmeceutical composition of the invention directly to the site of interest for a localized effect (generally onto one or more exposed or outer surfaces thereof, such as the outermost layer of the epidermis, which is exposed and visually observable), e.g., using hands, fingers or a wide variety of applicators (roll-up, roll-on or other stick container, tube container, cotton ball, powder puff, Q-tip, pump, brush, mat, cloth and/or the like). The application may be made, e.g., by laying, placing, rubbing, sweeping, pouring, spreading and/or massaging into, or onto, the skin, or by any other convenient or suitable method. Preferably, topical administration is effected without any significant absorption of components of the composition into the subject's blood stream (to avoid a systemic effect).

Examples of formulations adapted to topical administration include, but are not limited to, sticks, lipsticks, waxes, creams, lotions, ointments, balms, gels, glosses, sunscreen preparations, cosmetics, masks, leave-on washes or cleansers, depilatory preparations and/or the like.

The composition, pharmaceutical composition, medicament or cosmeceutical composition of the invention of the invention can be mixed to form white, smooth, homogeneous, opaque cream or lotion with, e.g., benzyl alcohol 1% or 2% (w/w) as a preservative, emulsifying wax, glycerin, isopropyl palmitate, lactic acid, purified water and sorbitol solution. In addition, the compositions can contain polyethylene glycol 400 (PEG 400). They can be mixed to form ointments with, e.g., benzyl alcohol 2% (w/w) as preservative, white petrolatum, emulsifying wax and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application.

In one embodiment, formulations adapted to topical administration comprise about 0.001% w/w, preferably about 0.005% w/w, 0.01% w/w, 0.02% w/w, 0.03% w/w, 0.04% w/w, 0.05% w/w, 0.06% w/w, 0.07% w/w, 0.08% w/w, 0.09% w/w, 0.1% w/w, 0.2% w/w, 0.3% w/w, 0.4% w/w, 0.5% w/w, 0.6% w/w, 0.7% w/w, 0.8% w/w, 0.9% w/w, 1.0% w/w or more of the compound of Formula 1 or a derivative thereof.

Transdermal Administration

In another embodiment, the composition, pharmaceutical composition, medicament or cosmeceutical composition of the invention can also be applied topically using a transdermal system, such as one of an acrylic-based polymer adhesive with a resinous crosslinking agent impregnated with the composition and laminated to an impermeable backing.

In one embodiment, the composition, pharmaceutical composition, medicament or cosmeceutical composition of the invention can be administered as a transdermal patch, more particularly as a sustained-release transdermal patch. The transdermal patches can include any conventional form such as, e.g., adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, e.g., U.S. Pat. Nos. 5,262,165, 5,948,433, 6,010,715 and 6,071,531, the disclosure of each of which are incorporated herein in their entirety.

Examples of formulations adapted to transdermal administration include, but are not limited to, ointment, paste, cream, film, balm, patch, such as, e.g., transdermal patch, gel, liposomal forms and the like.

In one embodiment, the composition, pharmaceutical composition, medicament or cosmeceutical composition of the invention is an ointment, paste, cream; film, balm, patch, such as, e.g., transdermal patch, gel, liposomal forms or the like.

In one embodiment of the invention, the ointment is an oleaginous ointment; an emulsified ointment such as, e.g., oil-in-water or a water-in-oil ointment; or a water-soluble ointment, preferably is an oleaginous ointment.

In one embodiment of the invention, the oleaginous ointment uses bases such as, e.g., plant and animal oils; plant and animal fats; waxes; vaseline, such as, e.g., white vaseline or vaseline oil; and paraffin such as, e.g., liquid paraffin or paraffin oil.

In one embodiment of the invention, the transdermal composition further comprises one or more excipients. Suitable pharmaceutically acceptable excipients are well known from the skilled person. Examples of suitable excipients include, but are not limited to, carriers, emulsifying agents, stiffening agents, rheology modifiers or thickeners, surfactants, emollients, preservatives, humectants, buffering agents, solvents, moisturizing agents and stabilizers.

Ocular Administration

In another embodiment, the composition, pharmaceutical composition, medicament or cosmeceutical composition of the invention can also be applied intraocularly. In one embodiment, administration of the composition, pharmaceutical composition, medicament or cosmeceutical composition of the invention may be a topical ocular administration, such as, e.g., the administration of eye drops or by bathing the eye in an ophthalmic solution comprising the inhibitor of the invention.

An ophthalmic solution refers to sterile liquid, semi-solid or solid preparations intended for administration upon the eyeball and/or to the conjunctiva, or for insertion in the conjunctival sac or for administration into the posterior segment of the eye. As used herein, the term "posterior segment of the eye" refers to the back two third of the eye, comprising the anterior hyaloids membrane and the structures behind it (vitreous humor, retina, choroid, optic nerve).

In particular, an ophthalmic composition may be administered into the vitreous, e.g., by intravitreous injection. Examples of ophthalmic compositions include, but are not limited to, eye drops, eye lotions, powders for eye drops and powders for eye lotions, and compositions to be injected into the conjunctival sac or into the vitreous.

Examples of carriers include, but are not limited to, water; buffered saline; petroleum jelly (Vaseline, also known as white soft paraffin); petrolatum; oils, such as, e.g., mineral oil, vegetable oil, animal oil, paraffin oil, castor oil or vaseline oil; organic and inorganic waxes, such as, e.g., microcrystalline, paraffin, bees wax and ozocerite wax; natural polymers, such as, e.g., xanthanes, gelatin, cellulose, collagen, starch, or gum arabic; synthetic polymers; alcohols; polyols; and the like. In one embodiment of the invention, the carrier is a base cream, comprising an emulsifying agent, an oil-phase ingredient and a water phase ingredient.

Examples of ointment- or lotion-base excipients include, but are not limited to, Vaseline, Plastibase™ (which is a base prepared with polyethylene (average molecular weight of about 21000 Da) and liquid paraffin) and ESMA-P™ (made of microcrystalline wax).

Examples of emulsifying agents include, but are not limited to, cetyl alcohol, cetostearyl alcohol, stearyl alcohol, carboxypolymethylene, polycarbophil, polyethylene glycol and derivatives thereof, polyoxyethylene and derivatives thereof, such as, e.g., polysorbate 20 or polysorbate 80, alone or in combination with fatty alcohols such as, e.g., cetyl alcohol, stearyl alcohol and cetostearyl alcohol, and sorbitan esters, such as, e.g., sorbitan fatty acid ester.

Examples of oil-phase ingredient include, but are not limited to, Vaseline, such as, e.g., white Vaseline, yellow Vaseline or Vaseline oil, paraffin such as, e.g., liquid paraffin or paraffin oil, dimethicone and mixtures thereof.

Examples of water-phase ingredients include, but are not limited to, water, glycerol and propyleneglycol.

Examples of stiffening agents include, but are not limited to, stearyl alcohol, cetostearyl alcohol, and cetyl alcohol.

Examples of rheology modifiers or thickeners include, but are not limited to, carbomers such as, e.g., Carbopol®, and polyoxyethylene tallow amines such as, e.g., Ethomeen®.

Examples of surfactants include, but are not limited to, anionic, cationic, amphoteric, and nonionic surfactants, such as, e.g., sodium lauryl sulfate, cetostearyl alcohol, cetyl alcohol, magnesium lauryl sulfate, a wax, or a combination thereof.

Examples of emollients include, but are not limited to, white or yellow petrolatum (white or yellow vaseline), liquid petrolatum (liquid vaseline), paraffin, or aquaphor.

Examples of preservatives include, but are not limited to, antimicrobial preservatives such as, e.g., nipagin (methyl hydroxybenzoate), nipasol (hydroxybenzoate), butylparaben, ethylparaben, methylparaben, propyl paraben potassium, propyl paraben sodium, parahydroxybenzoate esters, sorbic acid, potassium sorbate, benzoic acid, parabens, chlorobutanol, phenol, thimerosal, sodium benzoate and benzyl alcohol.

Examples of humectants include, but are not limited to, propylene glycol and propylene glycol alginate.

Examples of buffering agents include, but are not limited to, sodium hydroxide, citric acid and potassium hydroxide.

Examples of solvents include, but are not limited to, water, isopropanol, benzyl alcohol, and propylene glycol.

Examples of moisturizing agents include, but are not limited to, glycerin, mineral oil, polyoxyethylene hardened castor oil and Vaseline, propylene glycol, paraffins, waxes, such as, e.g., bees wax, polyethylene glycols or mixtures thereof, such as, e.g., macrogol (macrogol is a mixture of polyethylene glycols of different molecular weights), stearyl alcohol, benzyl alcohol, parahydrobenzoate esters (parabens), gelled hydrocarbon, citric acid, squalene, lanolins, glycerin, polyoxyethylene hardened castor oil, sorbitan fatty ester, glycerin fatty ester, animal and vegetable fats, oils, starch, tragacanth, cellulose derivatives, silicones, bentonites, silicic acid, talc, zinc oxide and mixtures thereof.

Examples of stabilizers include, but are not limited to, carbohydrates such as, e.g., sucrose, lactose and trehalose, sugar alcohols such as, e.g., mannitol and sorbitol, amino acids such as, e.g., histidine, glycine, phenylalanine and arginine.

Respiratory Administration

In another embodiment, the composition, pharmaceutical composition, medicament or cosmeceutical composition of the invention is to be administered by respiratory administration, including nasally (such as, e.g., by spray) and buccally.

In one embodiment, the composition, pharmaceutical composition, medicament or cosmeceutical composition of the invention may be delivered by any of a variety of inhalation devices known in the art for administration of a therapeutic agent by inhalation.

These devices include metered dose inhalers, nebulizers, dry powder inhalers, sprayers, and the like.

Some specific examples of commercially available inhalation devices suitable for the practice of this invention are Cyclohaler, Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), the Respimat® soft mist inhaler (Boehringer Ingelheim) or the like.

As those skilled in the art will recognize, the formulation of the composition, pharmaceutical composition, medicament or cosmeceutical composition of the invention, the quantity of the formulation delivered and the duration of administration of a single dose depend on the type of inhalation device employed.

For some aerosol delivery systems, such as nebulizers, the frequency of administration and length of time for which the system is activated will depend mainly on the concentration of the composition, pharmaceutical composition, medicament or cosmeceutical composition of the invention in the aerosol. For example, shorter periods of administration can be used at higher concentrations of the composition, pharmaceutical composition, medicament or cosmeceutical composition of the invention in the nebulizer solution.

Devices such as metered dose inhalers can produce higher aerosol concentrations, and can be operated for shorter periods to deliver the desired amount of the composition, pharmaceutical composition, medicament or cosmeceutical composition of the invention.

Devices such as powder inhalers deliver active agent until a given charge of agent is expelled from the device. In this type of inhaler, the amount of the composition, pharmaceutical composition, medicament or cosmeceutical composition of the invention in a given quantity of the powder determines the dose delivered in a single administration.

In one embodiment, particles of the composition, pharmaceutical composition, medicament or cosmeceutical composition of the invention delivered by inhalation have a particle size preferably less than about 10 µm, more preferably in the range of about 1 µm to about 5 µm.

Advantageously, for administration as a dry powder, the composition, pharmaceutical composition, medicament or cosmeceutical composition of the invention is prepared in a particulate form with a particle size of less than about 10 µm, preferably about 1 to about 5 µm. Such formulations may be achieved by spray drying, milling, micronisation or critical point condensation of the composition, pharmaceutical composition, medicament or cosmeceutical composition of the invention.

Formulations of the composition, pharmaceutical composition, medicament or cosmeceutical composition of the invention for administration from a dry powder inhaler typically include a finely divided dry powder containing the composition, pharmaceutical composition, medicament or cosmeceutical composition of the invention, but the powder can also include a bulking agent, carrier, excipient, another additive, or the like. Examples of additives include, but are not limited to, mono-, di-, and polysaccharides; sugar alcohols and other polyols, such as, e.g., lactose, glucose, raffinose, melezitose, lactitol, maltitol, trehalose, sucrose, mannitol, starch, inulin, or combinations thereof; surfactants, such as sorbitols, dipalmitoylphosphatidyl choline, or lecithin; or the like.

A spray including the composition, pharmaceutical composition, medicament or cosmeceutical composition of the invention can be produced by forcing the composition, pharmaceutical composition, medicament or cosmeceutical composition of the invention through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Formulations of the composition, pharmaceutical composition, medicament or cosmeceutical composition of the invention suitable for use with a sprayer will typically include the composition, pharmaceutical composition, medicament or cosmeceutical composition of the invention in an aqueous solution.

Intraarticular Administration

In another embodiment, the composition, pharmaceutical composition, medicament or cosmeceutical composition of the invention is to be administered intraarticularly.

In one embodiment, the composition, pharmaceutical composition, medicament or cosmeceutical composition of the invention may be delivered within the joint of a subject in need thereof. For example, the composition, pharmaceutical composition, medicament or cosmeceutical composition of the invention can be administered by intra-disc or peri-disc administration to a subject having an inflammatory disorder with back pain. For example, the composition, pharmaceutical composition, medicament or cosmeceutical composition of the invention can be administered by inter-knee or peri-knee injection to a subject having an inflammatory disorder with knee pain.

Sustained-Released Administration

In one embodiment, the composition, pharmaceutical composition, medicament or cosmeceutical composition of the invention is to be administered in a sustained-release form. In another embodiment, the composition, the pharmaceutical composition or the medicament comprises a delivery system that controls the release of the modulator.

Subject

In one embodiment, the subject is an animal. In one embodiment, the subject is a mammal.

Examples of mammals include, but are not limited to, primates (including human and non-human), cattle (including cows), horses, pigs, sheep, goats, dogs and cats.

In a preferred embodiment, the subject is a human.

In one embodiment, the subject is an adult (e.g., a subject above the age of 18 in human years or a subject after reproductive capacity has been attained). In another embodiment, the subject is a child (for example, a subject below the age of 18 in human years or a subject before reproductive capacity has been attained).

In one embodiment, the subject is a male. In one embodiment, the subject is a female.

In one embodiment, the subject is/was diagnosed with an inflammatory disorder, preferably with a $T_h1$-, $T_h2$- and/or $T_h17$-related inflammatory disorder. In one embodiment, the subject is/was diagnosed with any one of the $T_h1$-, $T_h2$- and/or $T_h17$-related inflammatory disorders selected from the group comprising or consisting of atopic dermatitis, contact dermatitis, allergic asthma, allergic sinusitis, allergic conjunctivitis, allergic rhinitis, rhinoconjunctivitis, giant-cell arteritis (Horton disease), hay fever, solar dermatitis, eczema, urticaria, angioedema, erythema nodosum, erythema multiforme, cutaneous necrotizing venulitis, insect bite skin inflammation, anaphylaxis, psoriasis, rheumatoid arthritis, inflammatory bowel disease (IBD) (including, but not limited to, Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease.

In one embodiment, the subject is/was diagnosed with any one of the $T_h1$-, $T_h2$- and/or $T_h17$-related inflammatory disorders selected from the group comprising or consisting of atopic dermatitis, contact dermatitis, allergic asthma, psoriasis, rheumatoid arthritis and inflammatory bowel disease (IBD) (including, but not limited to, Crohn's disease, ulcerative colitis and colitis.

In one embodiment, the subject is at risk of developing an inflammatory disorder, preferably with a $T_h1$-, $T_h2$- and/or $T_h17$-related inflammatory disorder. In one embodiment, the subject is at risk of developing any one of the $T_h1$-, $T_h2$- and/or $T_h17$-related inflammatory disorders selected from the group comprising or consisting of atopic dermatitis, contact dermatitis, allergic asthma, allergic sinusitis, allergic conjunctivitis, allergic rhinitis, rhinoconjunctivitis, giant-cell arteritis (Horton disease), hay fever, solar dermatitis, eczema, urticaria, angioedema, erythema nodosum, erythema multiforme, cutaneous necrotizing venulitis, insect bite skin inflammation, anaphylaxis, psoriasis, rheumatoid arthritis, inflammatory bowel disease (IBD) (including, but not limited to, Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease.

In one embodiment, the subject is at risk of developing any one of the $T_h1$-, $T_h2$- and/or $T_h17$-related inflammatory disorders selected from the group comprising or consisting of atopic dermatitis, contact dermatitis, allergic asthma, psoriasis, allergic conjunctivitis, rheumatoid arthritis and inflammatory bowel disease (IBD) (including, but not limited to, Crohn's disease, ulcerative colitis and colitis).

Regimen

In one embodiment, the composition, pharmaceutical composition, medicament or cosmeceutical composition of the invention is to be administered at a dose determined by the skilled artisan and personally adapted to each subject.

It will be understood that the total daily usage of the composition, pharmaceutical composition, medicament or cosmeceutical composition of the present invention will be decided by the attending physician within the scope of sound medical judgment. The specific therapeutically effective amount for any particular subject will depend upon a variety of factors including the disease being treated and the severity of the disease; the specific composition employed, the age, body weight, general health, sex and diet of the subject; the time of administration, route of administration, the duration of the treatment; drugs used in combination or coincidental with the composition, pharmaceutical composition, medicament or cosmeceutical composition of the invention; and like factors well known in the medical arts. For example, it is well within the skill of the art to start doses of a therapeutic compound at levels lower than those required to achieve the desired therapeutic effect and to gradually increase the dosage until the desired effect is achieved; but, at the opposite, it can be equally useful to start with a loading dose, a manner to reach steady-state plasma concentration more quickly, and then to follow with a maintenance dose calculated to exactly compensate the effect of the elimination process.

In one embodiment, a therapeutically effective amount of the composition, pharmaceutical composition, medicament or cosmeceutical composition of the invention is to be administered at least once a day, at least twice a day, at least three times a day.

In one embodiment, a therapeutically effective amount of the composition, pharmaceutical composition, medicament or cosmeceutical composition of the invention is to be administered every two, three, four, five, six days.

In one embodiment, a therapeutically effective amount of the composition, pharmaceutical composition, medicament or cosmeceutical composition of the invention is to be administered twice a week, every week, every two weeks, once a month.

In one embodiment, a therapeutically effective amount of the composition, pharmaceutical composition, medicament or cosmeceutical composition of the invention is to be administered every month, every two months, every three months, every four months, every five months, every six months, once a year.

In one embodiment, a therapeutically effective amount of the composition, pharmaceutical composition, medicament or cosmeceutical composition of the invention is to be administered for a period of time of about one day, two days, three days, four days, five days, six days, a week, two weeks, three weeks, a month, two months, three months, six months, a year, or over longer periods such as, e.g., for several years or for the rest of the life of the subject. In one embodiment, a therapeutically effective amount of the composition, pharmaceutical composition, medicament or cosmeceutical composition of the invention is to be administered until treatment or alleviation of the inflammatory disorder, preferably of the $T_h1$-, $T_h2$- and/or $T_h17$-related inflammatory disorder.

In one embodiment, a therapeutically effective amount of the composition, pharmaceutical composition, medicament or cosmeceutical composition of the invention is to be administered for a chronic treatment. In another embodiment, a therapeutically effective amount of the composition, pharmaceutical composition, medicament or cosmeceutical composition of the invention is to be administered for an acute treatment.

Regimen in Mass/Body Weight/Day

In one embodiment, the daily amount of the compound of Formula 1 or a derivative thereof to be administered to a subject in need thereof ranges from about 0.5 μg/kg to about 50 mg/kg, preferably from about 5 μg/kg to about 25 mg/kg, preferably from about 50 μg/kg to about 5 mg/kg, preferably from about 250 μg/kg to about 2.5 mg/kg, preferably from about 300 μg/kg to about 1 mg/kg, preferably from about 350 μg/kg to about 800 μg/kg, preferably from about 400 μg/kg to about 600 μg/kg. In one embodiment, the daily amount of the compound of Formula 1 or a derivative thereof to be administered to a subject in need thereof is about 500 μg/kg.

In one embodiment, the daily amount of the compound of Formula 1 or a derivative thereof to be administered to a subject in need thereof ranges from about 1 μg/kg to about 100 mg/kg, preferably from about 10 μg/kg to about 50 mg/kg, preferably from about 100 μg/kg to about 10 mg/kg, preferably from about 500 μg/kg to about 5 mg/kg, preferably from about 750 μg/kg to about 2.5 mg/kg, preferably from about 800 μg/kg to about 2 mg/kg, preferably from about 900 μg/kg to about 1.5 mg/kg. In one embodiment, the daily amount of the compound of Formula 1 or a derivative thereof to be administered to a subject in need thereof is about 1 mg/kg.

In one embodiment, the daily amount of the compound of Formula 1 or a derivative thereof to be administered to a subject in need thereof ranges from about 5 μg/kg to about 500 mg/kg, preferably from about 50 μg/kg to about 250 mg/kg, preferably from about 500 μg/kg to about 50 mg/kg, preferably from about 1 mg/kg to about 25 mg/kg, preferably from about 1.5 mg/kg to about 12.5 mg/kg, preferably from about 2 mg/kg to about 10 mg/kg, preferably from about 2.5 mg/kg to about 7.5 mg/kg. In one embodiment, the daily amount of the compound of Formula 1 or a derivative thereof to be administered to a subject in need thereof is about 5 mg/kg.

In one embodiment, the daily human-equivalent amount of the compound of Formula 1 or a derivative thereof to be administered to a subject in need thereof ranges from about 0.5 μg/kg to about 250 μg/kg, preferably from about 1 μg/kg to about 200 μg/kg, preferably from about 5 μg/kg to about 150 μg/kg, preferably from about 10 μg/kg to about 100 μg/kg, preferably from about 25 μg/kg to about 75 μg/kg, preferably from about 30 μg/kg to about 50 μg/kg. In one embodiment, the daily human-equivalent amount of the compound of Formula 1 or a derivative thereof to be administered to a subject in need thereof is about 40 μg/kg.

In one embodiment, the daily human-equivalent amount of the compound of Formula 1 or a derivative thereof to be administered to a subject in need thereof ranges from about 0.1 μg/kg to about 10 mg/kg, preferably from about 1 μg/kg to about 1 mg/kg, preferably from about 10 μg/kg to about 500 μg/kg, preferably from about 20 μg/kg to about 450 μg/kg, preferably from about 30 μg/kg to about 400 μg/kg, preferably from about 40 μg/kg to about 350 μg/kg, preferably from about 45 μg/kg to about 300 μg/kg, preferably from about 50 μg/kg to about 250 μg/kg, preferably from about 55 μg/kg to about 200 μg/kg, preferably from about 60 μg/kg to about 150 μg/kg, preferably from about 65 μg/kg to about 100 μg/kg, preferably from about 70 μg/kg to about 90 μg/kg. In one embodiment, the daily human-equivalent amount of the compound of Formula 1 or a derivative thereof to be administered to a subject in need thereof is about 80 μg/kg.

In one embodiment, the daily human-equivalent amount of the compound of Formula 1 or a derivative thereof to be administered to a subject in need thereof ranges from about 1 μg/kg to about 5 mg/kg, preferably from about 10 μg/kg to about 2.5 mg/kg, preferably from about 25 μg/kg to about 2 mg/kg, preferably from about 50 μg/kg to about 1 mg/kg, preferably from about 100 μg/kg to about 750 μg/kg, preferably from about 150 μg/kg to about 600 μg/kg, preferably from about 200 μg/kg to about 600 μg/kg, preferably from about 250 μg/kg to about 550 μg/kg, preferably from about 300 μg/kg to about 500 μg/kg, preferably from about 350 μg/kg to about 450 μg/kg, preferably from about 380 μg/kg to about 420 μg/kg. In one embodiment, the daily human-equivalent amount of the compound of Formula 1 or a derivative thereof to be administered to a subject in need thereof is about 400 μg/kg.

Regimen in Mass/Day

In one embodiment, the daily amount of the compound of Formula 1 or a derivative thereof to be administered to a subject in need thereof ranges from about 0.05 μg to about 250 µg, from about 0.1 µg to about 150 µg, from about 0.2 µg to about 100 µg, from about 0.3 µg to about 50 µg, from about 0.4 µg to about 35 µg, from about 0.5 µg to about 25 µg, from about 2.5 µg to about 20 µg, preferably from about 5 µg to about 15 µg. In one embodiment, the daily amount of the compound of Formula 1 or a derivative thereof to be administered to a subject in need thereof is about 10 µg.

In one embodiment, the daily amount of the compound of Formula 1 or a derivative thereof to be administered to a subject in need thereof ranges from about 0.1 µg to about 500 µg, from about 0.2 µg to about 300 µg, from about 0.4 µg to about 200 µg, from about 0.6 µg to about 100 µg, from about 0.8 µg to about 75 µg, from about 1 µg to about 50 µg, from about 5 µg to about 40 µg, preferably from about 10 µg to about 30 µg. In one embodiment, the daily amount of the compound of Formula 1 or a derivative thereof to be administered to a subject in need thereof is about 20 µg.

In one embodiment, the daily amount of the compound of Formula 1 or a derivative thereof to be administered to a subject in need thereof ranges from about 0.5 µg to about 500 µg, preferably from about 1 µg to about 250 µg, preferably from about 10 µg to about 200 µg, preferably from about 25 µg to about 180 µg, preferably from about 50 µg to about 160 µg, preferably from about 60 µg to about 140 µg, preferably from about 80 µg to about 120 µg. In one embodiment, the daily amount of the compound of Formula 1 or a derivative thereof to be administered to a subject in need thereof is about 100 µg.

In one embodiment, the daily human-equivalent amount of the compound of Formula 1 or a derivative thereof to be administered to a subject in need thereof ranges from about 50 µg to about 25 mg, preferably from about 50 µg to about 15 mg, preferably from about 100 µg to about 12.5 mg, preferably from about 200 µg to about 10 mg, preferably from about 300 µg to about 7.5 mg, preferably from about 400 µg to about 5 mg, preferably from about 500 µg to about 4.5 mg, preferably from about 1 mg to about 4 mg, preferably from about 1.5 mg to about 3.5 mg, preferably from about 2 mg to about 3 mg. In one embodiment, the daily human-equivalent amount of the compound of Formula 1 or a derivative thereof to be administered to a subject in need thereof is about 2.5 mg.

In one embodiment, the daily human-equivalent amount of the compound of Formula 1 or a derivative thereof to be administered to a subject in need thereof ranges from about 0.1 mg to about 50 mg, preferably from about 0.1 mg to about 30 mg, preferably from about 0.2 mg to about 25 mg, preferably from about 0.4 mg to about 20 mg, preferably from about 0.6 mg to about 15 mg, preferably from about 0.8 mg to about 10 mg, preferably from about 1 mg to about 9 mg, preferably from about 2 mg to about 8 mg, preferably from about 3 mg to about 7 mg, preferably from about 4 mg to about 6 mg. In one embodiment, the daily human-equivalent amount of the compound of Formula 1 or a derivative thereof to be administered to a subject in need thereof is about 5 mg.

In one embodiment, the daily human-equivalent amount of the compound of Formula 1 to be administered to a subject in need thereof ranges from about 0.5 mg to about 100 mg, preferably from about 0.6 mg to about 75 mg, preferably from about 0.8 mg to about 60 mg, preferably from about 1 mg to about 55 mg, preferably from about 2.5 mg to about 50 mg, preferably from about 5 mg to about 45 mg, preferably from about 10 mg to about 40 mg, preferably from about 15 mg to about 35 mg, preferably from about 20 mg to about 30 mg, preferably from about 23 mg to about 27 mg. In one embodiment, the daily human-equivalent amount of the compound of Formula 1 or a derivative thereof to be administered to a subject in need thereof is about 25 mg.

Combination Therapy

In one embodiment, the composition, pharmaceutical composition, medicament or cosmeceutical composition of the invention may be administered as part of a combination therapy. Thus, are included within the scope of the present invention embodiments comprising the co-administration of, and compositions and medicaments which comprise, in addition to the SEGRAM of the invention, preferably a compound of Formula 1 or a derivative thereof, additional therapeutic agents and/or active ingredients.

Such multiple drug regimens, often referred to as combination therapy, may be used for preventing or treating an inflammatory disorder, preferably for preventing or treating a $T_h1$-, $T_h2$- and/or $T_h17$-related inflammatory disorder.

In addition to the requirement of therapeutic efficacy, which may necessitate the use of active agents in addition to the SEGRAM of the invention, there may be additional rationales which compel or highly recommend the use of combinations of drugs involving active ingredients which represent adjunct therapy, i.e., which complement and supplement the function performed by the SEGRAM of the present invention.

Suitable supplementary therapeutic agents used for the purpose of auxiliary treatment include drugs which, instead of directly preventing or treating an inflammatory disorder, preferably preventing or treating a $T_h1$-, $T_h2$- and/or $T_h17$-related inflammatory disorder, treat diseases or conditions which directly result from or indirectly accompany the basic or underlying inflammatory disorder, preferably $T_h1$-, $T_h2$- and/or $T_h17$-related inflammatory disorder.

Therefore, the composition, pharmaceutical composition, medicament or cosmeceutical composition of the invention may be administered in the form of monotherapy, but may also be used in the form of multiple therapy in which the SEGRAM according to the present invention is co-administered in combination with one or more other therapeutic agents.

Examples of other active agents that may be administered in combination with the composition, pharmaceutical composition, medicament or cosmeceutical composition of the invention include but are not limited to:

(i) steroidal anti-inflammatory drugs (SAIDs), including:
  a. natural glucocorticoids, such as, e.g., cortisone, cortodoxone, desoxycortone, hydrocortisone, prebediolone acetate and pregnenolone;
  b. synthetic glucocorticoids, such as, e.g., alclometasone, amcinonide, beclomethasone, betamethasone, budesonide, chloroprednisone, chloroprednisone, ciclesonide, clobetasol, clobetasone, clocortolone, cloprednol, cortivazol, deflazacort, desonide, desoximetasone, dexamethasone, diflorasone, diflucortolone, difluprednate, fluclorolone, fluclorolone, fludrocortisone, fludroxycortide, flugestoneacetate, flumetasone, flunisolide, fluocinolone, fluocinonide, fluocortin, fluocortolone, fluorometholone, fluperolone, fluprednidene, fluprednisolone, fluticasone, formocortal, halcinonide, halometasone, loteprednol, medrysone, meprednisone, methylprednisolone, mometasone, paramethasone, prednicarbate, prednisolone, prednisoneandtixocortol, prednylidene, rimexolone, triamcinolone, triamcinolone and ulobetasol;

(ii) non-steroidal anti-inflammatory drugs (NSAIDs), including:

a. TNFα inhibitors, such as, e.g., infliximab, adalimumab, certolizumab pegol, golimumab, etanercept, thalidomide, lenalidomide and pomalidomide;
b. salicylates, such as, e.g., amoxiprin, aspirin, benorylate, diflunisal, faislamine, mesalamine and methyl salicylate;
c. bronchodilatators, such as, e.g.,
   i. β$_2$-adrenergic agonists, such as, e.g., abediterol, arformoterol, bambuterol, clenbuterol, formoterol, indacaterol, olodaterol, protokylol, salmefamol, salmeterol and vilanterol;
   ii. anticholinergics, such as, e.g., atropine, benztropine, biperiden, chlorpheniramine, dicyclomine, dimenhydrinate, diphenhydramine, doxepin, doxylamine, glycopyrrolate, ipratropium, orphenadrine, oxitropium, oxybutynin, propantheline bromide, tolterodine, tiotropium, tricyclic antidepressants, trihexyphenidyl, scopolamine, solifenacin, tropicamide, bupropion, dextromethorphan, doxacurium, hexamethonium, mecamylamine and tubocurarine; and
   iii. leukotrienes modifiers, such as, e.g., 2-TEDC, baicalein, BW-A4C, BW-B70C, caffeic acid, cinnamyl-3,4-dihydroxy-α-cyanocinnamate (CDC), CJ-13610, curcumin, fenleuton, hyperforin, *Hypericum perforatum*, meclofenamate, minocycline, N-stearoyldopamine, timegadine, zileuton, AM-103, AM-679, BAYx1005, MK-591, MK-886, 3-methoxytropolone, luteolin, PD-146176, acebilustat, captopril, DG-051, fosinoprilat, JNJ-26993135, SA-6541, SC-57461A, ubenimex, 17-octadecynoic acid, azelastine, acivicin, serine-borate complex, and cilastatin;
d. arylalkanoic acids, such as, e.g., 2-arylpropionic acids, diclofenac, indomethacin and sulindac;
e. profens, such as, e.g., carprofen, fenoprofen, flurbiprofen, ibuprofen, ketoprofen, ketorolac, loxoprofen, naproxen and tiaprofenic acid;
f. N-arylanthranilic acids, such as, e.g., fenamic acids, mefenamic acid and meclofenamic acid;
g. pyrazolidine derivatives, such as, e.g., phenylbutazone and oxyphenylbutazone;
h. oxicams, such as, e.g., meloxicam and piroxicam;
i. coxibs, such as, e.g., celecoxib, etoricoxib, parecoxib, rofecoxib and valdecoxib;
j. sulphonanilides, such as, e.g., nimesulide;
k. lipoxygenase inhibitors, such as, e.g., baicalein, caffeic acid, eicosatetraynoic acid, eicosatriynoic acid, escletin, flubiprofen, gossypol, 5-hydroxyeicosatetraenoic (HETE) lactone, 5(S)-HETE and nordihydroguaiaretic acid;
l. macrolide derivatives, such as, e.g., 9-(S)-dihydroerythromycin derivatives;
m. anti-inflammatory peptide (also called antiflamins), such as, e.g., peptides derived from seminal vesicle proteins, selectin-binding peptides, cationic peptides based on bactericidal/permeability-increasing protein BPI and IL-2 derived peptides;
n. anti-inflammatory cytokines, such as, e.g., IL-1Ra, IL-4, IL-6, IL-10, IL-11 and IL-13;
o. pro-inflammatory cytokines inhibitors, such as, e.g., TNFα inhibitors and IL-18 inhibitors);
p. galectins, such as, e.g., galectin-1;
q. antibodies neutralizing pro-inflammatory signaling molecules/cytokines, such as, e.g., antibodies against TNFα, IL-1, IL-18; and
r. statins.

The above combinations include combinations of the composition, pharmaceutical composition, medicament or cosmeceutical composition of the invention not only with one other active agent but also with two or more active agents.

In one embodiment, the composition, pharmaceutical composition, medicament or cosmeceutical composition of the invention and the other therapeutic active agents may be administered:
   in terms of dosage forms either separately or in conjunction with each other, and
   in terms of their time of administration, either serially or simultaneously.

Thus, the administration of the composition, pharmaceutical composition, medicament or cosmeceutical composition of the invention may be prior to, concurrent with, or subsequent to the administration of the other active agents.

Methods and Uses
Methods of Treatment

The present invention further relates to a method for preventing and/or treating an inflammatory disorder in a subject in need thereof, comprising administering to the subject a therapeutically effective amount of a SElective GR Agonistic Modulator (SEGRAM). The present invention further relates to a method for preventing and/or treating an inflammatory disorder in a subject in need thereof, comprising administering to the subject a therapeutically effective amount of the composition, pharmaceutical composition, medicament or cosmeceutical composition according to the invention.

The present invention further relates to a method for preventing and/or treating an enhanced $T_h1$, $T_h2$ and/or $T_h17$ activity in a subject in need thereof, comprising administering to the subject a therapeutically effective amount of a SEGRAM. The present invention further relates to a method for preventing and/or treating an enhanced $T_h1$, $T_h2$ and/or $T_h17$ activity in a subject in need thereof, comprising administering to the subject a therapeutically effective amount of the composition, pharmaceutical composition, medicament or cosmeceutical composition according to the invention.

The present invention further relates to a method for preventing and/or treating an increased level of secreted cytokines and antibodies in a subject in need thereof, comprising administering to the subject a therapeutically effective amount of a SEGRAM. The present invention further relates to a method for preventing and/or treating an increased level of secreted cytokines and antibodies in a subject in need thereof, comprising administering to the subject a therapeutically effective amount of the composition, pharmaceutical composition, medicament or cosmeceutical composition according to the invention.

In one embodiment, the SEGRAM is a compound of Formula 1 or a derivative thereof, or a pharmaceutically acceptable enantiomer, deuterated form, salt, solvate and/or prodrug thereof.

In one embodiment, the SEGRAM does not induce or does not substantially induce neither direct transactivation, nor direct transrepression functions of the glucocorticoid receptor (GR). In one embodiment, the SEGRAM induces the indirect tethered transrepression functions of the glucocorticoid receptor (GR).

In one embodiment, the SEGRAM does not induce or does not substantially induce steroidal anti-inflammatory drugs (SAIDs)-associated side effects upon administration to a subject in need thereof. In one embodiment, a therapeutically effective amount of the composition, pharmaceutical composition, medicament or cosmeceutical composition according to the invention does not induce or does not substantially induce steroidal anti-inflammatory drugs (SAIDs)-associated side effects upon administration to a subject in need thereof.

In one embodiment, the methods of the present invention are for preventing and/or treating a $T_h1$-, $T_h2$- and/or $T_h17$-related inflammatory disorder. In one embodiment, the methods of the present invention are for preventing and/or treating an inflammatory disorder selected from the group comprising or consisting of atopic dermatitis, contact dermatitis, allergic asthma, allergic sinusitis, allergic conjunctivitis, allergic rhinitis, rhinoconjunctivitis, giant-cell arteritis (Horton disease), hay fever, solar dermatitis, eczema, urticaria, angioedema, erythema nodosum, erythema multiforme, cutaneous necrotizing venulitis, insect bite skin inflammation, anaphylaxis, psoriasis, rheumatoid arthritis, inflammatory bowel disease (IBD) (including, but not limited to, Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease. In one embodiment, the methods of the present invention are for preventing and/or treating an inflammatory disorder selected from the group comprising or consisting of atopic dermatitis, contact dermatitis, allergic asthma, psoriasis, allergic conjunctivitis, rheumatoid arthritis and inflammatory bowel disease (IBD) (including, but not limited to, Crohn's disease, ulcerative colitis and colitis). In one embodiment, the methods of the present invention are for preventing and/or treating atopic dermatitis. In one embodiment, the methods of the present invention are for preventing and/or treating contact dermatitis. In one embodiment, the methods of the present invention are for preventing and/or treating allergic asthma. In one embodiment, the methods of the present invention are for preventing and/or treating psoriasis. In one embodiment, the methods of the present invention are for preventing and/or treating rheumatoid arthritis. In one embodiment, the methods of the present invention are for preventing and/or treating ulcerative colitis. In one embodiment, the uses of the present invention are for preventing and/or treating allergic conjunctivitis. In one embodiment, the methods of the present invention are for preventing and/or treating postmenopausal-induced metabolic syndrome and steatosis.

In one embodiment, the secreted cytokines and antibodies are selected from the group comprising or consisting of IL-1β, IL-2, IL-3, IL-4, IL-5, IL-6, IL-10, IL-12, IL-13, IL-17a, IL-17c, IL-17f, IL-18, IL-21, IL-22, IL-23, IL-33, TSLP, TGFβ, CCL4, TNFα, COX2, MMP13, IgE, IgG1 and IgG2a.

Bare Uses

The present invention further relates to the use of a therapeutically effective amount of a SElective GR Agonistic Modulator (SEGRAM) for preventing and/or treating an inflammatory disorder in a subject in need thereof. The present invention further relates to the use of a therapeutically effective amount of the composition, pharmaceutical composition, medicament or cosmeceutical composition according to the invention for preventing and/or treating an inflammatory disorder in a subject in need thereof.

The present invention further relates to the use of a therapeutically effective amount of a SEGRAM for preventing and/or treating an enhanced $T_h1$, $T_h2$ and/or $T_h17$ activity in a subject in need thereof. The present invention further relates to the use of a therapeutically effective amount of the composition, pharmaceutical composition, medicament or cosmeceutical composition according to the invention for preventing and/or treating an enhanced $T_h1$, $T_h2$ and/or $T_h17$ activity in a subject in need thereof.

The present invention further relates to the use of a therapeutically effective amount of a SEGRAM for preventing and/or treating an increased level of secreted cytokines and antibodies in a subject in need thereof. The present invention further relates to the use of a therapeutically effective amount of the composition, pharmaceutical composition, medicament or cosmeceutical composition according to the invention for preventing and/or treating an increased level of secreted cytokines and antibodies in a subject in need thereof.

In one embodiment, the SEGRAM is a compound of Formula 1 or a derivative thereof, or a pharmaceutically acceptable enantiomer, deuterated form, salt, solvate and/or prodrug thereof.

In one embodiment, the SEGRAM does not induce or does not substantially induce neither direct transactivation, nor direct transrepression functions of the glucocorticoid receptor (GR). In one embodiment, the SEGRAM induces the indirect tethered transrepression functions of the glucocorticoid receptor (GR).

In one embodiment, the SEGRAM does not induce or does not substantially induce steroidal anti-inflammatory drugs (SAIDs)-associated side effects upon administration to a subject in need thereof. In one embodiment, a therapeutically effective amount of the composition, pharmaceutical composition, medicament or cosmeceutical composition according to the invention does not induce or does not substantially induce steroidal anti-inflammatory drugs (SAIDs)-associated side effects upon administration to a subject in need thereof.

In one embodiment, the uses of the present invention are for preventing and/or treating a $T_h1$-, $T_h2$- and/or $T_h17$-related inflammatory disorder. In one embodiment, the uses of the present invention are for preventing and/or treating an inflammatory disorder selected from the group comprising or consisting of atopic dermatitis, contact dermatitis, allergic asthma, allergic sinusitis, allergic conjunctivitis, allergic rhinitis, rhinoconjunctivitis, giant-cell arteritis (Horton disease), hay fever, solar dermatitis, eczema, urticaria, angioedema, erythema nodosum, erythema multiforme, cutaneous necrotizing venulitis, insect bite skin inflammation, anaphylaxis, psoriasis, rheumatoid arthritis, inflammatory bowel disease (IBD) (including, but not limited to, Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease. In one embodiment, the uses of the present invention are for preventing and/or treating an inflammatory disorder selected from the group comprising or consisting of atopic dermatitis, contact dermatitis, allergic asthma, psoriasis, allergic conjunctivitis, rheumatoid arthritis and inflammatory bowel disease (IBD) (including, but not limited to, Crohn's disease, ulcerative colitis and colitis). In one embodiment, the uses of the present invention are for preventing and/or treating atopic dermatitis. In one embodiment, the uses of the present invention are for preventing and/or treating contact dermatitis. In one embodiment, the uses of the present invention are for preventing and/or treating allergic asthma. In one embodiment, the uses of the present invention are for preventing and/or treating psoriasis. In one embodiment, the uses of the present invention are for preventing and/or treating rheumatoid arthritis. In one embodiment, the uses of the present invention are for preventing and/or treating ulcerative colitis. In one embodiment, the uses of the present invention are for preventing and/or treating allergic conjunctivitis. In one embodiment, the uses of the present invention are for preventing and/or treating postmenopausal-induced metabolic syndrome and steatosis.

In one embodiment, the secreted cytokines and antibodies are selected from the group comprising or consisting of IL-1β, IL-2, IL-3, IL-4, IL-5, IL-6, IL-10, IL-12, IL-13, IL-17a, IL-17c, IL-17f, IL-18, IL-21, IL-22, IL-23, IL-33, TSLP, TGFβ, CCL4, TNFα, COX2, MMP13, IgE, IgG1 and IgG2a.

Purpose-Limited Product

The present invention further relates to a Selective GR Agonistic Modulator (SEGRAM) for use in preventing and/or treating an inflammatory disorder in a subject in need thereof. The present invention further relates to the composition, pharmaceutical composition, medicament or cosmeceutical composition according to the invention for use in preventing and/or treating an inflammatory disorder in a subject in need thereof.

The present invention further relates to a SEGRAM for use in preventing and/or treating an enhanced $T_h1$, $T_h2$ and/or $T_h17$ activity in a subject in need thereof. The present invention further relates to the composition, pharmaceutical composition, medicament or cosmeceutical composition according to the invention for use in preventing and/or treating an enhanced $T_h1$, $T_h2$ and/or $T_h17$ activity in a subject in need thereof.

The present invention further relates to a SEGRAM for use in preventing and/or treating an increased level of secreted cytokines and antibodies in a subject in need thereof. The present invention further relates to the composition, pharmaceutical composition, medicament or cosmeceutical composition according to the invention for use in preventing and/or treating an increased level of secreted cytokines and antibodies in a subject in need thereof.

In one embodiment, the SEGRAM is a compound of Formula 1 or a derivative thereof, or a pharmaceutically acceptable enantiomer, deuterated form, salt, solvate and/or prodrug thereof.

In one embodiment, the SEGRAM does not induce or does not substantially induce neither direct transactivation, nor direct transrepression functions of the glucocorticoid receptor (GR). In one embodiment, the SEGRAM induces the indirect tethered transrepression functions of the glucocorticoid receptor (GR).

In one embodiment, the SEGRAM does not induce or does not substantially induce steroidal anti-inflammatory drugs (SAIDs)-associated side effects upon administration to a subject in need thereof. In one embodiment, a therapeutically effective amount of the composition, pharmaceutical composition, medicament or cosmeceutical composition according to the invention does not induce or does not substantially induce steroidal anti-inflammatory drugs (SAIDs)-associated side effects upon administration to a subject in need thereof.

In one embodiment, the SEGRAM, composition, pharmaceutical composition, medicament or cosmeceutical composition according to the invention are for use in preventing and/or treating a $T_h1$-, $T_h2$- and/or $T_h17$-related inflammatory disorder. In one embodiment, the SEGRAM, composition, pharmaceutical composition, medicament or cosmeceutical composition according to the invention are for use in preventing and/or treating an inflammatory disorder selected from the group comprising or consisting of atopic dermatitis, contact dermatitis, allergic asthma, allergic sinusitis, allergic conjunctivitis, allergic rhinitis, rhinoconjunctivitis, giant-cell arteritis (Horton disease), hay fever, solar dermatitis, eczema, urticaria, angioedema, erythema nodosum, erythema multiforme, cutaneous necrotizing venulitis, insect bite skin inflammation, anaphylaxis, psoriasis, rheumatoid arthritis, inflammatory bowel disease (IBD) (including, but not limited to, Crohn's disease, ulcerative colitis and colitis), periodontitis, chronic inflammatory diseases, lupus erythematosus, dermatomyositis, vasculitis, Sjogren's syndrome, scleroderma, multiple sclerosis, vitiligo, lichen planus, type 2 diabetes, coronary heart disease, hyperlipidemia, postmenopausal-induced metabolic syndrome and steatosis, and graft-versus-host disease. In one embodiment, the SEGRAM, composition, pharmaceutical composition, medicament or cosmeceutical composition according to the invention are for use in preventing and/or treating an inflammatory disorder selected from the group comprising or consisting of atopic dermatitis, contact dermatitis, allergic asthma, psoriasis, allergic conjunctivitis, rheumatoid arthritis and inflammatory bowel disease (IBD) (including, but not limited to, Crohn's disease, ulcerative colitis and colitis). In one embodiment, the SEGRAM, composition, pharmaceutical composition, medicament or cosmeceutical composition according to the invention are for use in preventing and/or treating atopic dermatitis. In one embodiment, the SEGRAM, composition, pharmaceutical composition, medicament or cosmeceutical composition according to the invention are for use in preventing and/or treating contact dermatitis. In one embodiment, the SEGRAM, composition, pharmaceutical composition, medicament or cosmeceutical composition according to the invention are for use in preventing and/or treating allergic asthma. In one embodiment, the SEGRAM, composition, pharmaceutical composition, medicament or cosmeceutical composition according to the invention are for use in preventing and/or treating psoriasis. In one embodiment, the SEGRAM, composition, pharmaceutical composition, medicament or cosmeceutical composition according to the invention are for use in preventing and/or treating rheumatoid arthritis. In one embodiment, the SEGRAM, composition, pharmaceutical composition, medicament or cosmeceutical composition according to the invention are for use in preventing and/or treating ulcerative colitis. In one embodiment, the uses of the present invention are for preventing and/or treating allergic conjunctivitis. In one embodiment, the SEGRAM, composition, pharmaceutical composition, medicament or cosmeceutical composition according to the invention are for use in preventing and/or treating postmenopausal-induced metabolic syndrome and steatosis.

In one embodiment, the secreted cytokines and antibodies are selected from the group comprising or consisting of IL-10, IL-2, IL-3, IL-4, IL-5, IL-6, IL-10, IL-12, IL-13, IL-17a, IL-17c, IL-17f, IL-18, IL-21, IL-22, IL-23, IL-33, TSLP, TGFβ, CCL4, TNFα, COX2, MMP13, IgE, IgG1 and IgG2a.

EXAMPLES

The present invention is further illustrated by the following examples.

Example 1: Synthesis of CpdX and CpdX-D3 and Separation of their Enantiomers

"Racemic" CpdX Synthesis and Separation of its Enantiomers CpdX(eA) and CpdX(eB)

The racemic mixture of the so-called compound CpdX {(R/S)-5-[4-(5-fluoro-2-methoxyphenyl)-2-hydroxy-4- methyl-2-(trifluoromethyl)pentylamino]isobenzofuran-1 (3H)-one}, was synthesized as outlined in FIG. 2A to 99.5% purity, and its identity was confirmed by LCMS (MS+1=442.1), HPLC, HNMR and FNMR.

300 mg of a racemic mixture of CpdX were then run through a preparative supercritical fluid chromatography (SFC) AD column (250 mm*30 mm*5 µm; mobile phase: Neu-MeOH; B %: 20%-20%, 2.3 minutes).

The collected fractions corresponding to the first elution peak (CpdX Peak1, FIG. 2B) were then concentrated under reduced pressure at 30° C., lyophilized and further purified through a Phenomenex Synergi C18 column chromatography [150 mm*25 mm*10 µm; mobile phase: water (0.1% TFA)-ACN; B %: 50%-80%, 10 minutes]. The collected fractions were concentrated under reduced pressure at 30° C. and lyophilized as a white solid (97.77 mg), the identity of which was confirmed by LCMS (MS+1=442.1) and SFC (retention time (RT)=1.084 mins), and named as the "CpdX (eA)" enantiomer (97.6% purity) (Table 1).

The collected fractions corresponding to the second elution peak (CpdX Peak2, FIG. 2B) were similarly concentrated under reduced pressure at 30° C., lyophilized and further purified by Phenomenex Synergi C18 column chromatography [150 mm*25 mm*10 µm); mobile phase: water (0.1% TFA)-ACN; B %: 51%-81%, 12 minutes]. The collected fractions were concentrated under reduced pressure at 30° C. and lyophilized as a white solid (101.72 mg), the identity of which was confirmed by LCMS (MS+1=442.1) and SFC (RT=1.147 minutes), and named as the "CpdX (eB)" enantiomer with a 98% purity (Table 1).

Further analysis will determine which of the two enantiomers CpdX(eA) and CpdX(eB) corresponds to the R and S forms, respectively.

TABLE 1

| Peak | Retention time (minutes) | Height | Height % | USP width | Area | Area % |
|---|---|---|---|---|---|---|
| Peak1 | 1.084 | 340022 | 50.432 | 0.052 | 619587 | 49.528 |
| Peak2 | 1.147 | 334193 | 49.568 | 0.052 | 631403 | 50.472 |

"Racemic" CpdX-D3 Synthesis and Separation of its Enantiomers CpdX-D3(eA) and CpdX-D3(eB)

The racemic mixture of the so-called deuterated compound CpdX-D3, corresponding to the deuterated compound {(R/S)-5-{4-[2-(methoxy-D3)-5-fluorophenyl]-2-hydroxy-4-methyl-2-(trifluoromethyl)pentylamino}isobenzofuran-1(3H)-one}, was synthesized as in FIG. 2C with a 99.3% purity and a 98.83% deuterium content, and its identity was confirmed by LCMS (MS+1=445), HPLC, HNMR and FNMR.

84.4 mg of CpdX-D3 was then run through a preparative supercritical fluid chromatography (SFC) DAICEL CHIRALPAK AD-H column (250 mm*30 mm*5 µm; mobile phase: 0.1% NH$_3$H$_2$O-MEOH; B %: 20%-20%, 2.3 minutes).

The collected fractions corresponding to the first elution peak (CpdX-D3 Peak1) were concentrated under reduced pressure at 30° C. and lyophilized as a white solid (32.41 mg), the identity of which was confirmed by LCMS (MS+1=445) and SFC (RT=1.082 minutes), and named as the enantiomer "CpdX-D3(eA)" with a 98.7% purity.

The collected fractions corresponding to the second elution peak (CpdX-D3 Peak2) were concentrated under reduced pressure at 30° C. and lyophilized as a white solid (31.06 mg), the identity of which was confirmed by LCMS (MS+1=445) and SFC (RT=1.149 minutes), and named as the "CpdX-D3(eB)" enantiomer with a 99.1% purity (FIG. 2D).

Further analysis will determine which of the two enantiomers CpdX-D3(eA) and CpdX-D3(eB) corresponds to the R and S forms, respectively.

Figure 3:
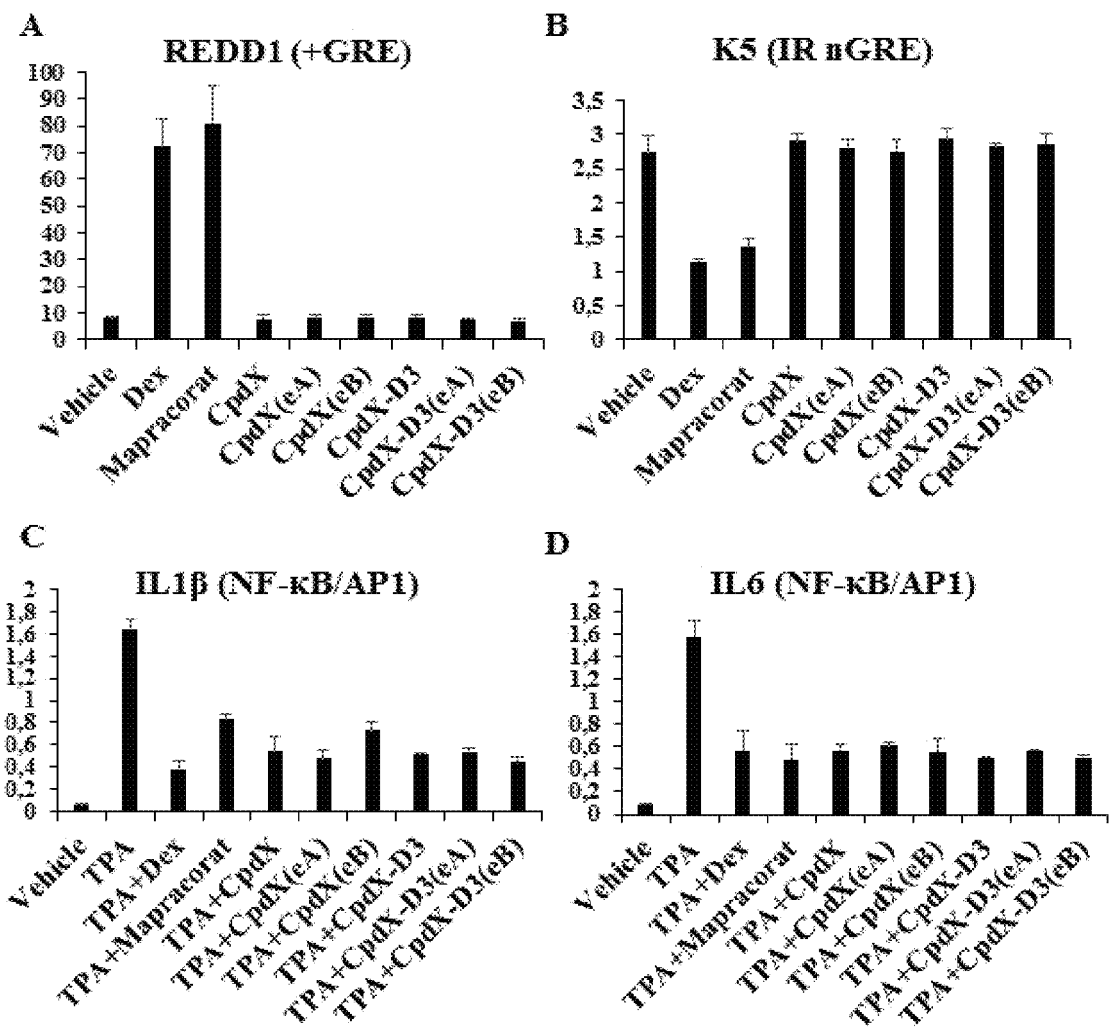
FIG. 3 is a set of four histograms showing the expression of RNA transcripts as indicated (relative to that of the HPRT housekeeping gene) measured by qRT-PCR analysis (A) from the GR-transactivated REDD1 gene which encodes a mTOR inhibitor; (B) from the GR directly-transrepressed keratin 5 (K5) gene; (C) from the GR indirectly-transrepressed interleukin-1β(IL-1β) gene; and (D) from the GR indirectly-transrepressed interleukin-6 (IL-6) gene. RNA transcripts were extracted from mouse ears after a topical 18-hour-treatment with (A and B) ethanol [Vehicle], 1 nmole/cm$^2$ of either dexamethasone [Dex], Mapracorat, (R/S)-5-[4-(5-fluoro-2-methoxyphenyl)-2-hydroxy-4- methyl-2-(trifluoromethyl)pentylamino]isobenzofuran-1 (3H)-one [CpdX], CpdX(eA), CpdX(eB), (R/S)-5-{4-[2-(methoxy-D3)-5-fluorophenyl]-2-hydroxy-4-methyl-2-(trifluoromethyl)pentylamino}isobenzofuran-1(3H)-one [CpdX-D3], CpdX-D3(eA) or CpdX-D3(eB); (C and D) as in (A and B), but with an additional 12-O-tetradecanoylphorbol-13-acetate [TPA] treatment (1 nmole/cm$^2$). Data are represented as mean±SEM of at least three independent experiments with at least three mice per treatment.

Example 2: Unlike Mapracorat/ZK245186, CpdX, CpdX(eA), CpdX(eB), CpdX-D3, CpdX-D3(eA) and CpdX-D3(eB) are Bona Fide Non-Steroidal SElective GR Agonistic Modulators (SEGRAMs) (see FIG. 3)

Material and Methods

Ears of Balb/C mice were treated overnight for 18 hours with 1 nmole/cm$^2$ of either:
Ethanol [vehicle],
Dexamethasone [Dex],
Mapracorat,
(R/S)-5-[4-(5-fluoro-2-methoxyphenyl)-2-hydroxy-4-methyl-2-(trifluoromethyl)pentylamino]isobenzofuran-1 (3H)-one [CpdX],
5-[4-(5-fluoro-2-methoxyphenyl)-2-hydroxy-4-methyl-2-(trifluoromethyl)-pentylamino]isobenzofuran-1(3H)-one enantiomer A [CpdX(eA)],
5-[4-(5-fluoro-2-methoxyphenyl)-2-hydroxy-4-methyl-2-(trifluoromethyl)-pentylamino]isobenzofuran-1(3H)-one enantiomer B [CpdX(eB)],
(R/S)-5-{4-[2-(methoxy-D3)-5-fluorophenyl]-2-hydroxy-4-methyl-2-(trifluoromethyl)pentylamino}isobenzofuran-1 (3H)-one [CpdX-D3],
5-{4-[2-(methoxy-D3)-5-fluorophenyl]-2-hydroxy-4-methyl-2-(trifluoromethyl)pentylamino}isobenzofuran-1 (3H)-one enantiomer A (CpdX-D3(eA)], or
5-{4-[2-(methoxy-D3)-5-fluorophenyl]-2-hydroxy-4-methyl-2-(trifluoromethyl)pentylamino}isobenzofuran-1 (3H)-one enantiomer B [CpdX-D3(eB)].

RNA transcripts were then extracted from mouse ears and the transcripts of 4 genes were analyzed by q-RT-PCR:
(i) the directly GR-transactivated gene of the mTOR inhibitor REDD1,
(ii) the GR-directly transrepressed gene of keratin 5 (K5) and
(iii) the GR-indirectly "tethered" transrepressed genes of interleukin-1β (IL-1β) and interleukin-6 (IL-6), both being activated in presence of 12-O-tetradecanoylphorbol-13-acetate (TPA).

Results

Figure 1:
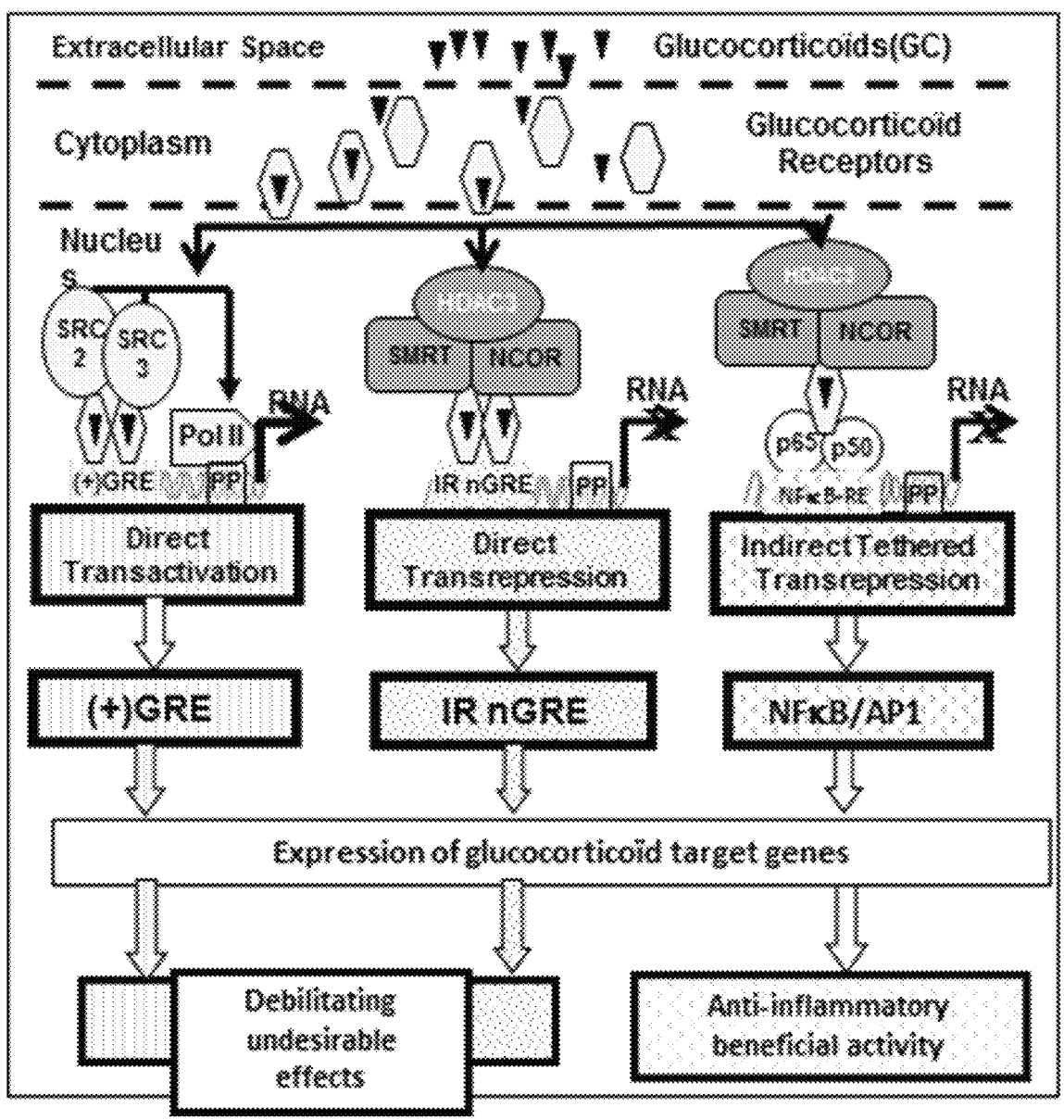
FIG. 1 is a scheme showing the three transcriptional regulatory functions of the glucocorticoid receptor (GR) upon binding of a glucocorticoid (GC): on the left, the direct transactivation is the consequence of the binding of GC-associated GR directly to a cis-acting positive GRE ((+) GRE), thereby activating the expression of target genes. In the middle, the direct transrepression is the consequence of the binding of GC-associated GR directly to a cis-acting negative GRE (IR nGRE) which mediates the direct repression of target genes. On the right, the indirect tethered transrepression arises from the physical interaction of GC-bound GRs with the proinflammatory transcription factors AP-1 and/or NF-κB, thereby antagonizing their activity.

Upon treatment with Dex or Mapracorat, in vivo transcriptional analyses have shown that Mapracorat, just as Dex, induces all three GR functions (direct transactivation, direct transrepression and indirect tethered transrepression, summarized in FIG. 1), with a similar transactivation of the REDD1 gene (FIG. 3A), a similar direct transrepression of the K5 gene (FIG. 3B), and a similar indirect transrepression of the IL-1β(FIG. 3C) and IL-6 (FIG. 3D) genes.

On the contrary, GR selectively exhibits an indirect tethered transrepression activity upon in vivo administration of CpdX, with unchanged relative RNA expression levels for the REDD1 and K5 genes, as compared to control (Vehicle). Similar results were also obtained upon administration of either CpdX(eA) or CpdX(eB), or of their deuterated counterparts CpdX-D3, CpdX-D3(eA) and CpdX-D3(eB).

Conclusion

Mapracorat is not a non-steroidal SElective GR Agonistic Modulator (SEGRAM), indicating that Mapracorat can exhibit—even if it could be to a lesser extent—similar side effects as those currently encountered upon a Dex treatment.

In marked contrast, CpdX, as well as its two enantiomers CpdX(eA) and CpdX(eB), selectively exhibit the indirect tethered transrepression activity of GR, as expected for bona fide SEGRAMs. Most interestingly, the deuterated CpdX (CpdX-D3) and its two enantiomers (CpdX-D3(eA) and CpdX-D3(eB)] exhibit the same selectivity and anti-inflammatory properties as their CpdX counterparts.

Example 3: CpdX and CpdX-D3 are as Efficient as Dexamethasone (Dex) at Decreasing a TPA-Induced Irritant Contact Dermatitis-Like $T_h1/T_h2/T_h17$ Inflammation (See FIG. 4)

Material and Methods

Balb/C mouse ears were topically treated with TPA to induce an "irritant contact dermatitis-like inflammation".

Mice were treated for 4 days with TPA, then for 5 extra days (until D9) with either vehicle, TPA alone, TPA and Dex, TPA and CpdX or TPA and CpdX-D3.

At D10, RNA transcripts were extracted from mouse ear skin samples and the transcripts of CCL4, COX2, MMP13, IL-1β, IL-6, TNF-α, TSLP, IL-22 and IL-23 were analyzed by q-RT-PCR. Ear skin was harvested, and histological (with H&E staining) and immunohistochemical (with anti-TSLP antibodies) analyses were carried out.

Results

The TPA-induced skin inflammation was significantly decreased by treatment with either Dex, CpdX or CpdX-D3.

Transcript analyses using ear extracts from these mice indicated that CpdX and CpdX-D3 repressed, as efficiently as Dex, the TPA-induced transcription of pro-inflammatory genes (FIG. 4).

Histological analysis of mouse ear skin showed that a TPA-induced ear skin inflammation was significantly decreased by treatment with either Dex, CpdX or CpdX-D3, as compared to the control (data not shown).

Immunochemistry analysis using a TSLP-specific antibody showed that the expression of TSLP in TPA-treated mouse epidermis was similarly strongly decreased by either a Dex, a CpdX or a CpdX-D3 treatment (data not shown).

Conclusion

Taken altogether, these results demonstrate that CpdX and CpdX-D3 repress induced-skin inflammations as efficiently as Dex, indicating that both of them can be used in the treatment of skin inflammations, notably in the treatment of $T_h1/T_h2/T_h17$-related inflammatory disorders, such as contact dermatitis.

Example 4: The Topical Administration of Either Dex, CpdX or CpdX-D3, in a Cream Formulation or in Ethanol (EtOH), Results in a Similar Anti-Inflammatory Activity (see FIGS. 5 and 6)

Material and Methods

Balb/C mouse ears were first topically treated with TPA for 3 days, which were followed by a three-day co-treatment without or with either Dex, CpdX or CpdX-D3 in ethanol (1 nmole/cm$^2$) or in a cream (0.05% w/w) composed of vaseline, liquid paraffin, Emulgade® 1000 NI (BASF), propyl gallate, sodium edetate, sorbic acid and purified water.

RNA transcripts were extracted from mouse ear skin samples and the transcripts of IL-1β, IL-6, COX2 and TNF-α were analyzed by q-RT-PCR. Ear skin was harvested and histological (with H&E staining) analyses were carried out.

Results

Transcript analyses of ear extracts revealed a similar repression of the pro-inflammatory genes by Dex, CpdX or CpdX-D3 administered either in ethanol or in a cream formulation (FIG. 5). Histological analysis of mouse ear skin confirmed similar anti-inflammatory effects (FIG. 6).

Conclusion

CpdX, as well as CpdX-D3, administered either in ethanol or in a cream formulation, have the same anti-inflammatory efficiency in the treatment of a skin inflammation.

Example 5: CpdX, CpdX(eA), CpdX(eB), CpdX-D3, CpdX-D3(eA) and CpdX-D3(eB) are as Efficient as Dexamethasone (Dex) at Decreasing a Calcipotriol (MC 903)-Induced Atopic Dermatitis-Like $T_h2$ Inflammation (See FIGS. 7 and 8)

Material and Methods

To investigate the CpdX anti-inflammatory activity in vivo, Balb/C mouse ears were topically treated with calcipotriol (MC 903, a vitamin D3 analogue), in order to induce an atopic dermatitis (AD)-like inflammation (Li et al., 2006. Proc Natl Acad Sci USA. 103(31):11736-41).

Mice were treated for 14 days with MC 903, and then for 8 extra days (until D22) with either MC 903 alone (control), MC 903 and Dex, MC 903 and CpdX, MC 903 and CpdX(eA), MC 903 and CpdX(eB), MC 903 and CpdX-D3, MC 903 and CpdX-D3(eA) and MC 903 and CpdX-D3(eB).

At D23, RNA transcripts were extracted from mouse ear skin samples and the transcripts of 7 cytokines (MMP13, COX2, IL-1β, IL-6, IL-10, IL-13 and TSLP) were analyzed by q-RT-PCR. Ear skin was harvested and histological (with H&E staining) and immunohistochemical (with anti-TSLP antibodies) analyses were carried out.

Results

The MC 903-induced skin inflammation was significantly decreased by treatment with either Dex, CpdX or CpdX-D3.

RNA transcript analyses of ear extracts from these mice indicated that CpdX and CpdX-D3 repressed, as efficiently as Dex, the MC 903-induced transcription of a variety of pro-inflammatory genes (MMP13, COX2, IL-1β, IL-6, IL-10, IL-13 and TSLP), including those of a $T_h2$ inflammation (IL-10, IL-13 and TSLP) (FIG. 7).

Histological analysis of mouse ear skin showed that a MC 903-induced ear skin inflammation was decreased by treatment with either Dex, CpdX or CpdX-D3, as compared to the control (FIG. 8).

Immunohistochemistry analysis using a TSLP-specific antibody showed that the expression of the TSLP lymphokine in MC 903-treated mouse epidermis was similarly strongly decreased by either Dex, CpdX or CpdX-D3 (data not shown).

Similar results were also observed for a treatment with either CpdX(eA), CpdX(eB), CpdX-D3(eA) or CpdX-D3 (eB) (FIGS. 7 and 8).

Conclusion

Taken altogether, these results demonstrate that a topical administration of CpdX, its deuterated form CpdX-D3 or any of their enantiomers [CpdX(eA), CpdX(eB), CpdX-D3 (eA) and CpdX-D3(eB)] reduce as efficiently as Dex a skin inflammation, indicating that all of them are useful in the treatment of skin inflammations, notably in the treatment of $T_h2$-related inflammatory disorders, such as atopic dermatitis.

Example 6: CpdX, CpdX(eA), CpdX-D3 and CpdX-D3(eA), but not CpdX(eB) Nor CpdX-D3 (eB), are as Efficient as Dexamethasone (Dex) at Decreasing an Asthma-Like Lung Allergic $T_h2$ Inflammation (See FIGS. 9 to 13)

Material and Methods

Glucocorticoids have been (Pearlman et al., 1997. *Ann Allergy Asthma Immunol.* 78(4):356-62), and are still, widely used in asthma therapy. In order to investigate the possible CpdX anti-inflammatory activity in vivo, mice were sensitized and challenged with either ovalbumin (OVA) or house dust mite (HDM) to induce an asthma-like allergic lung inflammation.

Ovalbumin Sensitization and Challenge

Mice were intraperitoneally sensitized with either 50 μg OVA together with alum or with alum alone on D0, D7 and D14. Mice were then subdivided into three groups, and on D19, D20 and D21, they were intranasally (i.n.) challenged with 10 μg OVA. The first and the second group received intranasally 0.5 mg/kg of body weight of Dex or CpdX respectively, while the third group served as a control.

On D22, the lung allergic inflammation was assessed for each mouse by examination of the bronchoalveolar lavage fluid (BAL). The total BAL cells, eosinophils, neutrophils, macrophages and lymphocytes were counted. RNA transcripts were extracted from lung samples and RNA transcripts of IL-1β, IL-6, IL-4, IL-5, IL-10, IL-13, Eotaxin, CCL4 and TNFα were analyzed by q-RT-PCR. Histological (with H&E staining) and immunohistochemical (with eosinophil-specific and neutrophil-specific antibodies) analyses of lung tissues were also carried out.

House Dust Mite (HDM) Sensitization and Challenge

Mice were intranasally sensitized with 1 μg HDM from D0 to D4, and further intranasally sensitized with 10 μg HDM on D14 and D21. Mice were then subdivided into eight groups, and on D29, D30 and D31, each mouse was again intranasally challenged with 1 HDM. The first seven groups received respectively 0.5 mg/kg of body weight of Dex, CpdX, CpdX(eA), CpdX(eB), CpdX-D3, CpdX-D3(eA) or CpdX-D3(eB), while the eighth group served as a control.

On D32, the airway responsiveness was invasively determined using a computer-controlled small animal ventilator (FlexVent® system, SCIREQ Technologies). Mice were anesthetized with xylazine (15 mg/kg, i.p.), followed 15 minutes later by an i.p. injection of pentobarbital sodium (54 mg/kg). An 18-gauge metal needle was then inserted into the trachea, each mouse was connected to the FlexVent® ventilator and quasi-sinusoidally ventilated with a tidal volume of 10 mL/kg at a frequency of 150 breaths/minute and a positive end-expiratory pressure of 2 cm $H_2O$, in order to achieve a mean lung volume close to spontaneous breathing. After baseline measurement, mice were challenged for 10 seconds with a saline aerosol and, at 4.5-minute intervals, with 50 mg/mL methacholine. Airway resistance and elastance were expressed as $cmH_2O.s/mL$ and $cmH_2O/mL$ respectively.

The lung allergic inflammation was assessed by examination of the bronchoalveolar lavage (BAL) fluid from each of these HDM-challenged mice. The total BAL cells, eosinophils, neutrophils, macrophages and lymphocytes were counted. RNA transcripts were extracted from lung samples. RNA transcripts of IL-1β, IL-6, IL-4, IL-5, IL-13, Eotaxin, CCL4, IL-10 and TNFα were analyzed by q-RT-PCR. Lung tissues were harvested and histological (with H&E staining) and immunohistochemical analyses were also carried out (with eosinophil-specific and neutrophil-specific antibodies).

Results

Ovalbumin Sensitization and Challenge

Upon treatment with either Dex or CpdX, the total number of BAL cells, eosinophils, neutrophils and lymphocytes were all significantly decreased as compared to the control group. The number of macrophages was unchanged (FIG. 9A).

Consistent with these results, transcriptional analyses of lung samples showed that the expressions of IL-1β, IL-6 and of the $T_h2$ pro-inflammatory genes IL-4, IL-5, IL-10 and IL-13, as well as of those of the eosinophil chemotactic chemokine Eotaxin, CCL4 and TNFα, were significantly and similarly decreased upon Dex or CpdX treatment (FIG. 9B).

Histological analyses of lung paraffin sections demonstrated that the peribronchiolar (B) and perivascular (V) inflammatory cell infiltration was strongly decreased by either Dex or CpdX treatment (FIG. 10).

Immunohistochemistry staining using eosinophil-specific and neutrophil-specific antibodies confirmed that both eosinophils and neutrophils were similarly decreased by either a Dex or a CpdX treatment (data not shown).

House Dust Mite (HDM) Sensitization and Challenge

Upon treatment with either Dex, CpdX or CpdX-D3, the total number of BAL cells, eosinophils and lymphocytes were significantly decreased as compared to the control group. No significant change was observed in the number of neutrophils and macrophages (FIGS. 11A and B).

RNA transcriptional analyses of lung samples showed that the expressions of IL-1β, IL-6 and of $T_h2$ pro-inflammatory genes (IL-4, IL-5, IL-13), as well as those of the eosinophil chemotactic chemokine Eotaxin and CCL4, were significantly and similarly decreased by Dex, CpdX or CpdX-D3 (FIGS. 11C and D), whereas those of IL-10 and TNFα were not affected (data not shown).

Histological analyses of lung paraffin sections demonstrated that the peribronchiolar and perivascular inflammatory cell infiltration was strongly decreased by either Dex, CpdX or CpdX-D3 treatment (FIG. 12).

Immunohistochemistry staining using eosinophil-specific antibodies confirmed that eosinophils were decreased by either Dex, CpdX or CpdX-D3 treatment (data not shown). However, no significant change was observed using a neutrophil-specific antibody (data not shown).

Pulmonary functional tests (responses to methacholine analyzed by invasive measurements of airway resistance and elastance) demonstrated that Dex, CpdX or CpdX-D3 administration similarly reduced HDM-induced airway hyperresponsiveness (AHR) (FIG. 13).

Surprisingly, a treatment with CpdX(eA) or CpdX-D3 (eA), but not with CpdX(eB) nor CpdX-D3(eB), efficiently decreased the number of total BAL cells, eosinophils and lymphocytes (FIGS. 11A and B), as well as the expression of pro-inflammatory genes (FIGS. 11C and D). Histological analyses of lung paraffin sections revealed that the peribronchiolar and perivascular inflammatory cell infiltration was decreased by a CpdX(eA) or a CpdX-D3(eA) treatment, but not by a CpdX(eB) nor a CpdX-D3(eB) treatment (FIG. 12). Accordingly, pulmonary functional tests showed that administration of CpdX(eA), but not CpdX(eB), reduced the HDM-induced airway hyperresponsiveness (AHR) (FIG. 13).

Conclusion

Taken altogether, these results demonstrate that CpdX and CpdX-D3 repressed, as efficiently as Dex, allergen-induced lung inflammations, indicating their potential usefulness for the treatment of the $T_h2$-related inflammatory disorders, such as asthma. Interestingly, CpdX(eA) and CpdX-D3(eA), but neither CpdX(eB) nor CpdX-D3(eB), did efficiently repress HDM-induced lung inflammation, indicating that only CpdX(eA) or CpdX-D3(eA) is the active enantiomer in the treatment of asthma.

Example 7: An Aldara-Induced Psoriasis-Like $T_h17$ Inflammation is Reduced by a Topical Treatment with Either Dexamethasone (Dex), CpdX or CpdX-D3 (See FIGS. 14 and 15)

Material and Methods

Balb/C mouse ears were topically treated with Aldara® to induce a psoriasis-like skin inflammation (Vinter et al., 2015. Br J Dermatol. 172(2):345-53). Mice were treated for 9 days with Aldara®, including a co-topical treatment for the last 5 days with either ethanol (Vehicle), Dex, CpdX or CpdX-D3.

At D10, RNA transcripts were extracted from mouse ears and IL-17a, IL-17c, IL-17f and IL-22 transcripts were analyzed by q-RT-PCR. Ear skin samples were also harvested for histological analyses (with H&E staining).

Results

The Aldara®-induced psoriasis-like skin inflammation was significantly decreased by treatment with either Dex, CpdX or CpdX-D3. Interestingly, RNA transcript analyses of ear extracts indicated that the induced expression of the $T_h17$ cytokines IL-17a, IL-17c, IL-17f and IL-22; but not of IL-23, were similarly reduced by a Dex, a CpdX or a CpdX-D3 treatment (FIG. 14 and data not shown).

Histological analyses by H&E staining confirmed these results and showed that either Dex, CpdX or CpdX-D3 could reduce an Aldara®-induced psoriasis-like skin inflammation (FIG. 15).

Conclusion

These results demonstrate that in the mouse, CpdX or CpdX-D3 repressed, as efficiently as Dex, an Aldara-induced psoriasis-like skin inflammation, indicating that both CpdX and CpdX-D3 are as efficient as Dex in the treatment of this $T_h17$-related inflammatory skin disorder.

Example 8: CpdX, CpdX(eA), CpdX-D3 and CpdX-D3(eA), but not CpdX(eB), Nor CpdX-D3 (eB), are as Efficient as Dexamethasone (Dex) at Decreasing a Collagen-Induced Arthritis (CIA) $T_h17$ Inflammation (See FIGS. 16 to 18)

Material and Methods

Mice were treated with collagen to induce a $T_h17$ rheumatoid arthritis-like inflammation as described by Inglis et al. (2007. Arthritis Res Ther. 9(5):R113) and Geboes et al. (2009. Arthritis Rheum. 60(2):390-5).

Male mice (DBA-1 strain) were subcutaneously-injected with 100 µg collagen per mouse on D0. The hind paw thickness at the ankle level was regularly measured with a caliper. When the ankle thickness had reached around 4 mm (T0, i.e., 30 to 50 days after the collagen injection on D0), mice were daily intraperitoneally-injected for 10 days (T0 to T10) with either vehicle (NaCl 0.9%), Dex, CpdX, CpdX (eA), CpdX(eB), CpdX-D3, CpdX-D3(eA) or CpdX-D3 (eB) (1 mg/kg body weight diluted in NaCl 0.9%), and the hind paw thickness at the ankle level was daily measured with a caliper. Pictures of the hind paws were taken at days T0 and T10 (before and after the treatment with either Vehicle, Dex, CpdX, CpdX(eA), CpdX(eB), CpdX-D3, CpdX-D3(eA) or CpdX-D3(eB)), in order to assess the course of swelling.

RNA transcripts were extracted from whole hind paws of collagen-untreated and collagen-treated mice at T0 and T10. IL-1β, IL-6, IL-17a, IL-17f and TNFα transcripts were analyzed by q-RT-PCR.

Results

The hind paw thickness showed an increase upon collagen injection, whereas Dex, CpdX and CpdX-D3 treatments resulted within 10 days into a rapid decrease of this thickness (FIGS. 16 and 17A). A similar decrease of the hind paw thickness was observed in mice treated with CpdX(eA) or CpdX-D3(eA), while in marked contrast no such decrease was observed upon a CpdX(eB) or a CpdX-D3(eB) treatment (FIG. 17B and data not shown).

Most notably, the RNA transcripts of the pro-inflammatory genes which are expressed in the hind paws of mice which developed a CIA were similarly repressed by either a dexamethasone, a CpdX, a CpdX(eA), a CpdX-D3 or a CpdX-D3(eA) treatment, but not by a CpdX(eB), nor a CpdX-D3(eB) treatment (FIG. 18).

Conclusion

These results demonstrate that both CpdX and CpdX-D3, as well as their enantiomers CpdX(eA), CpdX-D3(eA), but not their CpdX(eB) nor CpdX-D3(eB) enantiomers, are as efficient as Dex at decreasing a rheumatoid arthritis-like $T_h17$ inflammatory.

Example 9: CpdX, CpdX(eA), CpdX(eB), CpdX-D3, CpdX-D3(eA) and CpdX-D3(eB) are as Efficient as Dexamethasone (Dex) at Curing a Dextran Sodium Sulfate (DSS)-Induced $T_h17$ Ulcerative Colitis (See FIGS. 19 and 20)

Material and Methods

To investigate the anti-inflammatory activity of CpdX and CpdX-D3 on a $T_h17$ ulcerative colitis, Balb/C mice were treated with 3% DSS in drinking water for 13 days, with or without an intraperitoneal administration of either Dex, CpdX, CpdX(eA), CpdX(eB), CpdX-D3, CpdX-D3(eA) or CpdX-D3(eB) (1 mg/kg of body weight) on D11, D12 and D13.

At D14, RNA transcripts were extracted from mouse colons. IL-1β, IL-6, IL-17a, IL-17f, TSLP and MMP13 transcripts were analyzed by q-RT-PCR. Colon samples were also harvested for histological analyses (with H&E staining).

Results

Histological analyses (H&E stained paraffin sections) (FIG. 19 and data not shown) showed dramatic damages in DSS-treated mouse colon as compared to control mice (no DSS treatment): the regular colonic villus/crypt structure was highly disorganized or absent in DSS-treated mice. In addition, ulcerations (arrow head), as well as cell infiltrations into the colonic mucosal (solid arrows) and submucosal (dotted arrows) layers were also observed. Most notably, in mice treated for 3 days with either Dex, CpdX, CpdX-D3 or their two enantiomers CpdX(eA), CpdX(eB), CpdX-D3(eA) and CpdX-D3(eB), the colonic villus/crypt structure was almost reestablished and both the mucosal and the submucosal cell infiltration were significantly decreased.

Transcriptional analyses showed (FIG. 20) that the pro-inflammatory genes which were overexpressed in DSS-induced ulcerative colitis were similarly repressed by either Dex, CpdX, CpdX(eA), CpdX(eB), CpdX-D3, CpdX-D3 (eA) or CpdX-D3(eB).
Conclusion Taken altogether, our results demonstrate that CpdX, CpdX-D3 and their enantiomers CpdX(eA), CpdX(eB), CpdX-D3(eA) and CpdX-D3(eB) are as efficient as Dex for the treatment of a $T_h17$-related inflammatory disorder, such as ulcerative colitis.

Example 10: CpdX, CpdX(eA), CpdX(eB), CpdX-D3, CpdX-D3(eA) or CpdX-D3(eB) Alleviate as Efficiently as Dexamethasone (Dex) an Ovalbumin (OVA)-Induced Allergic Conjunctivitis (See FIG. 21)

Material and Methods

To investigate the anti-inflammatory effect of CpdX or CpdX-D3 on an allergic conjunctivitis, Balb/C mice were intraperitoneally sensitized with 50 µg OVA with alum on both days D1 and D8, and then challenged from D15 to D21 with 250 µg OVA in 5 µL of sterilized vehicle (0.9% NaCl), which were directly instilled onto the conjunctival sac. From D22 to D24, mice were divided into several groups, and received instillations with either OVA alone, OVA together with 0.1% of either Dex, CpdX, CpdX(eA), CpdX(eB), CpdX-D3, CpdX-D3(eA) or CpdX-D3(eB).

The clinical appearance of mouse eyes was evaluated 20 minutes after the last instillation on D24. Clinical signs (conjunctival hyperemia, lid edema and tearing) were scored to evaluate the occurrence and severity of conjunctivitis as described by Gimenes et al. (2015. *Experimental Eye Research* 134:24-32). Parameters were graded on a scale ranging from 0 to 3, (0=absence, 1=mild, 2=moderate, and 3=severe symptoms), each animal receiving a total clinical score ranging from 0 to 9. The data were expressed as mean±SEM with at least four mice per treatment.
Results 20 minutes after the last OVA challenge, eyes from all OVA-treated mice presented obvious clinical signs of allergic conjunctivitis as compared to control mice (Vehicle) (FIG. 21). These signs were considerably reduced by Dex treatment, as well as by either CpdX, CpdX(eA), CpdX(eB), CpdX-D3, CpdX-D3(eA) or CpdX-D3(eB) treatment (FIG. 21).
Conclusion These results demonstrate that CpdX, CpdX-D3 and their enantiomers CpdX(eA), CpdX(eB), CpdX-D3(eA) and CpdX-D3(eB) reduce, as efficiently as Dex, an ovalbumin (OVA)-induced allergic conjunctivitis.

Example 11: In Marked Contrast to Dexamethasone (Dex), a Topical Treatment with Either CpdX, CpdX(eA), CpdX(eB), CpdX-D3, CpdX-D3(eA) or CpdX-D3(eB) does not Induce a Skin Epidermis Atrophy (See FIGS. 22 to 24)

Material and Methods

Skin atrophy is a severe limitation to topical treatments with glucocorticoids (Schoepe et al., 2006. *Exp Dermatol.* 15(6):406-20).

To investigate whether, similarly to Dex, a topical administration of CpdX could result in a skin atrophy, Balb/C mice were shaved on the dorsal skin. Ethanol (vehicle), Dex, CpdX or either one of its two enantiomers CpdX(eA) or CpdX(eB), as well as the deuterated form CpdX-D3 or either one of its two enantiomers CpdX-D3(eA) or CpdX-D3(eB), were topically applied onto the dorsal skin for 8 days.

Upon completion of the treatments, RNA transcripts were extracted from dorsal skin samples and the transcripts of Kindlin-1 and REDD1 genes were analyzed by q-RT-PCR. Histological and morphometric analyses of the dorsal skin were also performed.
Results It has been reported that a loss of the Kindlin-1 protein results in an epidermal skin atrophy (Ussar et al., 2008. *PLoS Genet.* 4(12):e1000289), while, in marked contrast, the loss of the Redd1 protein prevents a GC-induced skin atrophy (Britto et al., 2014. *Am J Physiol Endocrinol Metab.* 307(11):E983-93; Baida et al., 2015. *EMBO Mol Med.* 7(1):42-58).

Most interestingly, transcriptional analyses from dorsal skin samples clearly indicated that the transcription of the Kindlin-1 gene (which contains a nGRE) is strongly decreased by a Dex topical treatment, but not by either of a CpdX, CpdX(eA), CpdX(eB), CpdX-D3, CpdX-D3(eA) or CpdX-D3(eB) treatment (FIG. 22A). Conversely, the transcription of the REDD1 gene (which contains a +GRE) is significantly increased by a Dex, but not by a CpdX, a CpdX(eA), a CpdX(eB), a CpdX-D3, a CpdX-D3(eA) nor a CpdX-D3(eB) treatment (FIG. 22B).

Consistent with RNA transcripts analyses, morphometric analyses showed that the epidermal thickness decreases by 65% upon an eight-day Dex treatment. In contrast, the epidermal thickness is not significantly decreased by a CpdX, a CpdX(eA), a CpdX(eB), a CpdX-D3, a CpdX-D3 (eA) or a CpdX-D3(eB) treatment (FIG. 23). These data are fully consistent with the histological analysis demonstrating that an application of Dex, in marked contrast with that of CpdX or its deuterated form CpdX-D3 or any of their enantiomers, severely induces a skin atrophy (FIG. 24).
Conclusion Our results clearly demonstrate that, in marked contrast with a Dex topical treatment, a topical treatment with either CpdX, or its deuterated form CpdX-D3, or any of their enantiomers [CpdX(eA), CpdX(eB), CpdX-D3(eA) and CpdX-D3(eB)], does not result in an epidermal skin atrophy, indicating CpdX and CpdX-D3 can be safely used in skin treatments.

Example 12: A Three-Month Treatment with Either CpdX, CpdX(eA), CpdX(eB), CpdX-D3, CpdX-D3 (eA) or CpdX-D3(eB) does not affect the cortical nor the trabecular bone formation, in contrast to a Dexamethasone (Dex) treatment (see FIGS. 25 and 26)

Material and Methods

B6 male mice (8-week-old) were daily subjected for three months to either a subcutaneous injection of vehicle (NaCl 0.9%), Dex, CpdX, CpdX(eA), CpdX(eB), CpdX-D3, CpdX-D3(eA) or CpdX-D3(eB) (1 mg/kg body weight, diluted in NaCl 0.9%).

From each animal included in the experiments, one femur and the ipsilateral tibia were dissected and preserved in 70% ethanol for further bone microstructure analysis by micro-CT. The FX Quantum micro-CT scanner (Perkin Elmer) was used to perform measurements at the distal femur and midshaft tibia. All scans were performed with an isotropic voxel size of 10 µm, 160 µA tube current and 90 kV tube voltage.

Morphological 3D measurements were performed using the CTAn software (Bruker). Cortical bone parameters, which were measured in the tibia midshaft, included measures of the bone volume fraction as compared to the total volume, cortical thickness, total area, bone area and marrow area. The region of interest was selected from below the distal tibial crest and continued for 20 slices toward the proximal end of the tibia. Trabecular bone parameters were measured in the distal metaphysis of the femurs and included bone volume fraction, trabecular thickness, trabecular number and trabecular spacing. The region of interest was selected from below the distal growth plate where the epiphyseal cap structure completely disappeared and continued for 100 slices toward the proximal end of the femur.

The statistical significance as compared to vehicle treatment was calculated through one-way ANOVA test followed by Dunn's multiple comparison test, *p<0.05; p<0.01; *p<0.001; ****p<0,0001.

Results

Osteoporosis is a common undesirable side effect of a long-term glucocorticoid clinical treatment (Canalis, 2003. Curr Opin Rheumatol. 15(4):454-7). As expected, after a three-month Dex treatment, osteoporosis-like phenotypes were observed in the mouse tibia cortical bone: the bone volume was significantly decreased as compared to the total volume (FIG. 25A), the cortical thickness was drastically decreased (FIG. 25B) and the bone area, but not the marrow area, was also reduced (FIGS. 25D and E). Surprisingly, but in agreement with a previous report (Grahnemo et al., 2015. J Endocrinol. 224(1):97-108), a Dex-treatment increased the mouse trabecular bone volume due to an increase in the number of trabecula and a decrease of the trabecular spacing, with no change in the trabecular thickness (data not shown).

Importantly, in marked contrast to Dex treatment, this three-month administration of CpdX or CpdX-D3, as well as of either of their enantiomers CpdX(eA), CpdX(eB), CpdX-D3(eA) or CpdX-D3(eB), did not affect the bone formation in cortical and trabecular bones (FIG. 25 and data not shown).

The expression of the WNT16 gene has been reported to affect the bone mineral density, the cortical bone thickness, the bone strength, and the risk of osteoporotic fracture (Zheng et al., 2012. PLoS Genet. July; 8(7): e1002745). Transcriptional analyses from mouse tibia samples demonstrated that the transcription of the WNT16 gene was decreased by 50% with a Dex treatment, but not with either a CpdX, CpdX(eA), CpdX(eB), CpdX-D3, CpdX-D3(eA) or CpdX-D3(eB) treatment (FIG. 26).

Conclusion

These results indicate that CpdX, CpdX-D3 and any of their enantiomers [CpdX(eA), CpdX(eB), CpdX-D3(eA) or CpdX-D3(eB)] could be safely used for clinical treatments of inflammatory diseases, unlike Dex, they do not affect bone formation.

Example 13: In Contrast to Dexamethasone (Dex), a Long-Term Treatment with Either CpdX or CpdX-D3 does not Induce a Loss of Body Weight, Nor a Change in Body Composition (See FIG. 27)

Material and Methods

B6 male mice (8-week-old) were daily subjected for three months to a subcutaneous injection of either vehicle (NaCl 0.9%), Dex, CpdX or CpdX-D3 (1 mg/kg body weight, diluted in vehicle. A pDEXA machine was used to determine the lean mass and fat mass. The statistical significance was calculated through Krustal-Walis test followed by a Dunn's multiple comparison test, *p<0.05; p<0.01; *p<0.001.

Results 8-week-old mice which, when treated for 3 months with either vehicle, CpdX or CpdX-D3 exhibited a similar increase of body weight (FIG. 27A), as well as a commensurate increase in fat mass (FIG. 27B) and lean percentage (FIG. 27C). In contrast, mice treated with Dex exhibited a net loss in total body weight (FIG. 27A), together with a disproportional increase in fat (FIG. 27B) and a decrease of lean mass (FIG. 27C).

Conclusion

These results indicate that a long-term administration of CpdX or CpdX-D3, in contrast to that of Dex, does not result in a loss of body weight, nor in an increase of fat mass and a decrease of lean mass.

Example 14: Upon a Three-Month In Vivo Administration, Mice Treated with Either CpdX, CpdX (eA), CpdX(eB), CpdX-D3, CpdX-D3(eA) or CpdX-D3(eB) do not Exhibit the Undesirable Tissue-Specific "Toxic" Side-Effects Observed in Mice Treated with Dexamethasone (Dex) (See FIG. 28)

Material and Methods

B6 male mice (8-week-old) were daily subjected for three months to a subcutaneous injection of either vehicle (NaCl 0.9%), Dex, CpdX, CpdX(eA), CpdX(eB), CpdX-D3, CpdX-D3(eA) or CpdX-D3(eB) (1 mg/kg body weight, diluted in vehicle). Following these treatments, four organs (thymus, spleen, adrenal gland and kidney) were harvested and weighted.

Results

Glucocorticoids are well known to induce a drastic thymus apoptosis (Cohen, 1992. Semin Immunol. 4(6):363-9). Accordingly, after a three-month treatment, no thymus was found in sixteen out of nineteen mice treated with Dex. In marked contrast, a treatment with either CpdX, its deuterated form CpdX-D3, or their enantiomers CpdX(eA), CpdX (eB), CpdX-D3(eA) or CpdX-D3(eB) did not result in any significant thymus apoptosis (FIG. 28A).

The spleen weight was decreased by more than 50% in Dex-treated mice, whereas it was not decreased in CpdX-, CpdX(eA)-, CpdX(eB)-, CpdX-D3-, CpdX-D3(eA)- or CpdX-D3(eB)-treated mice (FIG. 28B). A weak, but significant loss of the kidney weight was also selectively observed in mice treated with Dex (FIG. 28D).

Interestingly, the weight of the adrenal gland, in which corticosterone synthesis takes place, was decreased by a Dex treatment, whereas it was increased by a treatment with either CpdX, CpdX(eA), CpdX(eB), CpdX-D3, CpdX-D3 (eA) or CpdX-D3(eB) (FIG. 28C).

Conclusion

Upon a long-term treatment in vivo, and in marked contrast with the administration of the synthetic glucocorticoid Dexamethasone, the administration of CpdX or its deuterated form CpdX-D3, or any of their enantiomers [CpdX(eA), CpdX(eB), CpdX-D3(eA) and CpdX-D3(eB)], is not toxic, most notably for the thymus, the spleen and the adrenal gland.

Example 15: A Long-Term Daily Subcutaneous Injection of Dexamethasone (Dex) Inhibits Corticosterone Synthesis which, in Marked Contrast, is Increased by a Similar Treatment with Either CpdX, CpdX(eA), CpdX(eB), CpdX-D3, CpdX-D3 (eA) or CpdX-D3(eB) (See FIGS. 29 and 30)

Material and Methods

B6 male mice (8-week-old) were daily subjected for three months to either a subcutaneous injection of vehicle (NaCl 0.9%), Dex, CpdX, CpdX(eA), CpdX(eB), CpdX-D3, CpdX-D3(eA) or CpdX-D3(eB) (1 mg/kg body weight, diluted in vehicle).

Following this long-term treatment, blood was collected at 10 a.m. and 6 p.m. by retro-orbital puncture in lithium-heparin coated vials, and the plasmatic level of corticosterone was determined. Adrenal glands were harvested and weighted. RNA transcripts were extracted and transcripts of the Cyp11a, Cyp11b1, Cyp11b2 and HSD3β genes were analyzed by q-RT-PCR. Histological analyses of the adrenal glands were also carried out.

Results

Corticosterone is synthesized in the fasciculata zone of the cortex layer of the adrenal gland. Upon a three-month treatment with Dex, the cortex layers (see double-headed arrow in left panels), most notably the fasciculata zone (see bold double-headed arrow in right panels) of the adrenal glands were drastically decreased (FIG. 29), whereas they were markedly increased by administration of CpdX or its deuterated form CpdX-D3, or either of their enantiomers CpdX(eA), CpdX(eB), CpdX-D3(eA) or CpdX-D3(eB) (FIG. 29 and data not shown).

Transcriptional analyses from mouse adrenal glands samples demonstrated that the transcripts of Cyp11a, Cyp11b1 and HSD3β genes, which are involved in the corticosterone synthesis pathway, were inhibited by Dex treatment, while increased by CpdX, CpdX(eA), CpdX(eB), CpdX-D3, CpdX-D3(eA) or CpdX-D3(eB) treatments (FIG. 30A).

As compared to control mice (Vehicle), Dex-treated mice exhibited a much lower corticosterone levels at both 10 a.m. and 6 p.m. whereas, in marked contrast, CpdX-, CpdX(eA)-, CpdX(eB)-, CpdX-D3-, CpdX-D3(eA)- and CpdX-D3(eB)-treated mice exhibited a much higher corticosterone level at 10 a.m. (FIG. 30B).

Interestingly, transcriptional analyses from mouse adrenal glands samples also showed that the transcript of the Cyp11b2 gene, which is involved in the aldosterone synthesis pathway, is inhibited by Dex treatment, but not by CpdX, CpdX(eA), CpdX(eB), CpdX-D3, CpdX-D3(eA) or CpdX-D3(eB) treatment (FIG. 30A). In agreement with this result, histological analyses revealed that the glomerulosa zone (outermost zone of the cortex layer, see the small empty double-headed arrows in the right panels of FIG. 29), which produces aldosterone, was drastically decreased by Dex treatment, but not by either CpdX, CpdX(eA), CpdX(eB), CpdX-D3, CpdX-D3(eA) or CpdX-D3(eB) treatment (FIG. 29 and data not shown).

Conclusion

Most interestingly, these data indicate that the beneficial anti-inflammatory effects of CpdX and of its deuterated form CpdX-D3 [as well as any of their enantiomers CpdX(eA), CpdX(eB), CpdX-D3(eA) and CpdX-D3(eB)] which occur through repression of pro-inflammatory genes, result from both (i) the direct binding of CpdX or CpdX-D3 to the GR, which activates its tethered indirect transrepression function, and (ii) a further activation of this indirect transrepression function due to a CpdX- or CpdX-D3-induced increase of the blood corticosterone level, most notably during the rest period.

Example 16: In Marked Contrast with a Three-Month Administration of Dexamethasone (Dex), a Three-Month In Vivo Administration of Either CpdX, CpdX(eA), CpdX(eB), CpdX-D3, CpdX-D3 (eA) or CpdX-D3(eB) does not Induce Hyperglycemia (See FIG. 31)

Material and Methods

Upon a long-term glucocorticoid administration, hyperglycemia is a common undesirable side effect (Clore & Thurby-Hay, 2009. *Endocr Pract.* 15(5):469-74).

B6 male mice (8-week-old) were daily subjected for three months to a subcutaneous injection of either vehicle (NaCl 0.9%), Dex, CpdX, CpdX(eA), CpdX(eB), CpdX-D3, CpdX-D3(eA) or CpdX-D3(eB) (1 mg/kg body weight, diluted in vehicle). Mice were over-night-fasted. Mouse blood glucose concentration was measured before (To) and during two hours ($T_{120}$) after glucose i.p. injection (2 mg/kg body weight).

Results

After a three-month treatment, the blood glucose level in Dex-treated mice was significantly higher than in mice treated with either saline (vehicle), CpdX, CpdX(eA), CpdX (eB), CpdX-D3, CpdX-D3(eA) or CpdX-D3(eB) (FIG. 31A).

An intraperitoneal glucose tolerance test (IPGTT) showed that, upon glucose injection, a significant higher blood glucose level was observed during a two-hour period in Dex-treated mice, whereas there was no significant difference between these levels in control, CpdX-, CpdX(eA)-, CpdX(eB)-, CpdX-D3-, CpdX-D3(eA)- or CpdX-D3(eB)-treated mice (FIG. 31B).

Conclusion

These above results indicate that, in contrast to Dex, a treatment with CpdX, CpdX(eA), CpdX(eB), CpdX-D3, CpdX-D3(eA) or CpdX-D3(eB) does not significantly affect the control of the blood glucose level.

Example 17: A Three-Month In Vivo Administration of Either CpdX, CpdX(eA), CpdX(eB), CpdX-D3, CpdX-D3(eA) or CpdX-D3(eB), Unlike that of Dexamethasone (Dex), does not Induce an Insulin-Resistance (See FIGS. 31 and 32)

Material and Methods

A chronic exposure of humans to glucocorticoids (GC) is well known to result in whole-body insulin-resistance (Geer et al., 2014. *Endocrinol Metab Clin North Am.* 43(1):75-102).

B6 male mice (8-week-old) were subjected daily for three months to a subcutaneous injection of either vehicle (NaCl 0.9%), Dex, CpdX, CpdX(eA), CpdX(eB), CpdX-D3, CpdX-D3(eA) or CpdX-D3(eB) (1 mg/kg body weight, diluted in vehicle). After three months, the blood was collected at 10 a.m. by retro-orbital puncture in lithium-heparin coated vials, and the plasmatic level of insulin was determined.

For the intraperitoneal insulin tolerance test (IPITT), mice were fasted for 6 hours before test. The blood glucose concentration was measured both before (To) and during a one-hour period after insulin i.p. injection (0.75 U/kg body weight).

Following this three-month treatment, liver samples were harvested and lysed in the RIPA buffer (20 mM Tris pH 8, 150 mM NaCl, 10% glycerol, 1% NP-40 and 2 mM EDTA). Antibodies from Cell Signaling were used to assess by Western-Blotting the relative level of p-IRS1 (S318), IRS-1, p-AKT (S473) and AKT.

Results

After a three-month treatment, the blood insulin level revealed a hyperinsulinemia in Dex-treated mice, but not in mice treated with either saline (vehicle), CpdX, CpdX(eA), CpdX(eB), CpdX-D3, CpdX-D3(eA) or CpdX-D3(eB) (FIG. 32A). As an hyperglycemia was observed in Dex-treated mice (FIG. 31A) and an IPITT test disclosed a significant impaired response to insulin in these mice (FIG. 32B), they may reveal an insulin resistance. In keeping with this suggestion, western-blot analyses from liver extracts showed in Dex-treated mice, but not in vehicle-, CpdX- or CpdX-D3-treated mice, a decrease in phosphorylated insulin receptor substrate 1 (p-IRS1 S318) (FIG. 32C). As expected the phosphorylation of insulin-stimulated protein kinase B (p-AKT S473) was also decreased in Dex-treated mice (FIG. 32C).

Conclusion

These results indicate that, in contrast to Dexamethasone, a treatment with CpdX, its deuterated form CpdX-D3, or any of their enantiomers [CpdX(eA), CpdX(eB), CpdX-D3(eA) or CpdX-D3(eB)], does not induce an insulin resistance.

Example 18: In Marked Contrast to Dexamethasone (Dex), a Three-Month In Vivo Administration of Either CpdX, CpdX(eA), CpdX(eB), CpdX-D3, CpdX-D3(eA) or CpdX-D3(eB) does not Induce a Fatty Liver (See FIGS. 33 to 35)

Material and Methods

B6 male mice (8-week-old) were daily subjected for three months to a subcutaneous injection of either vehicle (NaCl 0.9%), Dex, CpdX, CpdX(eA), CpdX(eB), CpdX-D3, CpdX-D3(eA) or CpdX-D3(eB) (1 mg/kg body weight, diluted in vehicle). Following this treatment, blood was collected at 10 a.m. by retro-orbital puncture in lithium-heparin coated vials. The plasmatic levels of total cholesterol and bile acids were determined.

Liver samples were harvested. Lipid deposition in the liver was revealed by 5% Red oil staining of frozen sections. RNA transcripts were extracted from liver samples and the transcripts of fatty acid synthase (FASN) and Stearoyl-CoA desaturase 1 (SCD1) genes were analyzed by q-RT-PCR.

Results

Upon a three-month treatment, there was a marked lipid deposition in the liver of mice subjected to a daily subcutaneously administration of Dex, which was not observed in mice treated with either CpdX or CpdX-D3, their enantiomers or Vehicle (FIG. 33). Accordingly, an increase in transcripts of fatty acid synthase (FASN) and Stearoyl-CoA desaturase 1 (SCD1), which are critically involved in liver lipogenesis, was observed in liver of Dex-treated mice, but not of vehicle-, CpdX-, CpdX(eA)-, CpdX(eB)-, CpdX-D3-, CpdX-D3(eA)- or CpdX-D3(eB)-treated mice (FIG. 34).

Hypercholesterolemia is a main cause of non-alcoholic fatty liver diseases (NAFLDs) (Kim et al., 2014. *PLoS One.* 9(6):e97841). Cholesterol is converted in liver into bile acids. Accordingly, a high level of bile acids was also observed in patients exhibiting fatty liver diseases (Aranha et al., 2008. *Eur J Gastroenterol Hepatol.* 20(6):519-25). As expected, Dex-treated, but not CpdX-, CpdX(eA)-, CpdX (eB)-, CpdX-D3-, CpdX-D3(eA)- or CpdX-D3(eB)-treated mice, exhibited a clear increase in blood cholesterol and bile acids' levels (FIG. 35).

Conclusion

A three-month in vivo treatment with CpdX or its deuterated form CpdX-D3, or either of their enantiomers [CpdX (eA), CpdX(eB), CpdX-D3(eA) or CpdX-D3(eB)], does not induce a fatty liver disease, in marked contrast with a similar treatment with Dex.

The invention claimed is:

1. A method for treating an inflammatory disorder in a subject in need thereof, comprising administering to said subject a composition comprising one enantiomer of a SElective Glucocorticoid Receptor Agonistic Modulator (SEGRAM) of Formula 1:

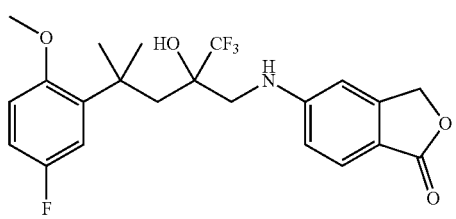

(Formula 1-CpdX)

or a pharmaceutically acceptable salt thereof, wherein:

(i) the inflammatory disorder is selected from the group consisting of atopic dermatitis, contact dermatitis, psoriasis, solar dermatitis, eczema, urticaria, vitiligo, erythema nodosum, erythema multiforme, dermatomyositis, scleroderma, angioedema, lichen planus, cutaneous necrotizing venulitis, insect bite skin inflammation, allergic asthma, allergic sinusitis, allergic rhinitis, hay fever, allergic conjunctivitis, rhinoconjunctivitis, rheumatoid arthritis, inflammatory bowel disease (IBD), Crohn's disease, ulcerative colitis, colitis, type 2 diabetes, hyperlipidemia, and postmenopausal-induced metabolic syndrome and steatosis, and said enantiomer of the SEGRAM corresponds to a first elution peak of a supercritical fluid chromatography (SFC) of a racemic mixture of the SEGRAM of Formula 1 [CpdX(eA)] or of a racemic mixture of the SEGRAM of Formula 1 in its deuterated form with Formula 2 [CpdX-D3(eA)],

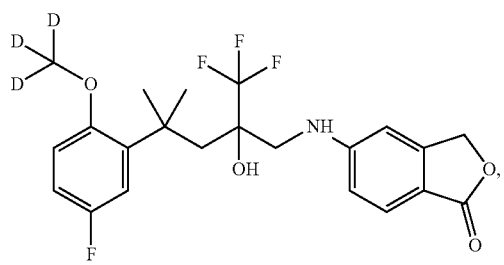

(Formula 2-CpdX-D3)

or (ii) the inflammatory disorder is selected from the group consisting of atopic dermatitis, contact dermatitis, psoriasis, solar dermatitis, eczema, urticaria, vitiligo, erythema nodosum, erythema multiforme, dermatomyositis, scleroderma, angioedema, lichen planus, cutaneous necrotizing venulitis, insect bite skin inflammation, allergic conjunctivitis, rhinoconjunctivitis, inflammatory bowel disease (IBD), Crohn's disease, ulcerative colitis, colitis, type 2 diabetes, hyperlipidemia, and postmenopausal-induced metabolic syndrome and steatosis, and said enantiomer of the SEGRAM corresponds to a second elution peak of a supercritical fluid chromatography (SFC) of a racemic mixture of the SEGRAM of Formula 1 [CpdX(eB)] or of a racemic mixture of the SEGRAM of Formula 1 in its deuterated form with Formula 2 [CpdX-D3(eB)].

2. The method according to claim 1, wherein said enantiomer of the SEGRAM does not induce neither a direct transactivation function, nor a direct transrepression function of the glucocorticoid receptor, but selectively induces the indirect tethered transrepression function of the glucocorticoid receptor.

3. The method according to claim 1, wherein said enantiomer of the SEGRAM does not induce steroidal anti-inflammatory drugs (SAIDs)-associated side effects upon administration to a subject in need thereof.

4. The method according to claim 3, wherein SAIDs-associated side effects are selected from the group consisting of skin atrophy; osteoporosis; growth suppression; body weight loss; fat mass gain; lean mass loss, thymus, spleen, kidney and/or adrenal gland apoptosis; corticosterone synthesis inhibition; adrenal suppression, hyperglycemia, insulin resistance; hyperinsulinemia and fatty liver.

5. The method according to claim 1, wherein the inflammatory disorder is selected from the group consisting of atopic dermatitis, contact dermatitis, allergic asthma, psoriasis, allergic conjunctivitis, rheumatoid arthritis and ulcerative colitis, and said enantiomer of the SEGRAM corresponds to the first elution peak of the supercritical fluid chromatography (SFC) of the racemic mixture of the SEGRAM of Formula 1 [CpdX(eA)] or of the racemic mixture of the SEGRAM of Formula 1 in its deuterated form with Formula 2 [CpdX-D3(eA)].

6. The method according to claim 1, wherein the inflammatory disorder is selected from the group consisting of atopic dermatitis, contact dermatitis, psoriasis, allergic conjunctivitis, and ulcerative colitis, and said enantiomer of the SEGRAM corresponds to the second elution peak of the supercritical fluid chromatography (SFC) of the racemic mixture of the SEGRAM of Formula 1 [CpdX(eB)] or of the racemic mixture of the SEGRAM of Formula 1 in its deuterated form with Formula 2 [CpdX-D3(eB)].

* * * * *

SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Consensus positive glucocorticoid-responsive
      element ((+)GRE)
<220> FEATURE:
<221> NAME/KEY: misc_feature
<222> LOCATION: 7
<223> OTHER INFORMATION: /note="n can be any of A, T, C or G"
<220> FEATURE:
<221> NAME/KEY: misc_feature
<222> LOCATION: 8
<223> OTHER INFORMATION: /note="n can be any of A, T, C or G"
<220> FEATURE:
<221> NAME/KEY: misc_feature
<222> LOCATION: 9
<223> OTHER INFORMATION: /note="n can be any of A, T, C or G"

<400> SEQUENCE: 1
ggaacannnt gttct                                                      15

<210> SEQ ID NO 2
<211> LENGTH: 10
<212> TYPE: DNA

```
<213> ORGANISM: Artificial Sequence
<220> FEATURE:
<223> OTHER INFORMATION: Consensus negative glucocorticoid-responsive
      element (nGRE)
<220> FEATURE:
<221> NAME/KEY: misc_feature
<222> LOCATION: 5
<223> OTHER INFORMATION: /note="n can be any of A, T, C or G"
      /note="n can be 0, 1 or 2 nucleic acids"

<400> SEQUENCE: 2 ctccnggaga                                                                10

<210> SEQ ID NO 3
<211> LENGTH: 10
<212> TYPE: DNA
<213> ORGANISM: Artificial Sequence
<220> FEATURE:
<223> OTHER INFORMATION: NF-N:B-binding site
<220> FEATURE:
<221> NAME/KEY: misc_feature
<222> LOCATION: 4
<223> OTHER INFORMATION: /note="r can be any of G or A"
<220> FEATURE:
<221> NAME/KEY: misc_feature
<222> LOCATION: 5
<223> OTHER INFORMATION: /note="n can be any of A, T, C, or G"
<220> FEATURE:
<221> NAME/KEY: misc_feature
<222> LOCATION: 6
<223> OTHER INFORMATION: /note="n can be any of A, T, C, or G"
<220> FEATURE:
<221> NAME/KEY: misc_feature
<222> LOCATION: 7
<223> OTHER INFORMATION: /note="Y can be any of T or C"
<220> FEATURE:
<221> NAME/KEY: misc_feature
<222> LOCATION: 8
<223> OTHER INFORMATION: /note="Y can be any of T or C"

<400> SEQUENCE: 3 gggrnnyycc                                                                10
```